US011554227B2

(12) United States Patent
Trzecieski

(10) Patent No.: US 11,554,227 B2
(45) Date of Patent: *Jan. 17, 2023

(54) METHOD AND DEVICE FOR VAPORIZING PHYTO MATERIAL

(71) Applicant: GSEH Holistic, Inc., Vancouver (CA)

(72) Inventor: Michael Alexander Trzecieski, Toronto (CA)

(73) Assignee: GSEH Holistic, Inc., Vancouver (CA)

( * ) Notice: Subject to any disclaimer, the term of this patent is extended or adjusted under 35 U.S.C. 154(b) by 697 days.

This patent is subject to a terminal disclaimer.

(21) Appl. No.: 15/889,262

(22) Filed: Feb. 6, 2018

(65) Prior Publication Data

US 2018/0221604 A1 Aug. 9, 2018

Related U.S. Application Data

(60) Provisional application No. 62/505,105, filed on May 11, 2017, provisional application No. 62/460,875, (Continued)

(51) Int. Cl.
*A61M 15/00* (2006.01)
*A61M 15/06* (2006.01)
(Continued)

(52) U.S. Cl.
CPC ............. *A61M 15/06* (2013.01); *A24F 40/46* (2020.01); *A24F 40/48* (2020.01); *A24F 40/485* (2020.01);
(Continued)

(58) Field of Classification Search
CPC ...... A24F 1/26; A24F 1/28; A24F 1/30; A24F 5/02; A24F 47/002; A24F 47/008; A24F 9/14; A24F 21/00; A24F 2700/00; A24F 2700/01; A61M 15/06; A61M 2205/215; A61M 11/041; A61M 11/042; A61M 11/045; A61M 11/048; A61M 11/06; A61M 11/065
See application file for complete search history.

(56) References Cited

U.S. PATENT DOCUMENTS 4,031,904 A * 6/1977 Karl .......................... A24F 1/30
131/173
4,133,318 A 1/1979 Gross et al.
(Continued)

*Primary Examiner* — LaToya M Louis
(74) *Attorney, Agent, or Firm* — Bereskin & Parr LLP/S.E.N.C.R.L., s.r.l.

(57) ABSTRACT

Vaporization element, device and method for vaporizing phyto material. A hollow member defining a fluid pathway is positioned proximate a heating element with a phyto material contact surface. An electrical heater is positioned on the opposite side of the phyto material contact surface. Phyto material or extract deposited on the phyto material contact surface can be vaporized by heat from the electrical heater. The vapor can enter the fluid pathway and pass through the hollow member to an inhalation aperture. The electrical heater may be powered by an electrical power source provided in a support unit. The hollow member can be mounted to a vapor processing device that cools and/or filters the vapor before it reaches the inhalation aperture. The support unit may have securement mechanisms to attach the vapor processing device to the vaporization device.

34 Claims, 39 Drawing Sheets

156

Related U.S. Application Data filed on Feb. 20, 2017, provisional application No. 62/455,174, filed on Feb. 6, 2017.

(51) Int. Cl.
| | |
|---|---|
| *A61M 11/04* | (2006.01) |
| *A24F 40/46* | (2020.01) |
| *A24F 40/48* | (2020.01) |
| *A24F 40/485* | (2020.01) |
| *A24F 40/51* | (2020.01) |
| *A24F 40/10* | (2020.01) |

(52) U.S. Cl.
CPC ........... *A24F 40/51* (2020.01); *A61M 11/042* (2014.02); *A24F 40/10* (2020.01); *A61M 2205/3334* (2013.01); *A61M 2205/3372* (2013.01); *A61M 2205/3375* (2013.01); *A61M 2205/3653* (2013.01); *A61M 2205/502* (2013.01); *A61M 2205/581* (2013.01); *A61M 2205/80* (2013.01); *A61M 2205/8206* (2013.01)

(56) References Cited

U.S. PATENT DOCUMENTS

| | | | |
|---|---|---|---|
| 10,004,264 | B2 | 6/2018 | Rado |
| 10,021,909 | B2 | 7/2018 | Rado |
| 10,118,013 | B2 * | 11/2018 | Krietzman ........... H05B 1/0244 |
| 10,138,113 | B2 * | 11/2018 | Murison .................. B67D 7/54 |
| 10,149,498 | B2 * | 12/2018 | Batista ................. H05B 3/145 |
| 10,166,349 | B2 * | 1/2019 | Davidson ................ A61P 25/30 |
| 10,321,721 | B2 | 6/2019 | Rado |
| 10,327,470 | B2 | 6/2019 | Rado |
| 10,537,690 | B2 | 1/2020 | Trzecieski |
| 10,561,804 | B1 * | 2/2020 | Culligan ............. H05B 1/0244 |
| 2006/0086364 | A1 | 4/2006 | Liu |
| 2009/0095310 | A1 | 4/2009 | Chaoui |
| 2011/0308521 | A1 | 12/2011 | Kofford |
| 2013/0032159 | A1 | 2/2013 | Capuano |
| 2014/0083441 | A1 | 3/2014 | Kaplani |
| 2014/0130812 | A1 | 5/2014 | Kling et al. |
| 2014/0255014 | A1 | 9/2014 | Bishara |
| 2016/0030692 | A1 | 2/2016 | Burk et al. |
| 2016/0066619 | A1 | 3/2016 | Di Carlo |
| 2016/0206001 | A1 | 7/2016 | Eng et al. |
| 2017/0055579 | A1 | 3/2017 | Kuna et al. |
| 2017/0065776 | A1 | 3/2017 | Trzecieski |
| 2017/0189638 | A1 * | 7/2017 | Osada ................... A61M 16/16 |
| 2017/0361040 | A1 | 12/2017 | Trzecieski |
| 2018/0110938 | A1 | 4/2018 | Trzecieski |
| 2018/0192695 | A1 * | 7/2018 | Risolia ...................... A24F 1/30 |
| 2018/0304032 | A9 | 10/2018 | Trzecieski |
| 2020/0222642 | A1 | 7/2020 | Trzecieski |

* cited by examiner

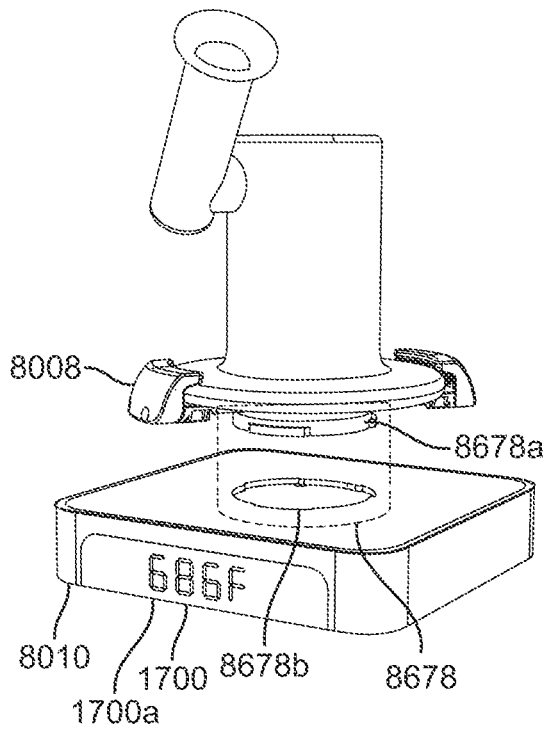
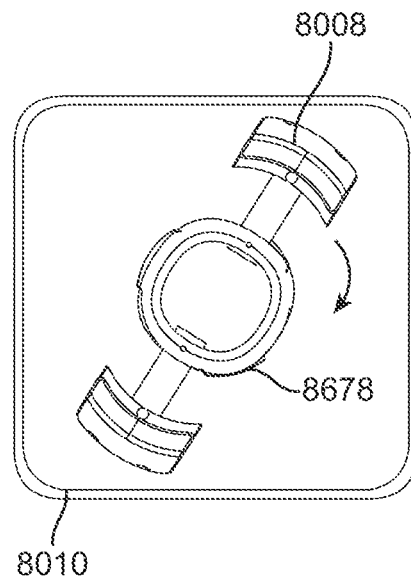
FIG. 5A
FIG. 5B
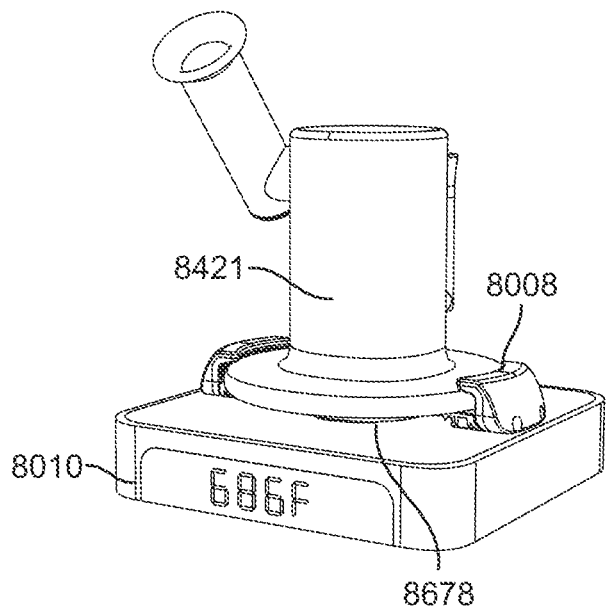
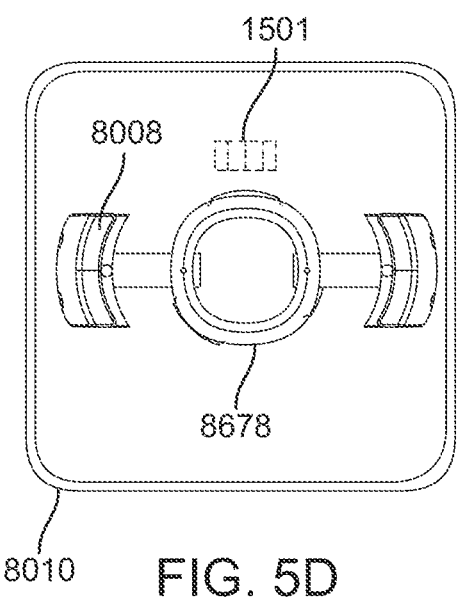
FIG. 5C
FIG. 5D

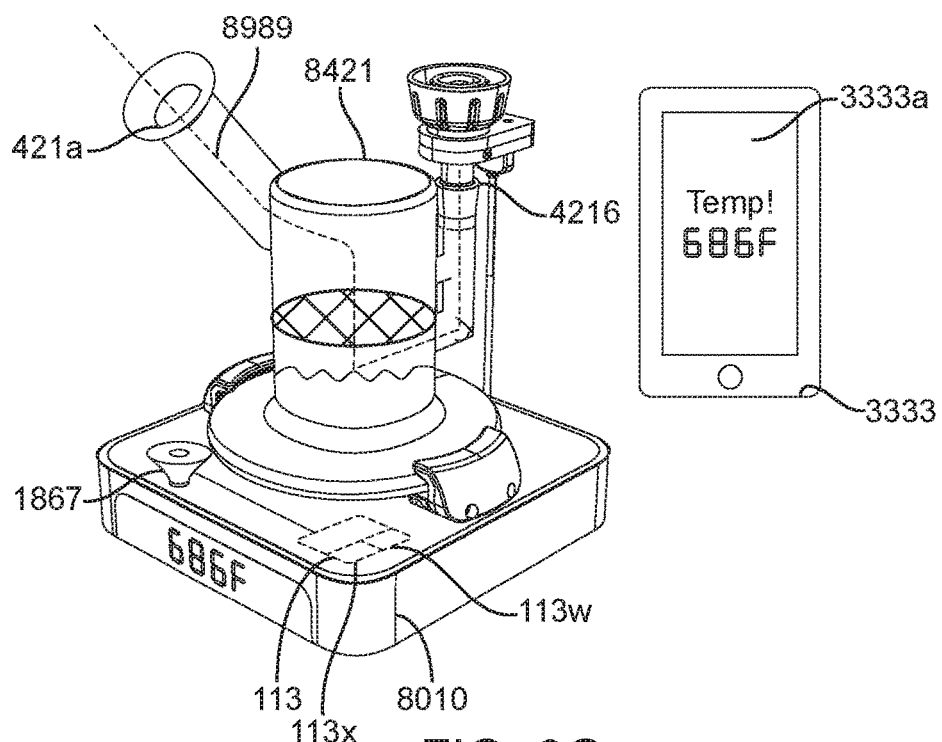
FIG. 6G
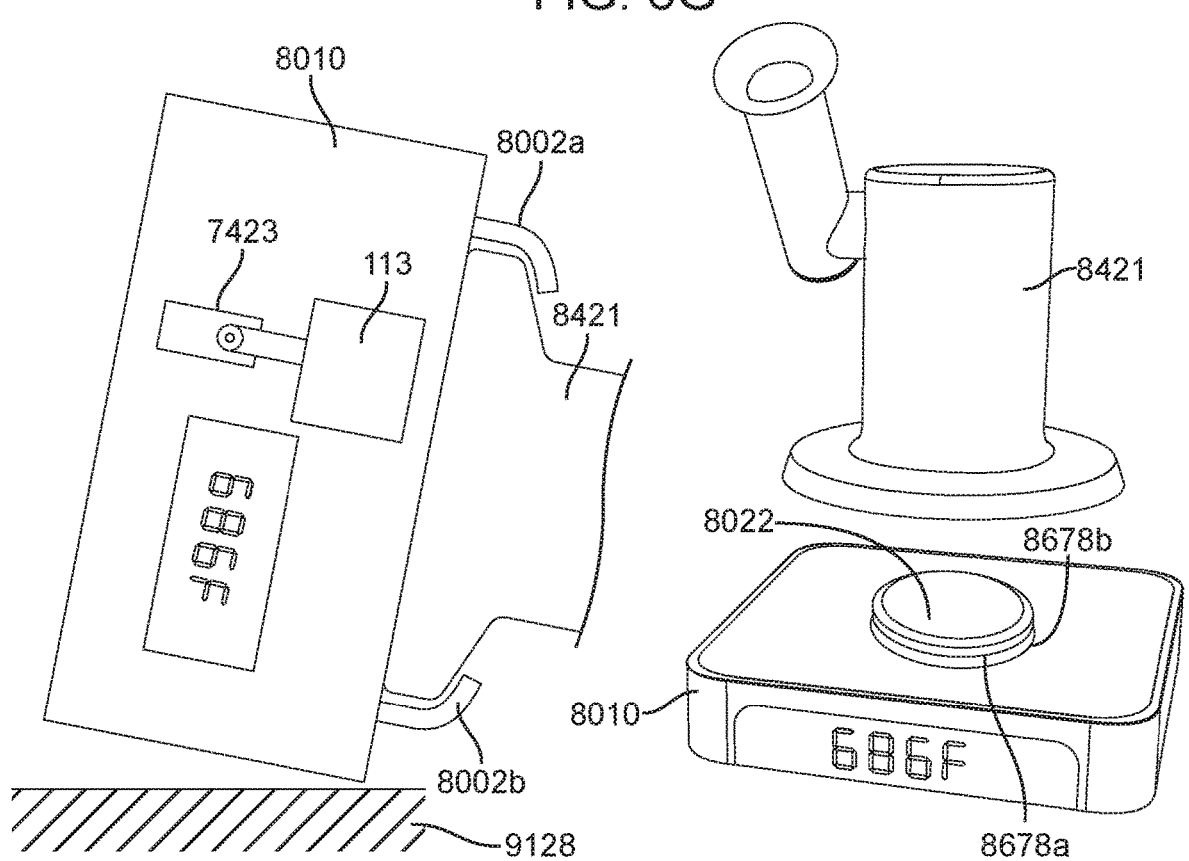
FIG. 6H
FIG. 6I

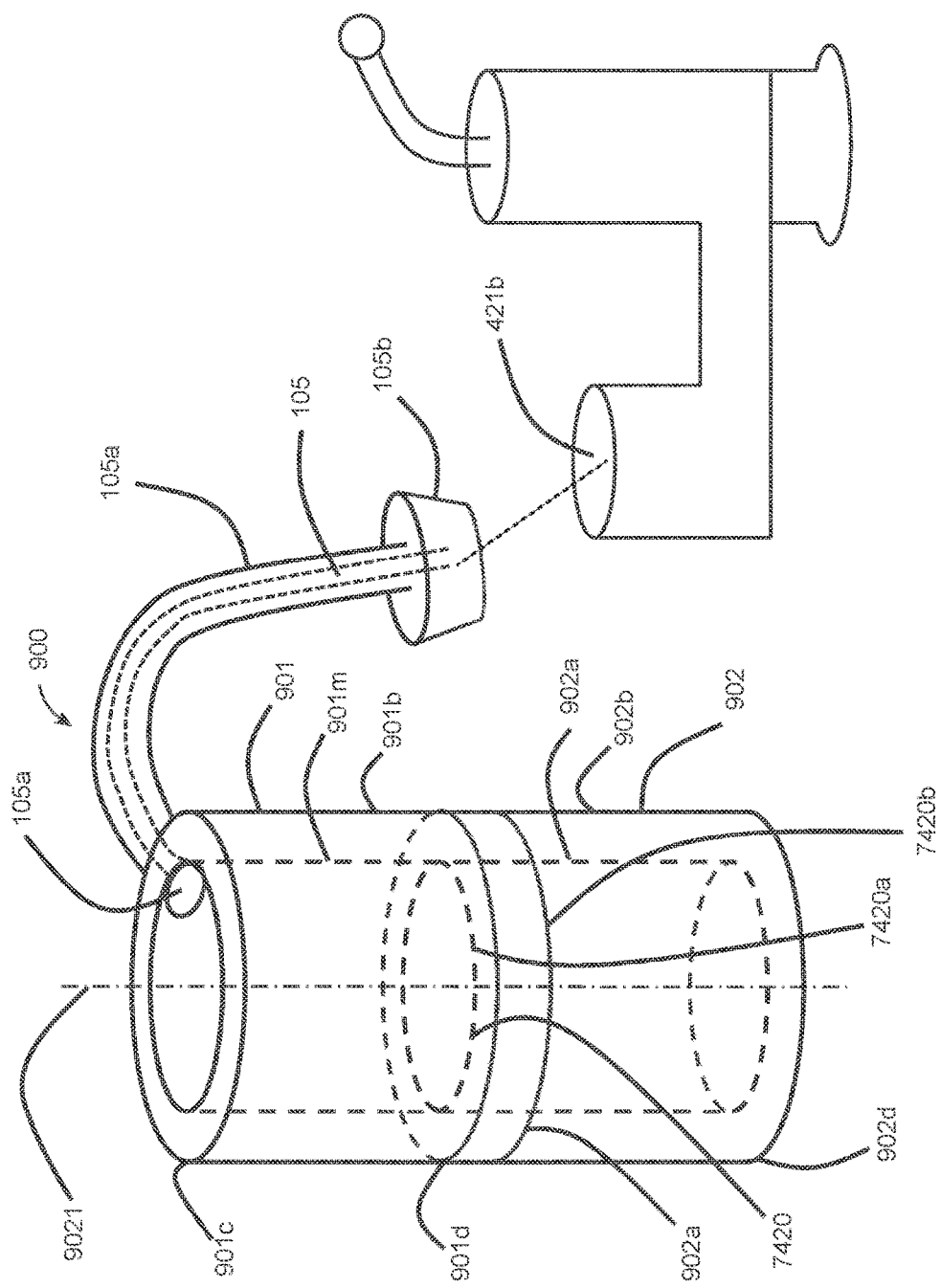

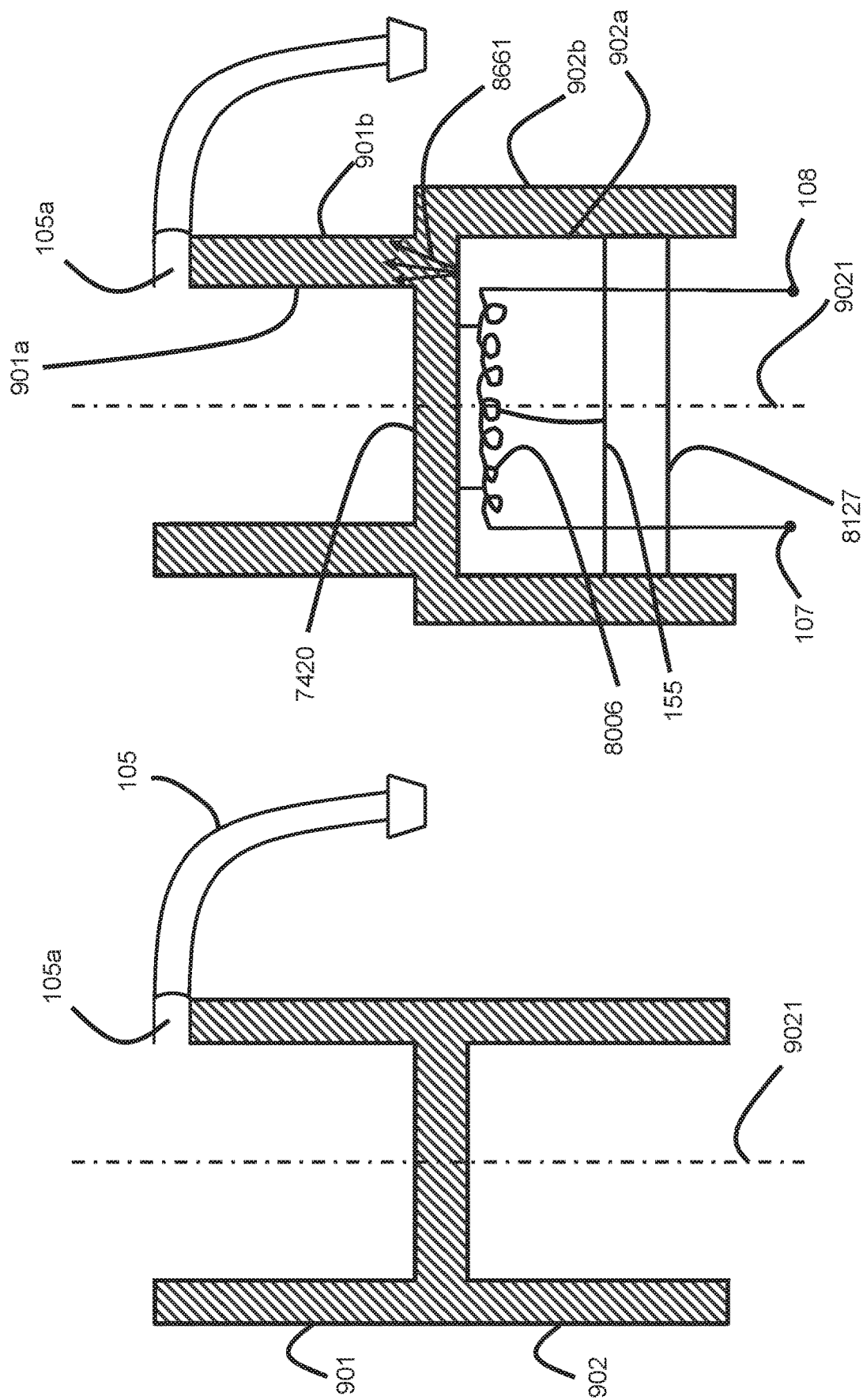

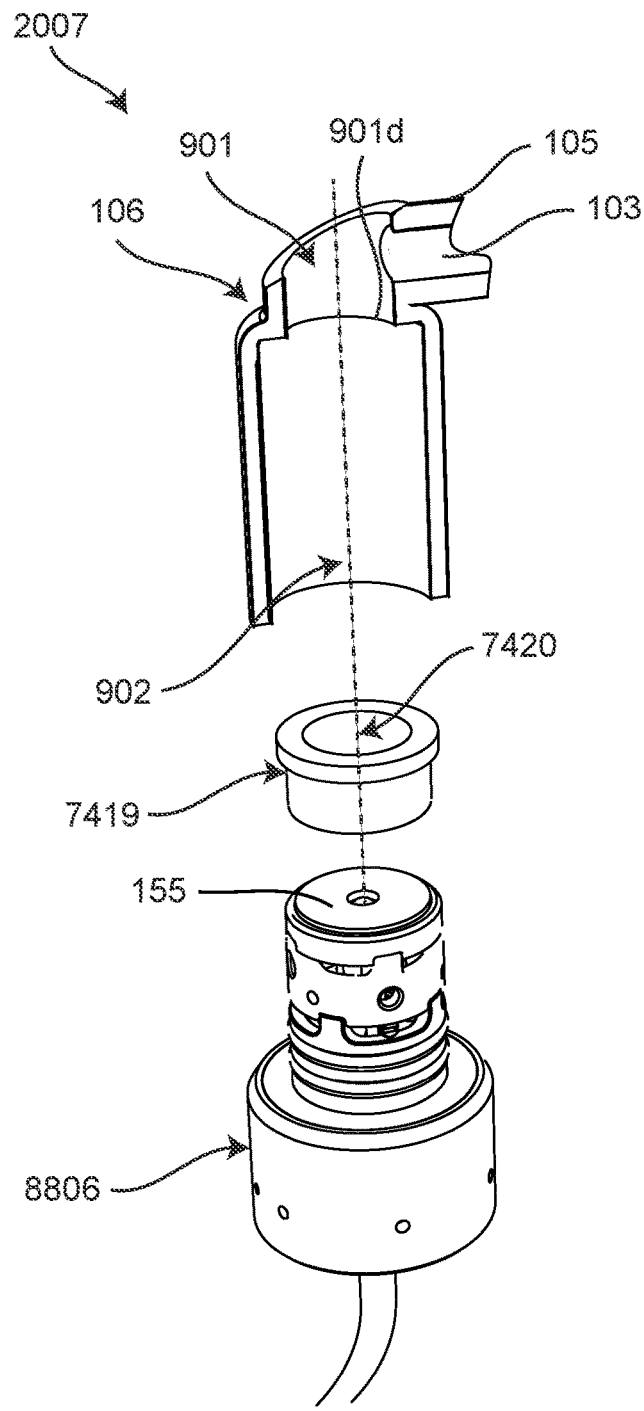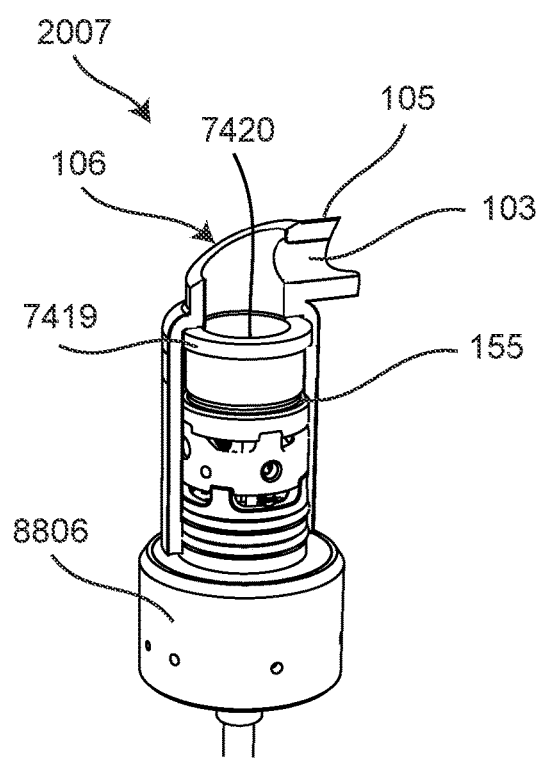
FIG. 11A
FIG. 11B

METHOD AND DEVICE FOR VAPORIZING PHYTO MATERIAL

CROSS-REFERENCE TO RELATED APPLICATIONS

This application claims the benefit of U.S. Provisional Application No. 62/455,174, filed Feb. 6, 2017; U.S. Provisional Application No. 62/460,875, filed Feb. 20, 2017; and U.S. Provisional Application No. 62/505,105, filed May 11, 2017 the entirety of each of which is incorporated herein by reference.

FIELD OF THE INVENTION

This disclosure relates generally to vaporization of phyto materials, and in particular to methods and devices for vaporizing phyto materials and phyto material extracts.

BACKGROUND

The following is intended to introduce the reader to the detailed description that follows and not to define or limit the claimed subject matter.

Aromatherapy generally uses essential oils for therapeutic benefits. Essential oils can be extracted from phyto materials, such as the leaves of plants. In some cases, essential oils may be massaged into the skin to provide therapeutic benefits. In other cases, essential oils may be ingested or inhaled for therapeutic purposes.

In some cases, phyto materials may be heated in order to release the essential oils therefrom. By heating phyto materials at predetermined temperatures, essential oils and extracts can be boiled off. Depending on the temperature at which the phyto materials are heated, an aroma or vapor may be given off. This vapor may be inhaled by a user for its therapeutic benefits.

Various methods of vaporizing phyto materials, such as cannabis products, are known. Devices that vaporize phyto materials are generally known as vaporizers. These devices may be used to vaporize cannabis phyto materials at temperatures in the range of about 330 degrees Fahrenheit to about 440 degrees Fahrenheit.

In some cases, oils or extracts derived or extracted from the phyto materials may also be vaporized. For cannabis oils or extracts, temperatures in the range of about 500 to 700 degrees Fahrenheit may be applied to vaporize these oils or extracts. In many cases, a metal or ceramic element is heated using a torch in order to reach the desired temperature. The heated heating element may then be brought into contact with the extract to generate vapor. This vapor can then be inhaled by a user, sometimes after passing through a cooling channel. In many cases, however, the torch may heat the element to over 1000 degrees Fahrenheit, which can result in combustion of the phyto material extract rather than vaporization.

SUMMARY

The following introduction is provided to introduce the reader to the more detailed description to follow and not to limit or define any claimed or as yet unclaimed invention. One or more inventions may reside in any combination or sub-combination of the elements or process steps disclosed in any part of this document including its claims and figures.

In accordance with an aspect of this disclosure, there is provided a vaporization device for vaporizing phyto material and/or phyto material extracts. The vaporization device can include a vaporization element that is usable to heat phyto material extracts to a desired vaporization temperature to generate an extract vapor. The vaporization device can define a fluid pathway extending from the vaporization element to an inhalation aperture. The extract vapor can flow through the fluid pathway to the inhalation aperture whereby a user can inhale the vapor. The vapor may be drawn into and through the fluid pathway by a user inhaling via the inhalation aperture.

In some cases, the vaporization device may include a water pipe or other vapor processing device. The vapor processing device can define a cooling and/or filtering portion of the fluid pathway that extends from a processing device input port to the inhalation aperture.

The vaporization element can include a heating element or phyto material holder. The heating element may be shaped to receive and hold phyto material extract that is to be vaporized.

The vaporization element can also include an electrical heater that can be used to vaporize the phyto material extract. The electrical heater can be arranged to heat the heating element (or at least a portion thereof) which can in turn heat phyto material extract that is positioned on a phyto material contact surface of the heating element.

The vaporization element can also include a vapor inlet. The vapor inlet can be positioned in close proximity to the phyto material holder. The vaporization element may define a fluid pathway that extends from the vapor inlet to a vaporization element vapor outlet.

In some cases, the vapor outlet may be configured to be fluidly coupled with the input port of a vapor processing device such as a water pipe. The vapor processing device may define a processing device pathway portion that extends to an inhalation aperture usable by a user to inhale extract vapor.

In some other cases, the vaporization element vapor outlet may be coupled directly to an inhalation aperture. The vapor outlet may even define the inhalation aperture. In such cases, a separate vapor processing device may be omitted.

Typically, the vapor inlet may be positioned at least slightly above the phyto material holder. Accordingly, as the vapor rises from the heated phyto material extract it can pass by the vapor inlet. The vapor may then be drawn through the vapor inlet into the fluid pathway by a user inhaling through the inhalation aperture at the other end of the fluid pathway.

In accordance with an embodiment described herein, there is provided a vaporization device for vaporizing phyto material. The device may be usable with a vapor processing device having an input port and an inhalation aperture with a processing device fluid pathway formed therebetween. The vaporization device may be operable to vaporize phyto material and/or phyto material extract.

The vaporization device can include a vaporization element. The vaporization element can include a hollow member extending from a first end to a second end opposite the first end, the hollow member defining a vaporization element fluid pathway from a vapor inlet positioned at the first end to a vapor outlet positioned at the second end, wherein the hollow member is engageable with the vapor processing device with the outlet fluidly engaged with the input port of the vapor processing device; a heating element disposed proximate the first end of the hollow member, the heating element defining a phyto material contact surface; and an electrical heater adjacent to the heating element.

The vaporization device can also include a support unit that is removably mountable to the vapor processing device.

The support unit may a bottom surface and a top surface opposite the bottom surface, where the top surface has a securement mechanism for securing the vapor processing device to the support unit in an upright position when the support unit is positioned in an in-use position in which the top surface faces substantially upwards. The support unit can also include an electrical power source; and, a control circuit electrically coupled to the electrical power source. The vaporization device can further include an electrical connector that is engageable with the support unit and the electronic vaporization element whereby the electrical heater is coupled to the control circuit.

The control circuit may be configured to controllably provide electrical power from the electrical power source to the electrical heater to heat the phyto material contact surface to a predefined vaporization temperature whereby when phyto material is positioned on the phyto material contact surface a vapor is emitted. The vapor may flow from the first end of the hollow member to the inhalation aperture upon inhalation from the inhalation aperture.

The electrical heater may be positioned between first and second electrical contacts. The first and second electrical contacts can be used to complete a circuit through the electrical heater, e.g. by coupling the electrical heater to a power source.

In some embodiments, the securement mechanism may include an adjustable clamp. The adjustable clamp may have a first jaw and a second jaw disposed opposite the first jaw, each of the first jaw and the second jaw defining processing device engagement surfaces in a facing arrangement frictionally engage the vapor processing device when the vapor processing device is positioned between the processing device engagement surfaces; a clamp track section with a first track defining a first translation path for the first jaw and a second track defining a second translation path for the second jaw, where the first jaw and second jaw are translatable along the first track and the second track respectively towards and away from one another. The first jaw and second jaw may be moved towards one another to frictionally engage a vapor processing device positioned between the first jaw and the second jaw.

In some embodiments, the clamp may include a lock coupled to the first jaw and the second jaw, the lock may be adjustable between a locked position in which the first jaw and second jaw are secured in place along the first track and the second track respectively, and an unlocked position in which the first jaw and second jaw are translatable along the first track and the second track respectively to adjust the separation between the first jaw and the second jaw.

In some embodiments, the first jaw and the second jaw may both be mechanically coupled to a lead screw. The lead screw may be rotatable to translate the first jaw and the second jaw along the first track and the second track respectively with the lead screw rotatable in a first direction to decrease a separation between the first jaw and the second jaw and the lead screw rotatable in a second direction to increase the separation between the first jaw and the second jaw.

In some embodiments, the vaporization device may also include a motor. The motor may be mechanically coupled to the lead screw and electrically coupled to the control circuit. The control circuit can be configured to operate the motor to controllably rotate the lead screw to change the separation distance between the first jaw and the second jaw.

In some cases, the vaporization device may also include a twist lock coupling having rotating portion and a static portion, the rotating portion can be coupled to the adjustable clamp so the rotating portion can be frictionally engaged with the vapor processing device using the adjustable clamp, and the static portion can be coupled with the support unit, the twist lock coupling operable in a locked mode of operation and an unlocked mode of operation, in the locked mode of operation the rotating portion and the static portion are frictionally engaged, and in the unlocked mode of operation the rotating portion and the static portion are unengaged.

In some embodiments, the securement mechanism may include an adjustable clamping mechanism having a first jaw and a second jaw disposed opposite the first jaw, the first and second jaws can be mechanically coupled to a lead screw that is rotatable in a first direction to reduce a separation between the first jaw and the second jaw and the lead screw is rotatable in a second direction to increase a separation between the first jaw and the second jaw; a twist lock coupling having a rotating portion and a static portion, the rotating portion coupled with the adjustable clamping mechanism and the static portion coupled with the support unit, the twist lock coupling may be operable in a locked mode of operation and an unlocked mode of operation, in the locked mode of operation the rotating portion and the static portion can be frictionally engaged and the vapor processing device can be coupled to the support unit via the adjustable clamp and the twist lock coupling, and in the unlocked mode of operation the rotating portion and the static portion can be unengaged and the vapor processing device is uncoupled from the support unit, where the rotating portion of the twist lock coupling is frictionally engageable with the vapor processing device using the adjustable clamping mechanism, and the rotating portion can be inserted into the static portion and twisted into place with a rotation in a locking direction to initiate the locked mode of operation.

In some embodiments, the vaporization device may include a temperature sensor in thermal communication with the heating element. The temperature sensor may be operable to measure a temperature of the heating element and to generate a temperature signal based on the measured temperature of the heating element. The control circuit can be configured to receive the temperature signal from the temperature sensor and to determine a temperature of the phyto material contact surface based on the received temperature signal.

In some embodiments, the support unit may include a first wireless transceiver and a power coupling output port; the electronic vaporization element may include a power coupling input port, a second wireless transceiver and a second control circuit that is electrically coupled to the electrical heater, to the power coupling input port, to the second wireless transceiver, and to the temperature sensor, and the second control circuit can be configured to determine a temperature of the electrical heater. The electrical connector may be connectable to the power coupling output port and to the power coupling input port to electrically couple the electrical heater to the control circuit; and the control circuit can be configured to receive the temperature signal from the second control circuit via the first wireless transceiver and the second wireless transceiver.

In some embodiments, the first wireless transceiver can include a first optical transceiver and the second wireless transceiver can include a second optical transceiver. The first optical transceiver and second optical transceiver may be configured to communicate using optical signals.

In some embodiments, the temperature sensor may be coupled to the control circuit by the electrical connector when the electrical connector is engaged with the support unit and the electronic vaporization.

In some embodiments, the control circuit can be configured to pulse width modulate the electrical power provided to the resistive heater to maintain the phyto material contact surface at the predefined vaporization temperature.

In some embodiments, the electronic vaporization element may include a second temperature sensor and a second control circuit that is electrically coupled to the second temperature sensor and to the first control circuit. The second temperature sensor may be positioned to measure a temperature of ambient air; and the control circuit can configured to determine the predefined vaporization temperature based on the temperature of the ambient air. The control circuit may adjust the power provided to the electrical heater based on the temperature of the ambient air.

In some embodiments, the heating element has a phyto material contact element with a second side facing the electrical heater, and the phyto material contact surface is defined on a first side of the phyto material contact element opposite the second side. Thermal energy from the electrical heater is transmittable through the phyto material contact element from the second side to the phyto material contact surface.

In some embodiments, the phyto material contact surface may be manufactured of glass and the electrical heater may be a ceramic heater. The ceramic heater may be separated from phyto material positioned on the phyto material contact surface by the phyto material contact element.

In some embodiments, the phyto material contact surface may be disposed proximate to, and below, the first end of the hollow member.

In some embodiments, the phyto material contact element may include glass and the hollow member may include glass.

In some embodiments, the phyto material contact surface may include ceramic and the hollow member may include ceramic.

In some embodiments, the electrical heater may be releasably attached to the heating element using a frictional coupling.

In some embodiments, the device may also include at least one light-emitting diode (LED) electrically coupled to the control circuit, the at least one light-emitting diode can be arranged to emit light at least partially towards the vapor processing device when the vapor processing device is in the in-use position. The vapor processing device may reflect and refract the light emitted towards and through the vapor processing device.

In some embodiments, the at least one LED may include a plurality of three-color light emitters arranged in a two dimensional matrix.

In some embodiments, the securement mechanism may include a suction cup device. The suction cup device may be usable to form at least a partial vacuum between the suction cup device and the vapor processing device.

In some embodiments, the securement mechanism may include an adhesive tape for adhering the vapor processing device to the support unit.

In some embodiments, the device may include a voice recognition processor coupled with the control circuit, the voice recognition processor may be configured to receive voice commands from a user for at least one of controlling heating of the electrical heater, adjusting the predefined vaporization temperature, and disabling the electrical heater. In some cases, the voice recognition processor may be an Alexa Voice Services (AVS) and a Google® Home Voice Services voice recognition processor.

In some embodiments, the support unit may have a cavity shaped to receive the voice recognition processor. In some cases, the voice recognition processor may include at least one LED operable to illuminate at least a portion of the vapor processing device.

In some embodiments, the device may include a Wi-Fi module coupled to the control circuit. The control circuit may be remotely configurable via the Wi-Fi module to enable a user to remotely transmit commands for at least one of controlling heating of electrical heater, adjusting the predefined vaporization temperature, and disabling the electrical heater.

In some embodiments, the device may include a Bluetooth® module coupled to the control circuit. The control circuit may be remotely configurable via the Bluetooth® module to enable a user to remotely transmit commands for at least one of controlling heating of electrical heater, adjusting the predefined vaporization temperature, and disabling the electrical heater.

In some embodiments, the control circuit may be operable to communicate with a smartphone operating a smartphone application corresponding to the vaporization device. A user may operate the smartphone application to transmit commands for at least one of controlling heating of electrical heater, adjusting the predefined vaporization temperature, and disabling the electrical heater.

In some embodiments, the device may include a speaker disposed within the support unit, the speaker may be electrically coupled with the control circuit.

In some embodiments, the support unit may include an orientation sensor electrically coupled with the control circuit, the orientation sensor may be operable to generate a tilt signal upon determining that the support unit is not positioned in the in-use position, and the control circuit may be configured to disable the electrical heater in response to the tilt signal.

In some embodiments, the device may also include an extract ejector having an extract output port and an extract reservoir fillable with phyto material extract; and an actuator electrically coupled to the first control circuit and mechanically coupled to the extract ejector, the actuator operable to actuate the extract ejector to deposit a predefined volume of phyto material extract from the extract reservoir onto the phyto material contact surface via the extract output port.

In some embodiments, the extract ejector may be a syringe that can be filled with phyto material extract. In some embodiments, the extract ejector can include a plurality of syringes.

In some embodiments, the vaporization device may also include an ambient air input aperture upstream from the first end of the elongated member for receiving ambient air and a mass airflow meter in fluid communication with the first end of the elongated member disposed downstream of the ambient air input aperture. The mass airflow meter may measure a quantity of ambient air passing therethrough and generate initial air flow data based on an initial flow of ambient air passing therethrough. The mass airflow meter may be coupled to the control circuit, and the control circuit may process the initial air flow data and adjust at least one of the predetermined volume of the phyto material extract being deposited per unit of time onto the phyto material contact surface and the predefined vaporization temperature of the phyto material contact surface based on the initial air flow data.

In some embodiments, the device may include a robotic arm electrically coupled with the control circuit and coupled with the actuator, the arm may be usable to adjust the position of the phyto material extract output port to a location proximate the phyto material contact surface.

In accordance with an embodiment described herein, there is provided a vaporization device for vaporizing phyto material. The vaporization device can include a vaporization element. The vaporization element can include a hollow member extending from a first end to a second end opposite the first end, the hollow member defining a vaporization element fluid pathway from a vapor inlet positioned at the first end to a vapor outlet positioned at the second end; a heating element disposed proximate the first end of the hollow member, the heating element defining a phyto material contact surface; and an electrical heater adjacent to the heating element. The vaporization device can also include an inhalation aperture in fluid communication with the vapor outlet. The vaporization device can also include an onboard electrical power source electrically connectable to the electrical heater and a control circuit electrically coupled to the power source. The control circuit may be configured to controllably provide electrical power from the electrical power source to the electrical heater to heat the phyto material contact surface to a predefined vaporization temperature.

In accordance with an aspect of this disclosure, there is provided a method for vaporizing phyto material. The method can include providing an electronic vaporization element having a heating element defining a phyto material contact surface, a hollow member having a first end disposed proximate the heating element and a second end opposite the first end, the hollow member defining a fluid pathway extending from the first end to the second end; coupling the second end of the hollow member to an input port of a vapor processing device having a vapor processing device fluid pathway extending from the input port to an inhalation aperture; mounting a support unit to the vapor processing device, the support unit having a first side and a second side opposite the first surface where the second side of the support unit frictionally engages the vapor processing device such that the vapor processing device is maintainable in an upright position when the support unit is positioned in an in-use position in which the second surface faces substantially upwards, the support unit comprising an electrical power source; depositing phyto material extract onto the phyto material contact surface; and heating the heating element to a predetermined vaporization temperature using electrical power from the electrical power source whereby the deposited phyto material extract is vaporized.

In some embodiments, the method may further include drawing air from the inhalation aperture to cause the vapor and ambient air to flow through the fluid pathway from the first end of the hollow member to the inhalation aperture.

In accordance with an aspect of this disclosure, there is provided a vaporization element for a vaporization device. The vaporization element may include a hollow member having a first end and a second end opposite the first end, the hollow member defining a fluid pathway extending from the first end to the second end, wherein the second end is fluidly engageable with an input port of a vapor processing device; a cylindrical vaporization section, the cylindrical vaporization section having a first inner diameter and a first outer diameter, the cylindrical vaporization section having a vaporization section first end and a vaporization section second end opposite the vaporization section first end, wherein the first end of the hollow member is fluidly coupled with a vaporization section volume defined by the vaporization section first end, vaporization section second end and the first inner diameter; a cylindrical heater section, the cylindrical heater section having a second inner diameter and a second outer diameter, the cylindrical heater section having a heater section first end and a heater section second end opposite the heater section first end, where the second inner diameter, the heater section first end and the heater section second end define a heater section volume within which an electrical heating unit is receivable; and a phyto material contact element having a first side positioned at the vaporization section second end and a second side positioned at the heater section first end, the first side of the phyto material contact element defining a phyto material contact surface.

In some embodiments, the cylindrical heater section and the cylindrical vaporization section may be coaxial.

In some embodiments, the second inner diameter may be greater than the first inner diameter.

In some embodiments wherein the second inner diameter may be approximately equal to the first outer diameter.

In some embodiments, the vaporization element may also include the electrical heating unit positioned within the heater section volume proximate the second side of the phyto material contact element, the electrical heating unit can include a resistive heater positioned adjacent to, or contacting, the second side of the phyto material contact element.

In some embodiments, the electrical heating unit may include a heater housing that is frictionally engageable with an inner surface of the cylindrical heater section.

In some embodiments, the electrical heating unit may further include a heat shield positioned between the resistive heater and the inner surface of the cylindrical heater section.

In some embodiments, at least one of the cylindrical vaporization section and the phyto material contact element may be manufactured from silicon carbide.

In some embodiments, the cylindrical vaporization section and the cylindrical heater section may be coaxial about a first coaxial axis and a cross section of the cylindrical vaporization section and the cylindrical heater section may be in the shape of the letter H.

It will be appreciated by a person skilled in the art that an apparatus or method disclosed herein may embody any one or more of the features contained herein and that the features may be used in any particular combination or sub-combination.

These and other aspects and features of various embodiments will be described in greater detail below.

BRIEF DESCRIPTION OF THE DRAWINGS

For a better understanding of the described embodiments and to show more clearly how they may be carried into effect, reference will now be made, by way of example, to the accompanying drawings in which:

FIG. 5A shows a perspective side view of an example vapor processing device and another example support unit for a vaporization device in accordance with an embodiment;

FIG. 5B shows a top view of the example support unit shown in FIG. 5A;

FIG. 5C shows a perspective side view of the example vapor processing device shown in FIG. 5A mounted to the example support unit shown in FIG. 5A with the support unit in a locked position in accordance with an embodiment;

FIG. 5D shows a top view of the example support unit shown in FIG. 5C in the locked position;

FIG. 6G shows a perspective side view of the example vaporization device shown in FIG. 6A and an another example external control unit in accordance with an embodiment;

FIG. 6H shows a perspective side view of another example support unit having an orientation sensor that may be used with the example vaporization device shown in FIG. 6A in accordance with an embodiment;

FIG. 6I illustrates a perspective side view of another example support unit that may be used with the example vaporization device shown in FIG. 6A in accordance with an embodiment;

FIG. 9A shows a perspective view of another example vaporization device in accordance with an embodiment;

FIG. 9B shows a cross-section of an example vaporization element for the vaporization device show in FIG. 9A in accordance with an embodiment FIG. 9C shows a cut-away side view of an example vaporization element for the vaporization device show in FIG. 9A in accordance with an embodiment;

FIG. 11A shows an exploded partial cut-away view of another example vaporization element in accordance with an embodiment;

FIG. 11B shows a partial cut-away side view of the example vaporization element shown in FIG. 11A;

Figure 1A:
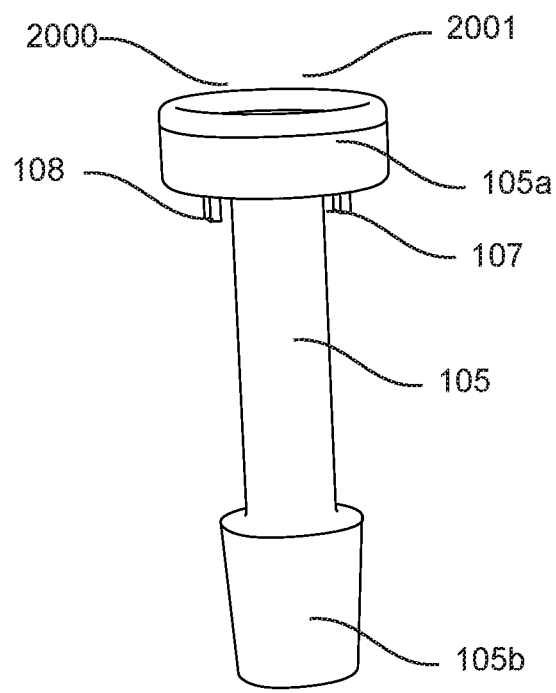
FIG. 1A is perspective side view of a first example vaporization element in accordance with an embodiment.
Figure 1B:
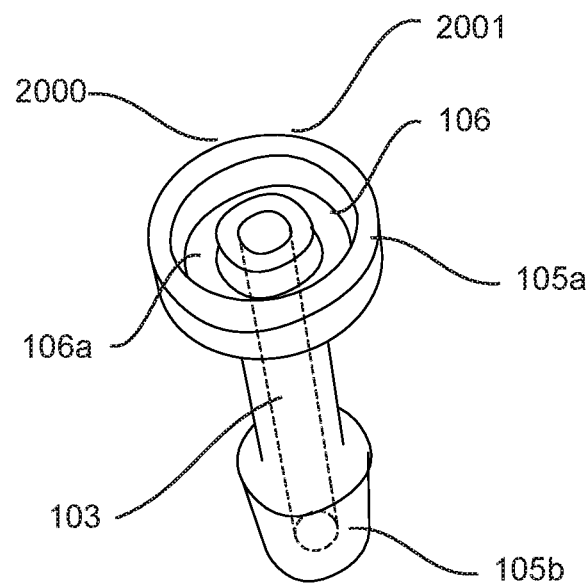
FIG. 1B is a perspective top view of the example vaporization element shown in FIG. 1A.
Figure 1C:
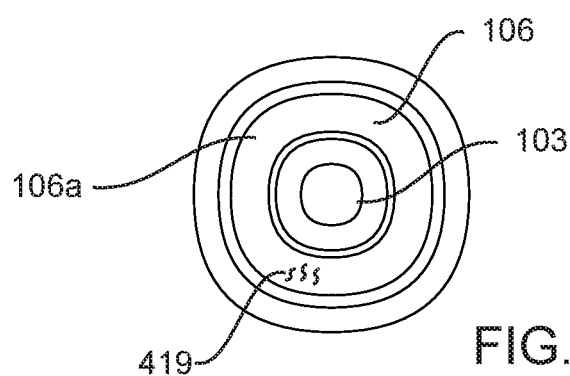
FIG. 1C is a top view of the example vaporization element shown in FIG. 1A.

The drawings included herewith are for illustrating various examples of articles, methods, and apparatuses of the teaching of the present specification and are not intended to limit the scope of what is taught in any way.

DESCRIPTION OF EXAMPLE EMBODIMENTS

Various apparatuses, methods and compositions are described below to provide an example of an embodiment of each claimed invention. No embodiment described below limits any claimed invention and any claimed invention may cover apparatuses and methods that differ from those described below. The claimed inventions are not limited to apparatuses, methods and compositions having all of the features of any one apparatus, method or composition described below or to features common to multiple or all of the apparatuses, methods or compositions described below. It is possible that an apparatus, method or composition described below is not an embodiment of any claimed invention. Any invention disclosed in an apparatus, method or composition described below that is not claimed in this document may be the subject matter of another protective instrument, for example, a continuing patent application, and the applicant(s), inventor(s) and/or owner(s) do not intend to abandon, disclaim, or dedicate to the public any such invention by its disclosure in this document.

Furthermore, it will be appreciated that for simplicity and clarity of illustration, where considered appropriate, reference numerals may be repeated among the figures to indicate corresponding or analogous elements. In addition, numerous specific details are set forth in order to provide a thorough understanding of the example embodiments described herein. However, it will be understood by those of ordinary skill in the art that the example embodiments described herein may be practiced without these specific details. In other instances, well-known methods, procedures, and components have not been described in detail so as not to obscure the example embodiments described herein. Also, the description is not to be considered as limiting the scope of the example embodiments described herein.

The terms "an embodiment," "embodiment," "embodiments," "the embodiment," "the embodiments," "one or more embodiments," "some embodiments," and "one embodiment" mean "one or more (but not all) embodiments of the present invention(s)," unless expressly specified otherwise.

The terms "including," "comprising," and variations thereof mean "including but not limited to," unless expressly specified otherwise. A listing of items does not imply that any or all of the items are mutually exclusive, unless expressly specified otherwise. The terms "a," "an," and "the" mean "one or more," unless expressly specified otherwise.

Embodiments described herein relate generally to vaporization of phyto material and phyto material products. Phyto material products maybe derived from phyto materials such as the leaves or buds of cannabis plants. Derived phyto material products may be referred to by various terms, such as oils, extracts, concentrates, tinctures etc.

For simplicity and clarity, unless otherwise specified, the terms "vaporizing phyto material" or "vaporization of phyto material" (and variants thereof) are used herein as general terms to encompass the vaporization of phyto materials such as leaves or buds as well as the vaporization of derived phyto material products such as extracts.

Phyto material extracts (oils, extracts, concentrates, tinctures etc.) can be derived from phyto materials such as the leaves or buds of cannabis plants. Typically, phyto materials may be leafy while phyto material extracts may have an oily or waxy consistency. These phyto material extracts may be in liquid and/or solid states. Heat can be applied to these phyto material extracts to cause them to boil and/or sublimate and release a vapor.

In some cases, the phyto material products may be derived from plants such as cannabis plants using various processing techniques, which can include additives in the derived products. In other cases, they may be extracted directly e.g. from oils or resins secreted by, or excreted from, plants such as cannabis plants without additional additives.

Various phyto material products derived from plant matter can be vaporized for aromatherapy or therapeutic purposes. For instance, phyto material extracts derived from parts of the cannabis plants, such as the buds and/or leaves, may be vaporized. A user may inhale the cannabis vapor to achieve associated therapeutic effects.

Various methods of vaporizing phyto materials, such as cannabis products, are known. For cannabis oils or extracts, temperatures in the range of about 500 to 700 degrees Fahrenheit may be applied to vaporize these oils or extracts. In many cases, a metal or ceramic heating element may be heated using a torch in order to reach the desired temperature. The heated heating element may then be brought into contact with the extract to generate vapor. This vapor can then be inhaled by a user, sometimes after passing through a cooling channel.

However, it can be difficult to ensure that the heating element is heated to the proper vaporization temperature. Accordingly, the process of heating the heating element tends to be a visual or time based estimate of the proper heating time. This can result in the heating element becoming overheated and potentially burning the extract. When heating is performed by a torch, the phyto material extract may combust instead of being vaporized. For example, the use of a torch may heat the element to over 1000 degrees Fahrenheit, which can result in combustion of the phyto material extract rather than vaporization.

Heating extract to combustion temperatures may generate smoke and other combustion by-products which can then be inhaled by a user from the inhalation aperture. The by-products of combustion can be harmful to a user. Additionally, inhaling smoke and other combustion by-products simply provides a less enjoyable experience to users.

In some cases, vaporization elements may include electrical heating components or heaters. However, these heating components need to be plugged into a wall outlet, resulting in cumbersome devices requiring either lengthy power cables or having limited mobility. These cables can introduce additional dangers into the use of vaporization devices, as users may trip over the cables and fall or cause the vaporization devices to tip over. If the vaporization device is heated, tipping can be a significant fire hazard given the high temperatures involved in vaporizing extracts.

Embodiments described herein generally relate to devices and methods to vaporize phyto material and phyto material extracts. In general, the vaporization devices described herein include a vapor inlet that is arranged to receive extract vapor. The vapor inlet can be coupled to an inhalation aperture by a fluid pathway.

The vaporization device can include a vaporization element that is usable to heat phyto material extracts to a desired vaporization temperature to generate an extract vapor. The vaporization device can define a fluid pathway extending from the vaporization element to an inhalation aperture. The extract vapor can flow through the fluid pathway to the inhalation aperture whereby a user can inhale the vapor. The vapor may be drawn into and through the fluid pathway by a user inhaling via the inhalation aperture.

The vaporization element can include a heating element or phyto material holder. The heating element may be shaped to receive and hold phyto material extract that is to be vaporized.

The vaporization element can also include an electrical heater that can be used to vaporize the phyto material extract. The electrical heater can be arranged to heat the heating element (or at least a portion thereof) which can in turn heat phyto material extract that is positioned on a phyto material contact surface of the heating element.

The vapor inlet can be positioned in close proximity to the phyto material holder. The vaporization element may define a fluid pathway that extends from the vapor inlet to a vaporization element vapor outlet that can be fluidly coupled to the inhalation aperture. In some cases, the vapor outlet may define the inhalation aperture.

The vaporization device may include a vapor processing device between the vapor inlet and the inhalation aperture. In some cases, the vapor processing device may be a static (i.e. not active) processing device.

The vapor processing device can include a filtering portion and/or cooling portion. The fluid pathway may extend through the filtering portion and or cooling portion. Vapor passing through the fluid pathway may then be filtered and/or cooled as it passes through the vapor processing device.

For instance, a vapor processing device with a water trap, such as a water pipe or bong, may be used to provide a combined filtering and cooling portion. The water trap can be used to store water or other similar fluids. The water may serve to filter incoming ambient air and phyto material extract vapor as it propagates through the fluid pathway. When a user inhales from the inhalation aperture, vapor and ambient air can enter the vapor inlet and percolate through the water trap to be inhaled from the inhalation aperture.

To generate extract vapor, a heating element may be coupled to the vapor inlet. The heating element can be heated until it reaches a predefined vaporization temperature. Extract placed in contact with the heating element can be boiled by the heat to generate the extract vapor. As a user inhales from the inhalation aperture (which may be provided by the water pipe), the vapor and ambient air flow through the fluid pathway, are cooled by water in the water trap, and inhaled by the user.

Embodiments described herein may provide vaporization devices that may address the aforementioned deficiencies.

Vaporization Device

The following is a general description of a vaporization device that may be used by itself or in combination with one or more aspects of the disclosure herein, including a vaporization element, a support unit for a vaporization device, and/or a method for vaporizing phyto material. The following description contains various features of a vaporization device that may be used individually or in any combination or sub-combination.

In general, a vaporization device in accordance with embodiments described herein includes a vaporization element. The vaporization element can be used to vaporize phyto material and/or phyto material extract to generate vapor that can be inhaled by a user.

The vaporization element typically includes a heating element with an extract holder portion or phyto material contact element that can be configured to receive phyto material extract. Phyto material extract that is to be vaporized can be positioned in the extract holder portion (e.g. on a phyto material contact surface of the phyto material contact element) to be vaporized.

A heater can be positioned proximate to the extract holder portion. For instance, the heater may be formed as part of the heating element and may be positioned adjacent to, or even as part of (e.g. partially embedded or sintered into), the phyto material contact element. The heater can be configured to heat the phyto material contact element (and thus the phyto material contact surface) to a predefined vaporization temperature. The predefined vaporization temperature can be selected as temperature suitable for boiling the phyto material or phyto material extract to generate a vapor. The predefined vaporization temperature can be selected to vaporize the phyto material without causing the phyto material or extract to combust.

In embodiments described herein, the heater may be an electric heater. For instance, the electric heater may include a resistive heater that generates heat as current flows therethrough. The temperature of the heater may be adjustable to provide a desired vaporization temperature, e.g. by adjusting the level of current flowing through the resistive heater.

The vaporization device also generally includes a fluid pathway that extends from a vapor inlet to an inhalation aperture. The vapor inlet can be positioned proximate to the heating element. In particular, the vapor inlet may be positioned proximate to, and in fluid communication with, the phyto material contact surface. The vapor inlet may be positioned to capture some or all of the vapor released when the phyto material extract is vaporized. The inhalation aperture can be used by an individual to inhale the vapor received from the vapor inlet which can be drawn through the fluid pathway.

The fluid pathway may include one or more intermediate portions between the vapor inlet and the inhalation aperture. For instance, the fluid pathway may include a filtering section and/or a cooling section. The filtering section may filter the vapor (and ambient air) passing through the fluid pathway before it reaches the inhalation aperture. Filtering the vapor may remove particulate matter that was entrained with the vapor as it entered the vapor inlet.

The fluid pathway may also include an additional cooling section. The cooling section generally refers to a portion of the fluid pathway providing heat exchange between the fluid (i.e. vapor and ambient air) in the fluid pathway and other fluids (such as ambient air or water) adjacent to, or positioned within, the fluid pathway. The cooling section may reduce the temperature of the vapor to a temperature more suitable for inhalation.

In some cases, a combined filtering and cooling section may be provided. For example, the vaporization device may include a water trap positioned in the fluid pathway between the vapor inlet and the inhalation aperture. The water trap may remove particulate matter from the vapor and air passing through the fluid pathway. The water trap can also cool the vapor passing therethrough.

In some embodiments, the filtering and/or cooling sections may be provided by a separate vapor processing device. The vapor processing device can be coupled to the vaporization element. For example, a water pipe may be used as a vapor processing device.

In some embodiments, the vaporization element may include filtering and/or cooling sections. For instance, the vaporization element may include an elongated member defining the fluid pathway. The elongated member may cool the vapor as it passes therethrough because of heat transfer between the vapor and ambient air around the elongated member. In some cases, a filtering component such as a screen may be placed in the fluid pathway to filter vapor passing therethrough.

In some embodiments, the vaporization device may also include various power and/or control components. For example, the vaporization device may include an onboard power source. The power source may include one or more batteries. The onboard power source may be used to provide current for the electric heating element. The onboard power source may also power other electric and/or electronic components of the vaporization device, such as control circuitry that may be included in the vaporization device. In some cases, the onboard power source and/or electronic components may be provided as part of a vaporization device support unit.

Figure 2A:
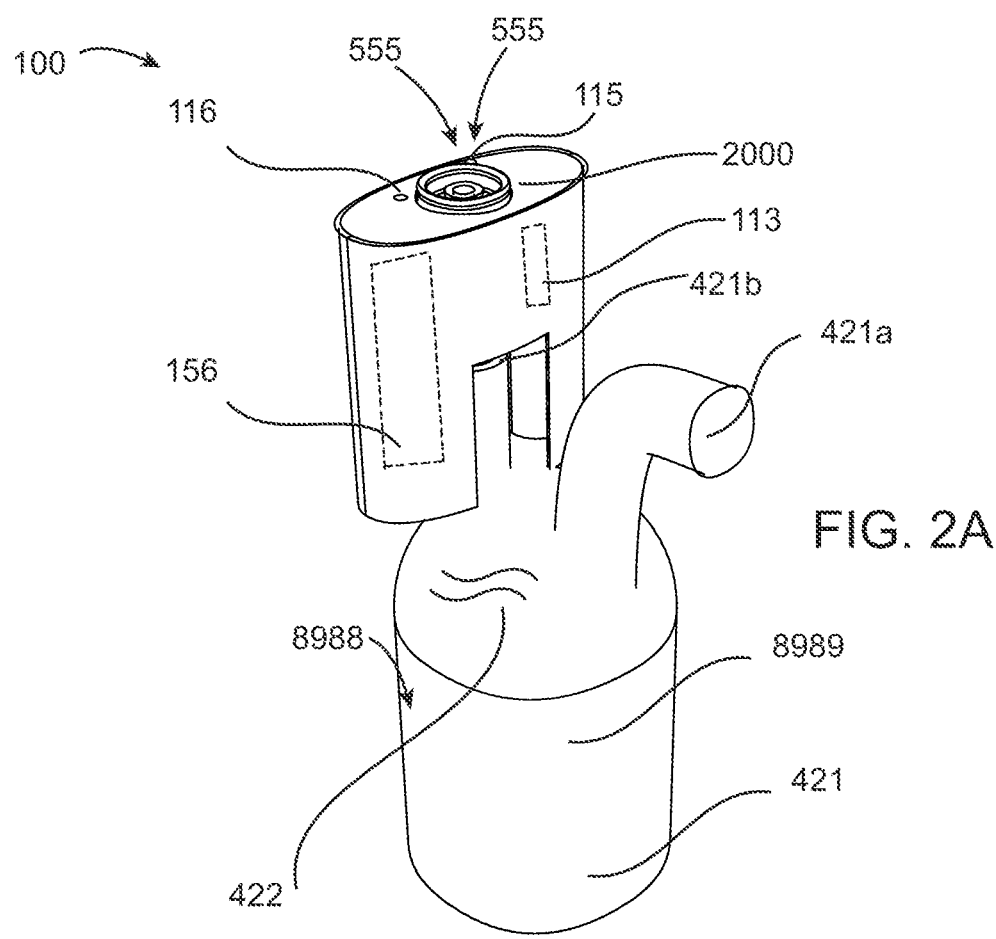
FIG. 2A is a perspective view of an example vaporization device in accordance with an embodiment.
Figure 2B:
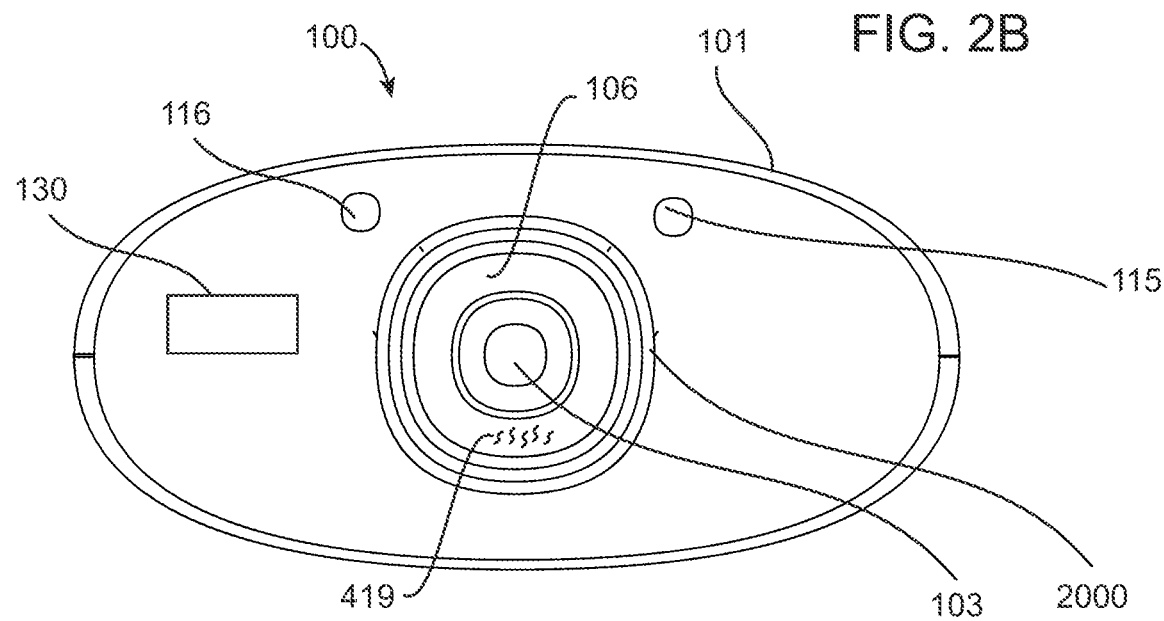
FIG. 2B is a top view of the example vaporization device shown in FIG. 2A.

FIG. 2A illustrates an example of a vaporization device 100. Vaporization device 100 may be used to vaporize phyto material and/or phyto material extract in accordance with an embodiment. The vaporization device 100 can include a vaporization element 2000 and a support unit 101.

As shown in FIG. 2A, the vaporization element 2000 can be coupled to a vapor processing device such as a water pipe 421. The vapor processing device may be used to filter and/or cool vapor generated by the vaporization device 100 before it is inhaled by a user.

In some embodiments described herein, the vapor processing device 421 may be provided as part of the vaporization device 100. Alternatively, the vapor processing device may be provided separately and may be fluidly engageable with the vaporization device 100.

Figure 2C:
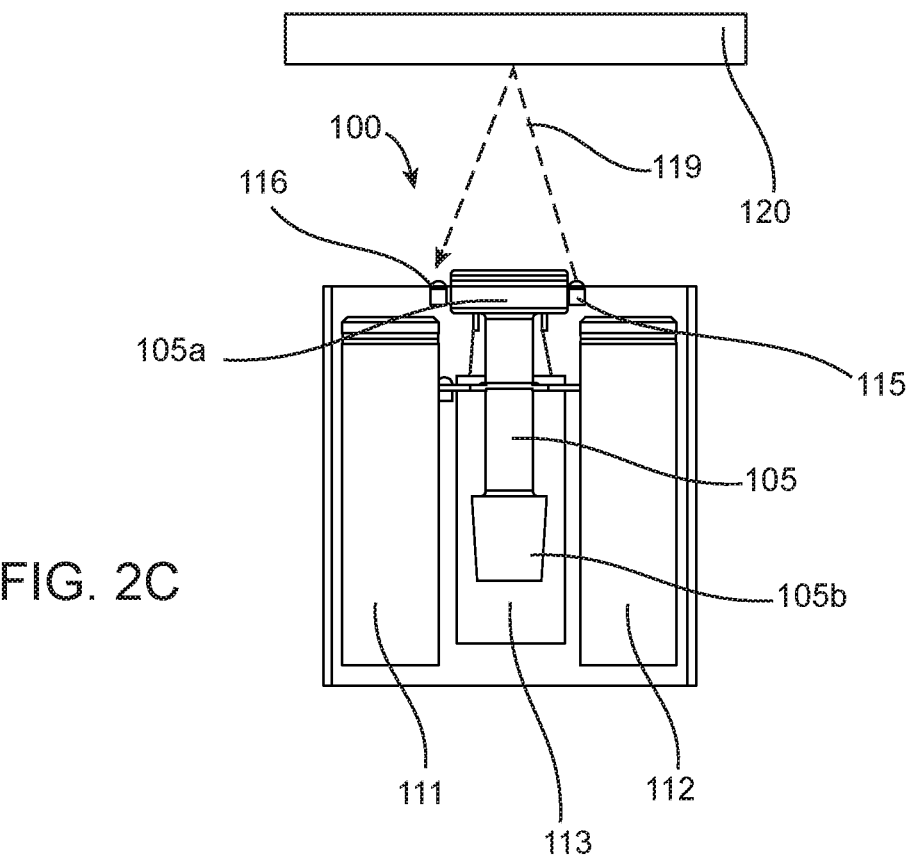
FIG. 2C is a partial cut-away front view of the example vaporization device shown in FIG. 2A in an open position.
Figure 2D:
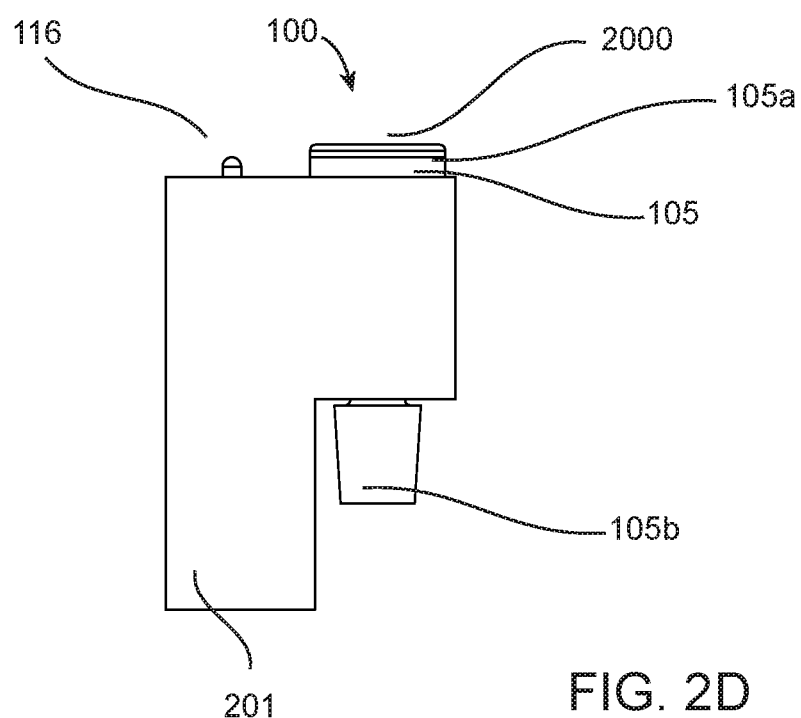
FIG. 2D is a side view of the example vaporization device shown in FIG. 2A.

As shown in FIG. 2D, the vaporization device 100 can include a vaporization element vapor outlet 105b. The vapor processing device such 421 can include a vapor input port (input port 421b) that can be fluidly coupled to the vaporization element vapor outlet 105b. The input port 421b can be fluidly coupled to the vapor outlet 105b to define a continuous fluid pathway between the vaporization element 2000 and the vapor processing device 421.

The vapor processing device 421 can define a processing device fluid pathway 8989 that extends from the vapor input port 421b to a vapor output port 421a. The vapor output port 421a can be configured as an inhalation aperture. A user may inhale vapor generated by the vaporization device 100 using the inhalation aperture 421a.

In some embodiments, the vapor processing device 421 may be omitted. In such embodiments, the inhalation aperture may be provided by, or coupled directly to, vapor outlet 105b.

The vapor processing device 421 can include one or more filtering sections and/or cooling sections. For example, as shown in FIG. 2A the water pipe 421 can include a water trap section 8988. The water trap section 8988 can be positioned in the processing device fluid pathway 8989 between the vapor input port 421a and the vapor output port 421b. The water trap 8988 can house water or another similar liquid, Vapor from the vaporization element 2000 can pass through the water in water trap 8988 as it flows from the input port 421b to the inhalation aperture 421a.

The water in water trap 8988 may remove particulate entrained in the vapor 422 flowing therethrough. This may reduce or eliminate contaminants from the vapor 422 inhaled by a user. This may provide the user with a cleaner, more enjoyable experience.

The water trap 8988 may also cool the vapor 422 flowing therethrough. The vapor 422 may be generated by heating the phyto material extract 419 to temperatures that may be uncomfortable or even painful for a user to inhale. Accordingly, the cooling pathway section provided by the water trap 8988 in this example may reduce the temperature of the vapor to a temperature that may be more comfortable (and safe) for inhalation.

The water trap 8988 may also infuse moisture into the vapor 422. This may provide a more comfortable vapor for inhalation by a user.

As mentioned, vaporization device 100 includes a vaporization element 2000. Various examples of vaporization elements that may be used in embodiments herein are described in further detail herein below with reference to FIGS. 1A-1I, 4C, 6C, 7A-7H, 9A-9C, 10A-10I, 11A-11B, and 12A-12C.

The vaporization element 2000 generally includes an extract holder portion or heating element 106. The extract holder portion can receive phyto material extract 419 to be vaporized. A heater, such as resistive heater 155, can be positioned proximate the extract holder portion 106. The heater 155 can be used to heat the extract 419 positioned in the extract holder portion 106 (i.e. by heating the extract holder portion 106).

The vaporization element 2000 can define a vaporization element fluid pathway 103. The vaporization element fluid pathway extends from a first end 105*a* to a second end 105*b*.

The first end 105*a* of the fluid pathway 103 may also be referred to as a vapor inlet. The first end 105*a* of the fluid pathway 103 can be positioned proximate the heating element 106. When the heating element 106 is used to heat extract, the vapor given off can enter the fluid pathway 103 via the vapor inlet 105*a*. This vapor may then pass through fluid pathway 103 to the vapor outlet 105*b*.

In the example vaporization device 100, the fluid pathway 103 of the vaporization element 2000 can be formed by an elongated member 105. The elongated member 105 may have a hollow central portion that defines the fluid pathway 103. Various configurations of the vaporization element 2000 and vaporization device fluid pathway 103 are described in further detail herein below.

As shown in FIG. 2A, the vaporization element 2000 can be coupled to the vapor processing device 8989, with the vapor outlet 105*b* fluidly coupled to the processing device vapor inlet 421*b*. Extract vapor can pass through the fluid pathway 103 and into the vapor processing device 421 via the vapor outlet 105*b* and vapor inlet 421*b*. The extract vapor may then pass through the processing device pathway portion 8989 to inhalation aperture 421*a* where it can be inhaled by a user.

Vaporization device 1000 can include a support unit 101. The support unit 101 may define a housing of the vaporization device 1000. In some embodiments, such as the example vaporization device 1000, the vaporization element 2000 can be disposed within the housing of support unit 101.

The housing of support unit 101 may frictionally engage the vaporization element 2000. This may maintain the vaporization element 2000 within the housing. For instance, the housing of support unit 101 may frictionally engage the elongated hollow member 105 proximate where the second end 105*b* of the elongated hollow member 105 is engageable with the water pipe input port 421*b*.

In some embodiments, the vaporization device 100 may also include an on-board power source 156. The on-board power source 156 may be used to power the heating element 106. The on-board power source 156 may be provided by the support unit 101. For instance, the power source 156 may be enclosed within the housing of support unit 101. As shown in FIG. 2C, the on-board power source 156 may include one or more batteries 111, 112.

The electrical power source 156 can be electrically coupled to the resistive heater 155. A pair of electrical contacts or leads 107/108 may extend from the resistive heater 155. The electrical contacts 107/108 may be electrically connected to the power source 156. For example, wires extending from the electrical power source 156 can be electrically connected, directly or indirectly, to contacts 107/108. This may enable the electrical power source 156 to provide power to the resistive heater 155.

The power source 156 can provide electrical power through resistive heater 155 to heat the resistive heater 155. Heating of the resistive heater 155 can impart thermal energy to the heating element 106. The heating element 106 can in turn heat the phyto material extract positioned on the phyto material contact surface.

In some embodiments, the vaporization device 100 may be configured to use power from an external power source, such as a wall power outlet. The vaporization device 100 may include a power coupling for such an external power source. In some such cases, the onboard power source 156 may be omitted. In other cases, the power coupling may be provided in addition to the onboard power source 156.

As shown in FIG. 2A, the heating element 106 may define a recess or well in which the extract 419 can be positioned. This may facilitate holding the extract 419 on the heating element 106 during vaporization.

In some cases, the heating element 106 can be shaped to correspond to the resistive heater 155. This may increase the surface area of the extract that is heated. This may also provide a more effective and consistent vaporization of the extract 419.

For example, the resistive heater 155 may extend substantially across the bottom side of the heating element 106 opposite the side on which the extract 419 is to be deposited. Alternatively, the heating element 106 may be shaped to substantially surround the resistive heater 155 as shown, for example, in FIG. 4C. In some cases, the resistive heater 155 may be embedded or partially embedded into the heating element 106.

The heating element 106 may include a phyto material contact element. The phyto material contact element may have a first side 106*a* that is positioned to contact the phyto material extract 419. In some cases, the phyto material contact element may be provided as an integral base of the heating element 106. The first side 106*a* of the phyto material contact element can define a phyto material contact surface 106*a*. The extract 419 may rest on the first side 106*a* when positioned for vaporization.

The resistive heater 155 may be positioned proximate to, or in contact with, the second side 106*b* of the phyto material contact element. As current is provided through the resistive heater 155, the thermal energy (i.e. the heat) generated by the resistive heater 155 can be transferred to the heating element 106. A portion of the thermal energy can be transferred through the phyto material contact element to the first side 106*a* that contacts the phyto material extract 419.

In some cases, a portion of the thermal energy from the resistive heater 155 can also be transferred to the walls of the heating element 106. This may further increase the surface area of the heating element that contacts and heats extract 419.

As shown in the example of FIGS. 2A-2D, the heating element 106 may be annular. Thermal energy from the resistive heater 155 can be transferred through the base of the heating element 106 (the phyto material contact element) and to the inner and outer sidewalls of the heating element 106. The extract 419 positioned in the heating element 106 may then be vaporized in response to the heat applied from the phyto material contact surface 106*a* as well as the sidewalls of the heating element 106.

The vapor 422 generated from the extract 419 can pass into the vapor inlet 105*a* of the fluid pathway 103. Ambient air 555 may mix with the vapor 422 as it enters the fluid pathway 103. This combination of vapor 422 and ambient air 555 can travel through the vaporization element fluid pathway 103 and the processing device pathway 8989 to reach the inhalation aperture 421*a*. The combined vapor and ambient air can then be inhaled by a user.

As the vapor 422 and ambient air 555 travel through the fluid pathway they can be cooled as they contact the inner walls of the hollow member 105. Similarly, the water trap in water pipe 421 may serve to cool the vapor and ambient air passing therethrough. This may reduce the heat of the vapor 422 to a more comfortable temperature for inhalation.

In some embodiments, the vaporization device 100 can also include a control circuit 113. The control circuit 113 can be coupled to the on-board power source 156. The control circuit 113 can be configured to control the current being provided from the onboard power source 156 to the resistive heater 155.

In some cases, the vaporization device 100 may also include a temperature sensor 170. The temperature sensor 170 may be used to determine the level of heat being provided to phyto material extract positioned on the phyto material contact surface. The temperature sensor 170 may transmit a temperature signal to the control circuit 113. The control circuit 113 can use the received temperature signal to perform various operations, such as determining the level of power to provide to the resistive heater 155 or determining whether the heating element 106 has reached the predetermined vaporization temperature.

In some cases, the temperature sensor 170 can be positioned proximate to the second side 106b of the phyto material contact element. The temperature sensor 170 may be positioned to contact the second side 106b. The control circuit 113 may then determine the temperature of the phyto material contact surface 106a based on the temperature signal indicating a temperature of the second side 106b.

In some embodiments, the vaporization device 1000 may include a temperature sensor that may detect the temperature of the phyto material contact surface 106a directly. For example, a thermal imaging sensor may be used to measure the temperature of the phyto material contact surface 106a.

The control circuit 113 can determine the current temperature of the heating element 106 based on the received signal(s) received from the temperature sensor 170. The control circuit 113 may then determine the electrical power needed to heat the resistive heater 155 to the desired temperature. The control circuit 113 may set or adjust, if necessary, the power being provided to the resistive heater 155 so that the contact surface 106a of the holder portion can be heated to the desired vaporization temperature.

Typically the predefined vaporization temperature may be defined between about 300 degrees Fahrenheit and 700 degrees Fahrenheit. The predefined vaporization temperature may vary depending on whether the vaporization device 100 is used for phyto materials or phyto material extracts. In general, the predetermined vaporization temperature will be greater for phyto material extracts than for phyto material, in the form of leaf. For instance, phyto materials may have a predetermined vaporization temperature less than 440 degrees Fahrenheit.

Figure 8:
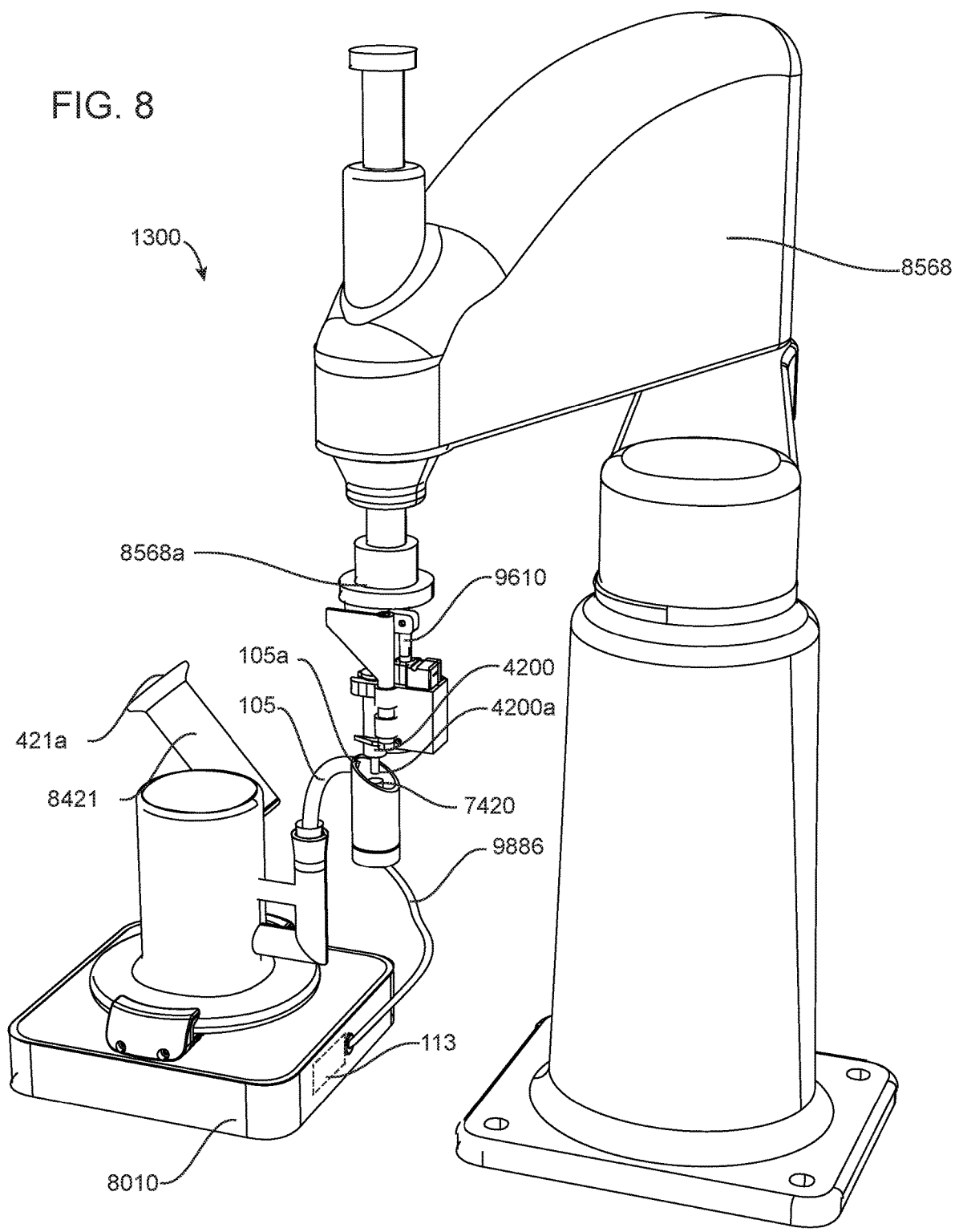
FIG. 8 shows a perspective side view of another example vaporization device with an example dose control apparatus in accordance with an embodiment.

The control circuit 113 may also determine that the heating element 106 (or at least phyto material contact surface 106a) has been heated to the predetermined vaporization temperature. In such cases, the control circuit 113 may generate an output signal indicating that extract can be positioned on the phyto material contact surface 106a. For example, the control circuit 113 may adjust the color of an LED or LED display to indicate that the predetermined vaporization temperature has been reached. In other cases, the control circuit 113 may enable an extract insertion apparatus (see e.g. FIGS. 6L and 8) to deposit extract on the phyto material contact surface 106a when the predetermined vaporization temperature has been reached.

The vaporization devices described herein may include various types of user interfaces. In the example shown in FIGS. 2A-2D, an example infrared interface unit is shown. The example infrared interface unit of vaporization device 2000 can include an infrared transmitter 115 that is exposed by the housing of support unit 101. The example infrared interface unit of vaporization device 2000 can also include an infrared receiver 116 exposed by the housing of support unit 101. In some cases, a combined transceiver may also be used. As shown in FIG. 2C, the infrared transmitter 115 and infrared received 116 may protrude above the surface of the housing of support unit 101.

Each of the infrared transmitter 115 and infrared receiver 116 can be coupled to control circuit 113. The infrared transmitter 115 can emit an infrared signal 119 into a region near the vaporization device 100. The infrared signal 119 may be reflected by an object 200 and transmitted back towards the vaporization device 100 and infrared receiver 116. The detection of the infrared signal 119 by receiver 116 can operate as an activation signal to initiate heating of the resistive heater 155. That is, in response to the control circuit 113 determining that receiver 116 has detected the infrared signal 119, the control circuit 113 can enable current to flow through the resistive heater 155 to heat the heating element 106 to the vaporization temperature.

For instance, the object 120 may be a user's hand. A user may place or wave their hand over the top of the vaporization device 100 to cause the infrared signal 119 to be reflected to receiver 116 and activate the heating element 106.

Referring now to FIGS. 3A-3J, shown therein is another example embodiment of a vaporization device 1000. In the example shown, the vaporization device 1000 includes a vaporization element 2000, a support unit 1001 and a vapor processing device 421. A fluid pathway can be defined extending from a vapor inlet 105a to an inhalation aperture 421a.

Extract 419 can be positioned in the heating element 106 of the vaporization element 2000 and vaporized. The vapor 422 (and some ambient air) can then pass through the fluid pathway 103 defined by vaporization element 2000, into the water pipe 421 via input port 421b, and pass through the water pipe 421 to inhalation aperture 421a. As the vapor 422 passes through the water pipe 421 it can be filtered and/or cooled by water held within the processing device pathway portion 8989 before being inhaled by a user.

The support unit 1001 can also include a securement mechanism for securing the vapor processing device 421 to vaporization device 1000. Various examples of support unit securing mechanisms are described in further detail herein below. The support unit securing mechanisms can be used to fasten a processing device such as a water pipe 421 to the support unit 1001. This may ensure that the water pipe 421 remains in position to facilitate vaporization using the vaporization element 2000, particularly when the vaporization element 2000 is coupled to support unit 1001.

For instance, a frictional engagement mechanism may be used to secure the bottom portion of the processing device 421 to the support unit 1001. As exemplified in FIG. 3B, the frictional engagement mechanism may be in the form of an adjustable clamp 1002.

The vaporization element 2000 can include an electrical heater, such as a resistive heater 155. As mentioned above, embodiments of the vaporization devices described herein may include an onboard electrical power source. For instance, the support unit 1001 can include an onboard electrical power source 156 that can be used to power the vaporization element 2000. Accordingly, the vaporization element 2000 can be electrically coupled to the support unit 1001 by a power coupling 2000b.

The vaporization element 2000 can also be electrically coupled to a vaporization device control circuit 113. In the vaporization device 1000, the control circuit 113 may be housed in the support unit 1001.

A connector cable 2000b can be used to electrically couple the vaporization element 2000 to the support unit 1001. In some cases, the connector cable 2000b may be provided as a separate component from the vaporization element 2000 and the support unit 101. Alternatively, the connector cable 2000b may be integral with the support unit 101 and engageable with a vaporization element 2000. Alternatively, the connector cable 2000b may be omitted, e.g. in embodiments where the vaporization element 2000 and support unit 101 are integrated (see e.g. FIGS. 2A-2D).

The vaporization element 2000 and support unit 1001 can each include connector ports that correspond to the connector cable 2000b. The connector ports may enable various signals (e.g. power, control, sensor etc.) to be transmitted using cable 2000b.

For instance, the vaporization element 2000 can include a coupling port 2000c that provides electrical coupling to power the resistive heater 155. The coupling port 2000c can include couplings to electrical contacts 107/108 that provide power to the resistive heater 155.

The coupling port 2000c can also provide additional coupling to allow sensors signals, such as temperature sensor signals, to be transmitted to the control circuit 113 via connector cable 2000b. For instance, the coupling port 2000c can include a temperature signal output port 170a coupled to temperature sensor 170.

In some cases, the connector cable 2000b can include magnetic couplings at one or both ends. Alternatively, the connector cable 2000b may have mechanical couplings at one or both ends.

Figure 3A:
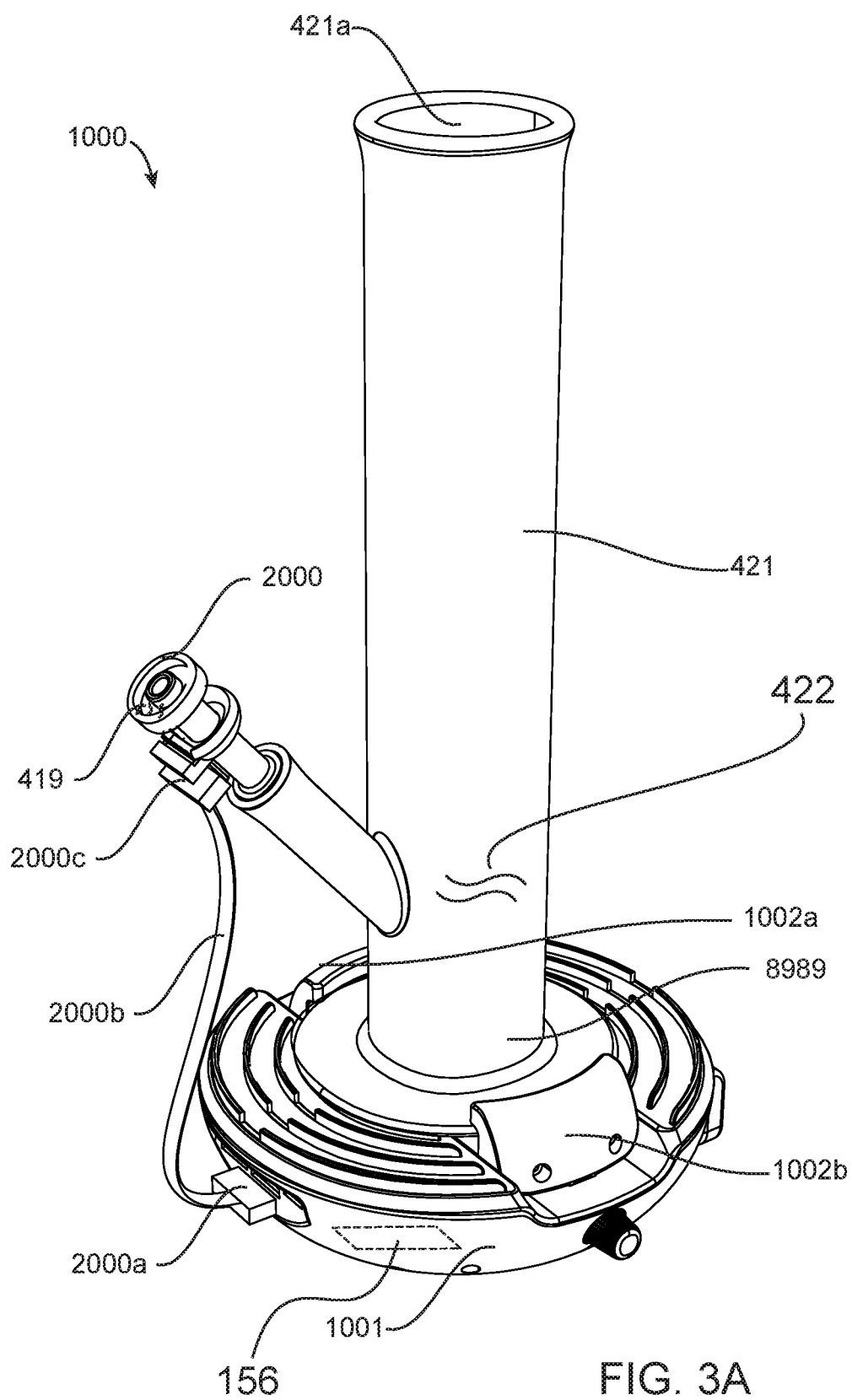
FIG. 3A is a perspective top view of another example vaporization device in accordance with an embodiment.
Figure 3B:
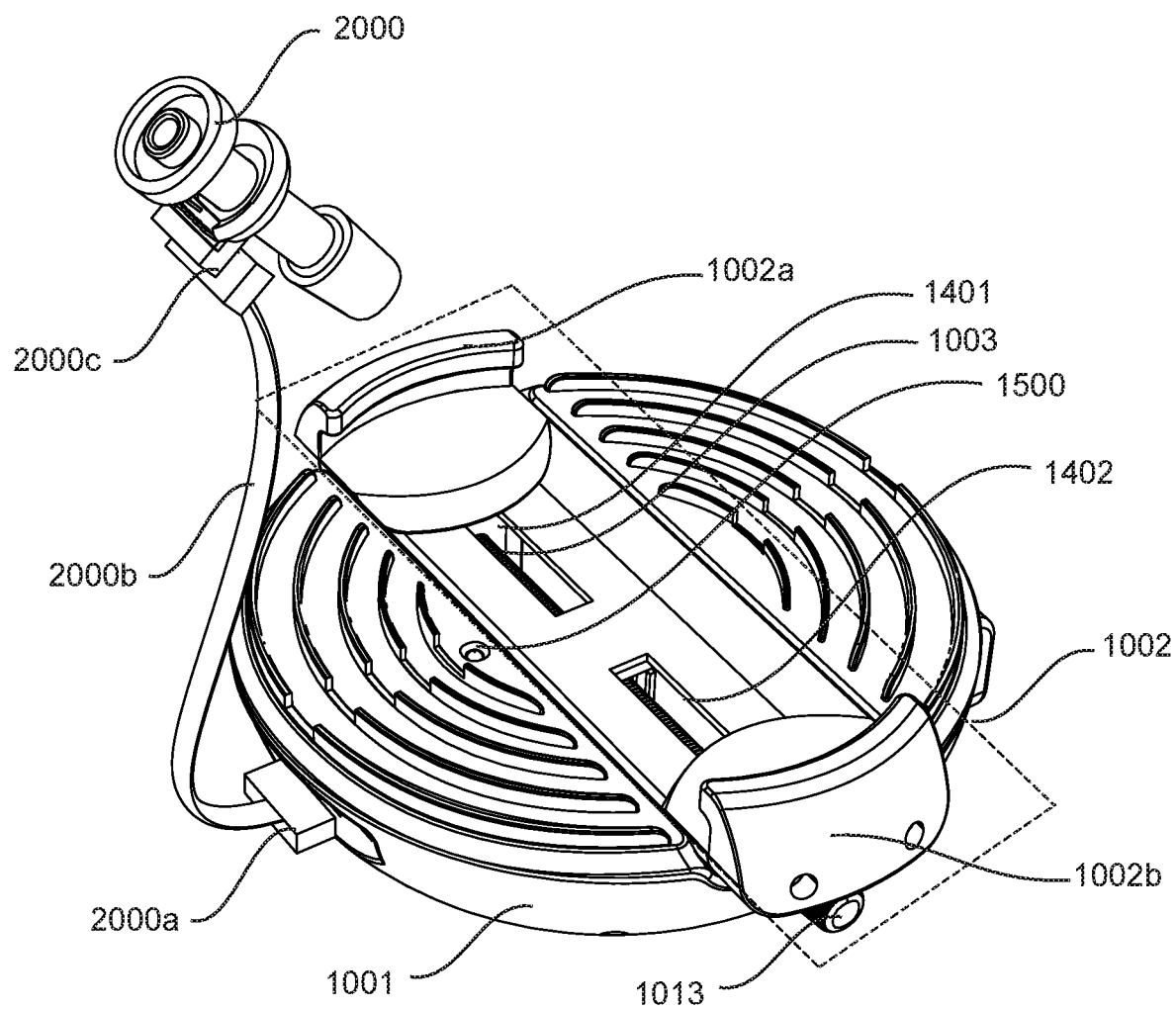
FIG. 3B is a perspective top view of an example vaporization element and example support unit that may be used with the vaporization device shown in FIG. 3A in accordance with an embodiment.

Magnetic couplings may secure the connector cable 2000b to the vaporization element 2000 and/or the support unit 1001. For example, FIG. 3J illustrates a pair of magnets 1974a positioned on a vaporization element end of the connector cable 2000b. The vaporization element 2000 can include a correspond pair of magnets 1974b. The magnets 1974a and 1974b can be used to secure the connector cable 2000b to the vaporization element 2000.

In some cases, the polarity of the magnets in magnet pairs 1974a and 1974b can be arranged to ensure that the connector cable 2000b can be secured only in the proper connection orientation. This can further ensure that the proper electrical coupling between the vaporization element 2000 and the control circuit 113 is provided.

In some cases, the user interface of vaporization device 1000 1001 may include a temperature indicator. For example, the vaporization device 1000 may include a display showing a numerical temperature value or a temperature status with readings such as "heating" and "ready".

In some cases, the temperature indicator may represent the temperature of the heating element 106 using various colors. For example, the vaporization device 1000 may include a multi-colored interface component. The multi-colored interface component may be in the form of a multi-colored LED 1500. As shown in FIG. 3B, the LED 1500 may be provided by the support unit 1001. The LED 1500 can be exposed by the housing of support unit 1001 and visible to a user of vaporization device 1000.

The LED 1500 can be arranged within the support unit 1001 to direct light towards a vapor processing device such as water pipe 421 that is secured to the support unit 1001. This may increase the visibility of the light of LED 1500, for instance as it passes through and is reflected by the processing device 421 and any water that may be retained therein. As shown in FIG. 3B, the LED 1500 can be positioned below the surface of the support unit 1001 that is intended to receive the vapor processing device.

The LED 1500 can be electrically coupled to the control circuit 113. The control circuit 113 may control the LED 1500 to provide a status signal indicating the current status of the vaporization device 1000.

In some embodiments, as shown in FIG. 5D for example, a LED display 1501 may be provided that includes a plurality of three color light emitters. The plurality of LEDs may arranged in a pattern, such as a two dimensional matrix. The LED display may be electrically coupled with first control circuit 113 and operable to illuminate the water pipe. Additionally or alternatively, one or more laser light emitters may be usable to illuminate the water pipe 8421. Such light emitting components may transmit light to the water pipe 8421 where it may be reflected and/or refracted to generate a changeable visual display.

The control circuit 113 may change the color of LED 1500 to provide a status signal indicative of the temperature of the vaporization element 2000 (e.g. as identified from temperature signals received from the temperature sensor 170). For example, the LED 1500 may have a blue color (indicating that the heating element 106 has not yet reached the vaporization temperature) when a temperature of the resistive heater 155 is around 200 degrees Fahrenheit and transition to a red color when the temperature of the resistive heater 155 has substantially reached the vaporization temperature, e.g. around 600 degrees Fahrenheit. In some cases, the LED 1500 may be a three colored LED (e.g. red, green, blue).

As will be appreciated, various different colors and transitions may be used to indicate the state of the vaporization device 1000. For instance, the control circuit 113 may also control the LED 1500 to provide a status signal indicating a power status of the onboard electrical power source 156.

Figure 3C:
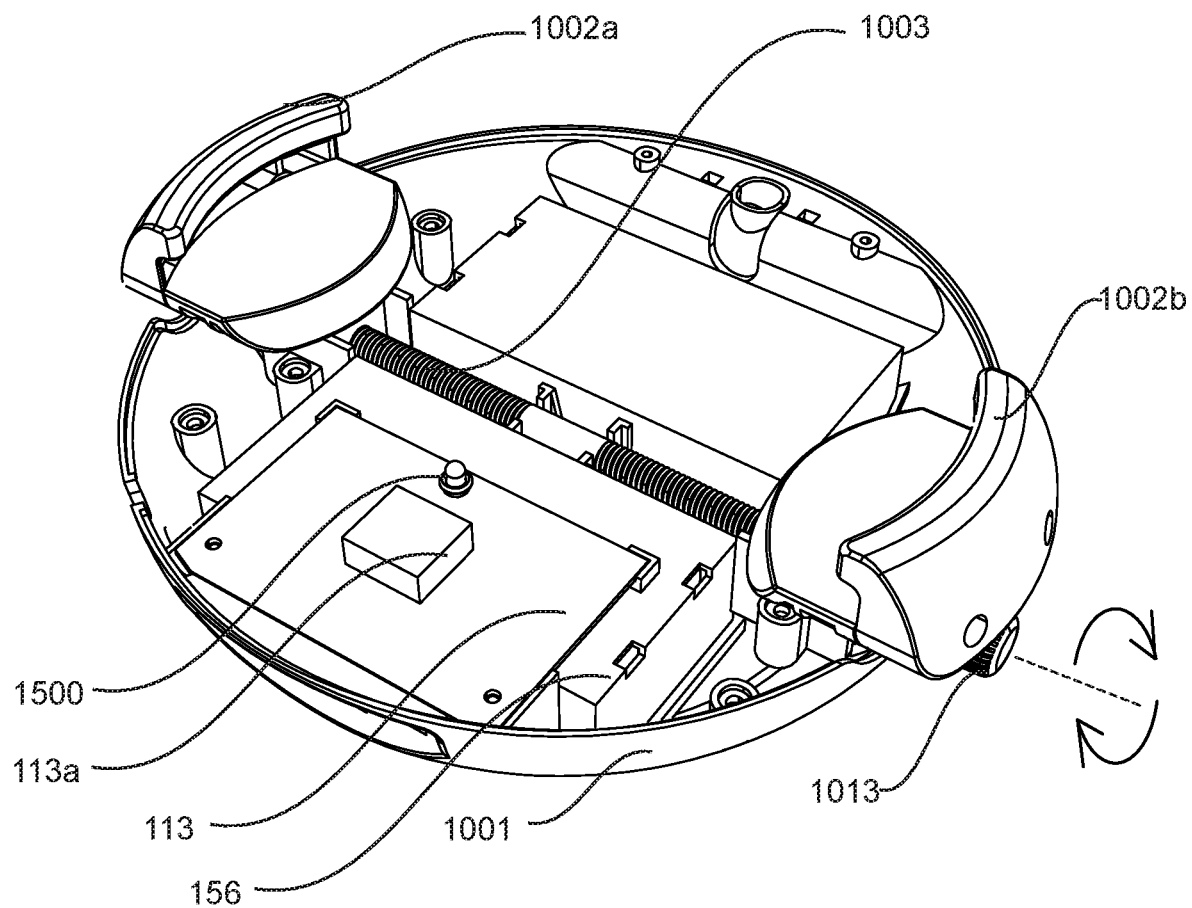
FIG. 3C is a perspective cut-away top view of the example support unit shown in FIG. 3B.

As shown in the example of FIG. 3C, the control circuit 113 can include a processing component 113a. The processing component 113a can be used to process incoming signals, such as temperature signals from the vaporization element 2000 and/or power level signals from the onboard electrical power source 156. The processing component 113a can also determine the level of power to provide to the resistive heater 155. The processing component 113a can also control the flow of current from the power source 156 to the contacts 107/108 of the vaporization element 2000 to controllably heat the resistive heater 155.

Figure 3D:
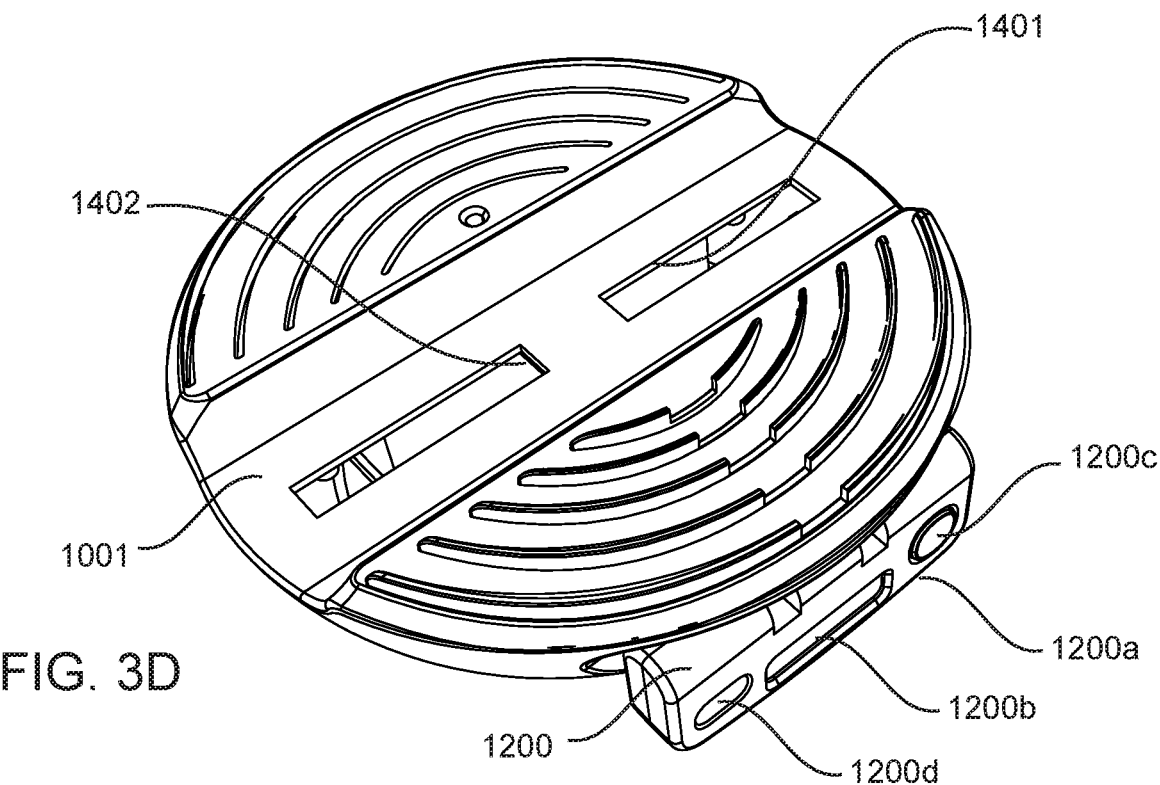
FIG. 3D is a perspective top view of the example support unit shown in FIG. 3B with a control panel in a first position.
Figure 3E:
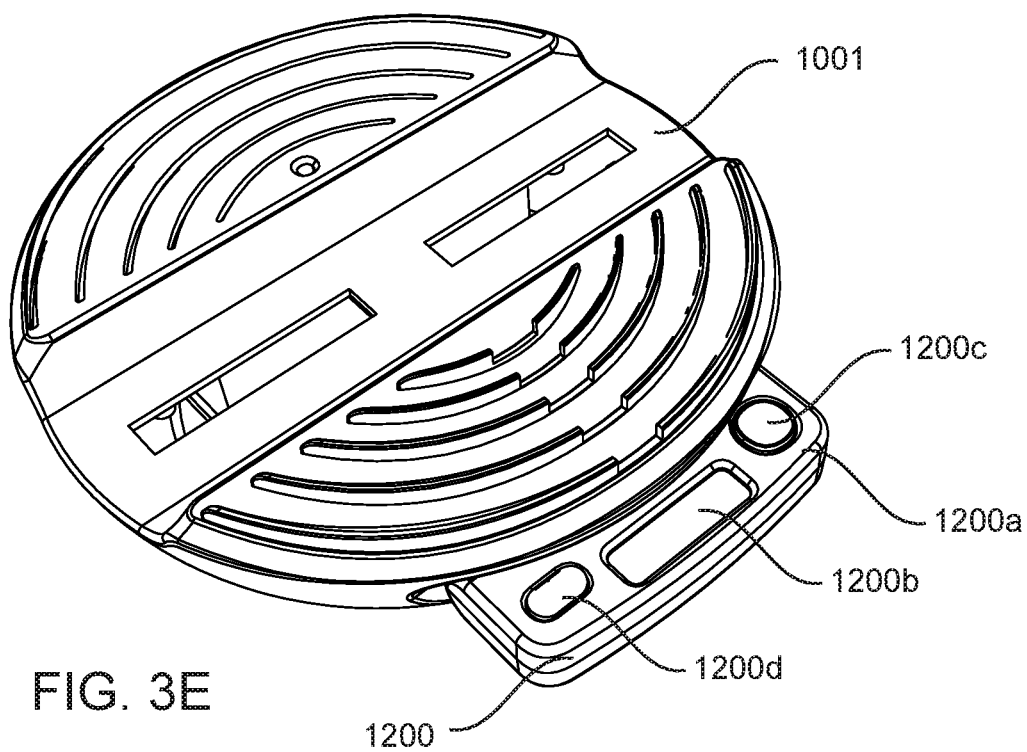
FIG. 3E is a perspective top view of the example support unit shown in FIG. 3B with the control panel in a second position.

In some cases, the user interface unit of the vaporization device 1000 may include a control panel 1200 (see e.g. FIGS. 3D and 3E). The surface 1200a of control panel 1200 may include various user inputs, such as input buttons 1200c and 1200d. The control panel 1200 may also include an output interface, such as display 1200b.

The display 1200b may be implemented using an OLED display screen or an LCD display for example. In various embodiments vaporization device 1000 may include display 1200b in addition to, or in place of, status indicator 1500.

The display 1200b can be used to display status information indicating the status of various components of the vaporization device 1000. The display 1200b can be coupled to control circuit 113. The control circuit 113 can define the status information to be shown on display 1200b. For example, the display 1200b can display a temperature status indicating the temperature of the vaporization element 2000. The display 1200b may also show other status indicators, such as a power level of the onboard power source 156.

The display 1200*b* may also provide other status information regarding the configuration of the vaporization device 1000. For instance, the control circuit 113 may determine whether the vaporization element 2000 is currently coupled to the control circuit 113. The display 1200*b* may then provide a connection status indicator that identifies whether the vaporization element 2000 is correctly coupled to the control circuit 113.

The user inputs on control panel 1200 can include an activation button 1200*c*. The activation button 1200*c* can be coupled to the control circuit 113. The activation button 1200*c* can be used to enable/disable operation of the control circuit 113. In other words, the activation button 1200*c* may operate as an on/off switch.

The user inputs on control panel 1200 can also include a temperature setting input 1200*d*. The temperature setting input 1200*d* can be electrically coupled to the control circuit 113 to provide user inputs adjusting the vaporization temperature to be applied to the vaporization element 2000.

The vaporization device 1000 may have a range of vaporization temperatures that can be selected by a user. For instance, the vaporization temperatures may range from about 100 degrees Celsius to 400 degrees Celsius. A user may wish to adjust the vaporization temperatures, for instance, when vaporizing phyto material rather than phyto material extracts (or vice versa) using the vaporization device 1000. Users may also adjust the vaporization temperatures based on personal preference. The user interface unit may provide input/output components that enable the user to adjust the vaporization temperature.

As in the example shown, the temperature setting input 1200*d* can be configured as a rocker button. As will be appreciated, various other types of user interfaces may be used, such as touchscreen interfaces. Similarly, various other button configurations may be used, such as having multiple buttons to provide temperature setting input 1200*d*.

The display 1200*b* may also provide various configuration settings for the vaporization device 1000. For instance, auto shut-off times and other settings may be adjusted by a user e.g. through input buttons 1200*c* and 1200*d* or another user interface such as a touchscreen or mobile application.

In some cases, the user interfaces may also include remote input and/or output interfaces. For instance, the vaporization device 1000 may be wirelessly coupled with a smartphone or other device that can be used to provide the user interfaces.

For example, the vaporization device 1000 may include a wireless communication module 113*w* (see e.g. FIG. 6G). For instance, the wireless communication module 113*w* can be implemented to support Wi-Fi communication. The wireless communication module 113*w* may be provided as part of the support unit 1001 or may be coupled to the support unit 1001 using the connector ports.

The wireless communication module 113*w* can be coupled to the control circuit 113. The wireless communication module 113*w* may enable the control circuit 113 to communicate wirelessly with other devices, e.g. using a local area network or another network such as the internet.

In some cases, the vaporization device 2000 may include a Bluetooth® module 113*x* to enable the control circuit 113 to communicate using Bluetooth® with a mobile device such as a smartphone or tablet operating a software application corresponding to the vaporization device. The software application may enable a user to control various operations and settings of the vaporization device 1000 from a mobile device. In some cases, the vaporization device 1000 may also use Wi-Fi or other wireless communication protocols to communicate with a user's mobile device.

In some embodiments, the control panel 1200 may be movably coupled to support unit 1001. As shown in FIGS. 3D and 3E, the control panel 1200 can be rotationally coupled to the support unit 1001, e.g. by a hinge.

The control panel 1200 may be movable between a first position (shown in FIG. 3D) in which the surface 1200*a* of control panel 1200 is substantially perpendicular to the engagement surface of the support unit 10001 and a second position (shown in FIG. 3E) in which the surface 1200*a* of control panel 1200 is parallel to the engagement surface of the support unit 1001 and a second. The second position of the control panel 1200 may facilitate user interaction with the control panel 1200, as the user is likely to be positioned above the control panel 1200 (i.e. needing to move or face downward to see the control panel) when using the vaporization device 1000. Furthermore, retracting the control panel 1200 into the first position may provide a more compact support unit 1001 for storage.

Figure 6A:
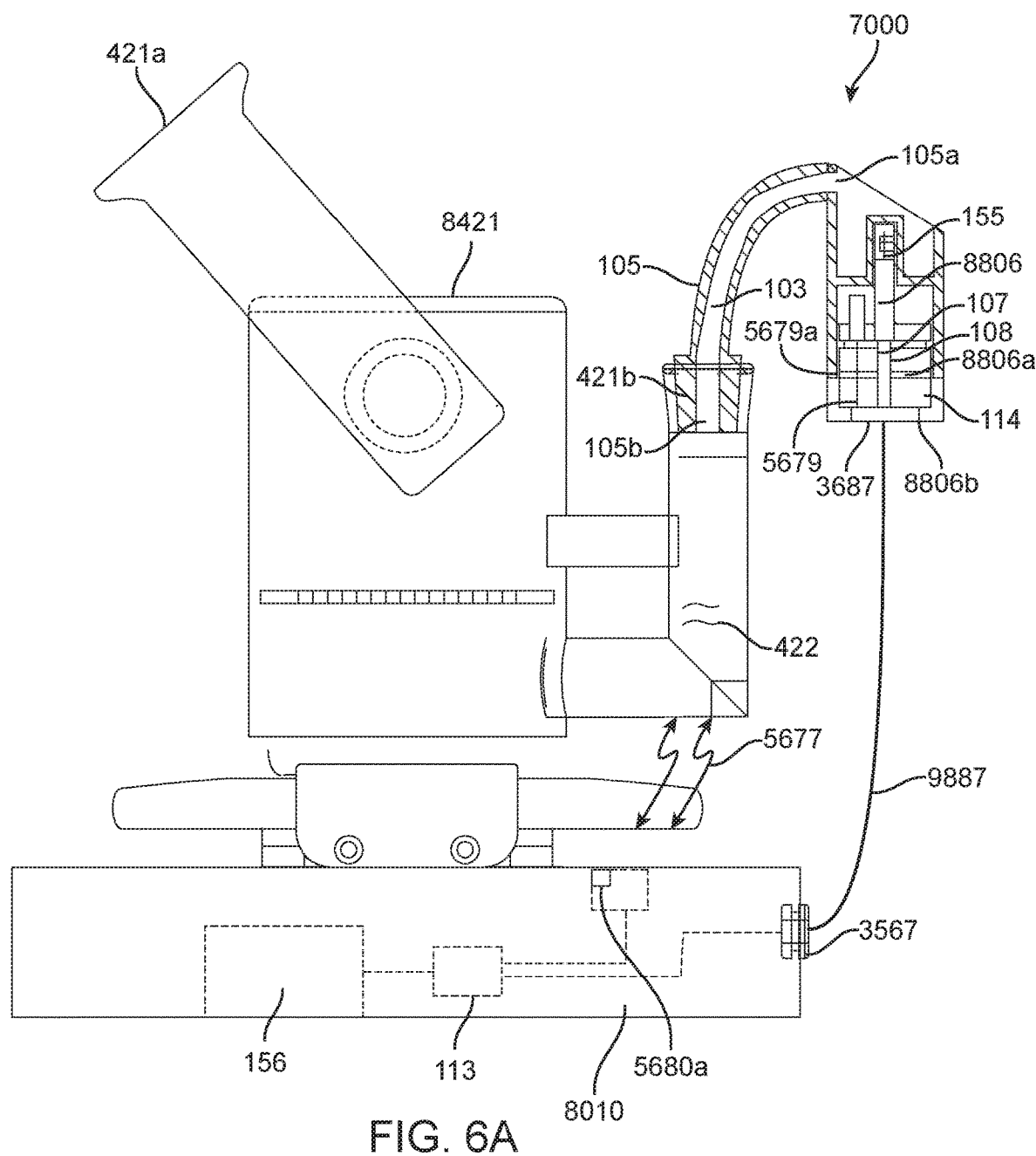
FIG. 6A shows a side view of another example of a vaporization device in accordance with an embodiment.
Figure 6B:
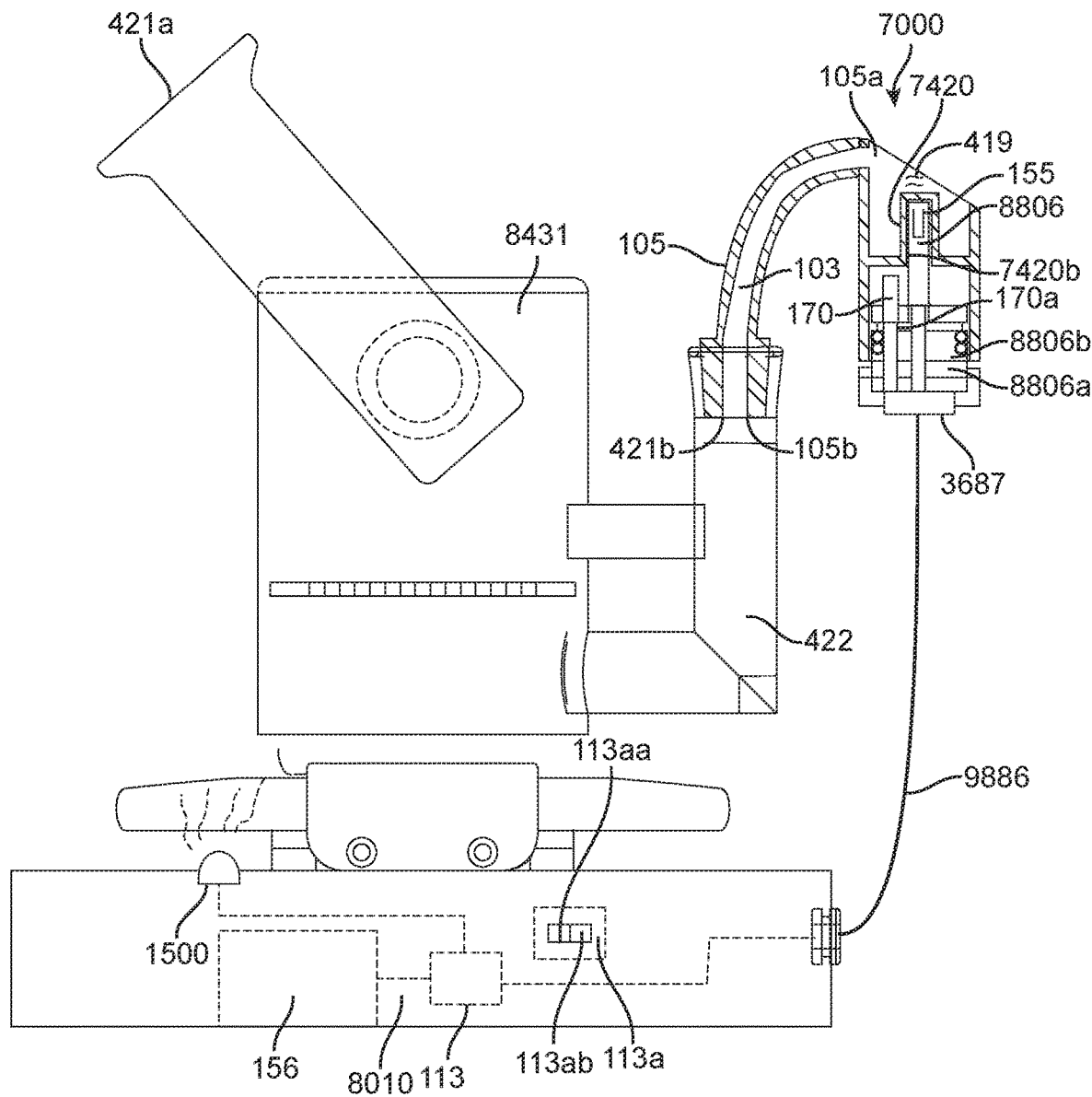
FIG. 6B shows a side view of the example of a vaporization device shown in FIG. 6A.

In some embodiments, the vaporization device 1000 may include voice activated user interfaces. FIG. 6E shows examples of a voice recognition processor 8080 that may be used with embodiments of the vaporization devices described herein. In some cases, the voice recognition processor 8080 can electrically powered by the electrical power source 156 through a power output port 1769, such as a USB port. The voice recognition processor may be implemented using various commercially available voice recognition components, such as an Alexa Voice Services (AVS) processor 8080*a* or a Google® Home Voice Services processor 8080*b*.

The voice recognition processor can be wirelessly coupled with the control circuit 113. A user may provide verbal commands to the voice recognition processor 8080. The voice recognition processor may then transmit these commands to the control circuit 113 to set or adjust various settings of the vaporization device 1000. Verbal commands may also be used to activate/deactivate heating of the heating element using the electrical power from power source 156. This may provide a user with increased control flexibility, which may enable users with limited mobility to use the vaporization device with minimal manual input.

For example, a user may verbally state "Alexa, ask Big E to set temperature to 650 degrees Fahrenheit". The Alexa voice recognition processor 8080α can process the command and transmit it to the first control circuit 113. The first control circuit 113 may then enable heating of the phyto material contact element 7419 to the predetermined vaporization temperature defined in the received verbal command.

Figures 6C, 6D:
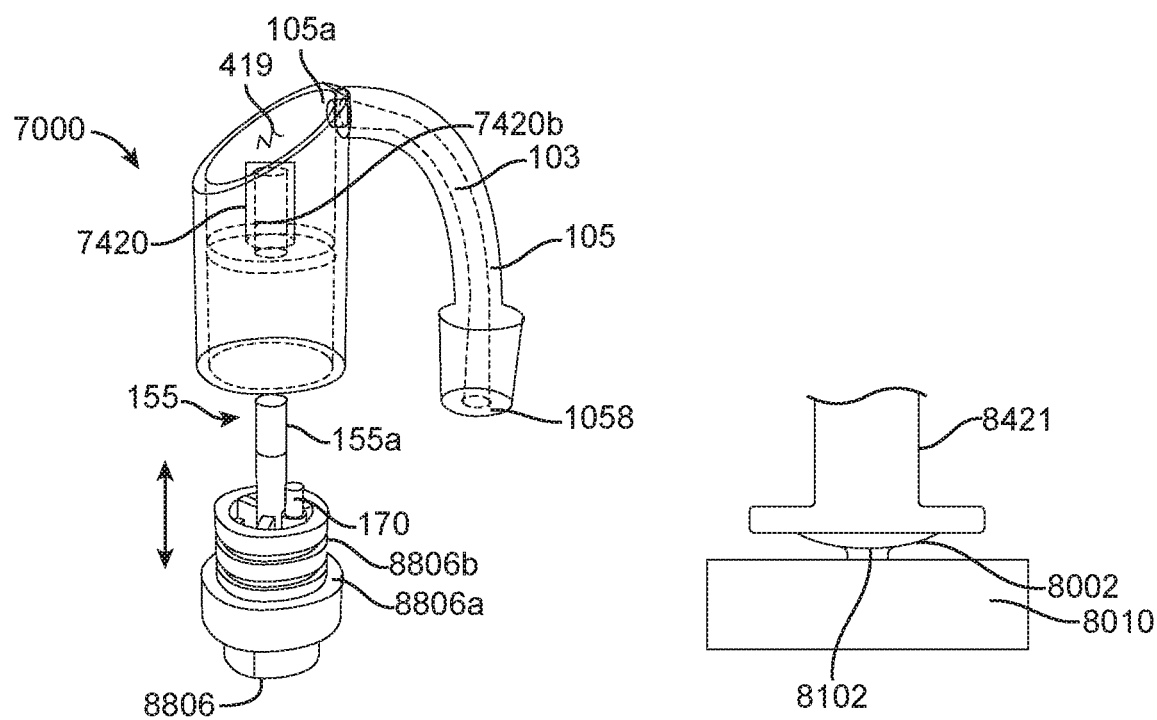
FIG. 6C shows an inside detail of an example vaporization element that may be used with the example vaporization device shown in FIG. 6A in accordance with an embodiment.
FIG. 6D shows a side view of another example support unit that may be used with the example vaporization device shown in FIG. 6A in accordance with an embodiment.
Figure 6E:
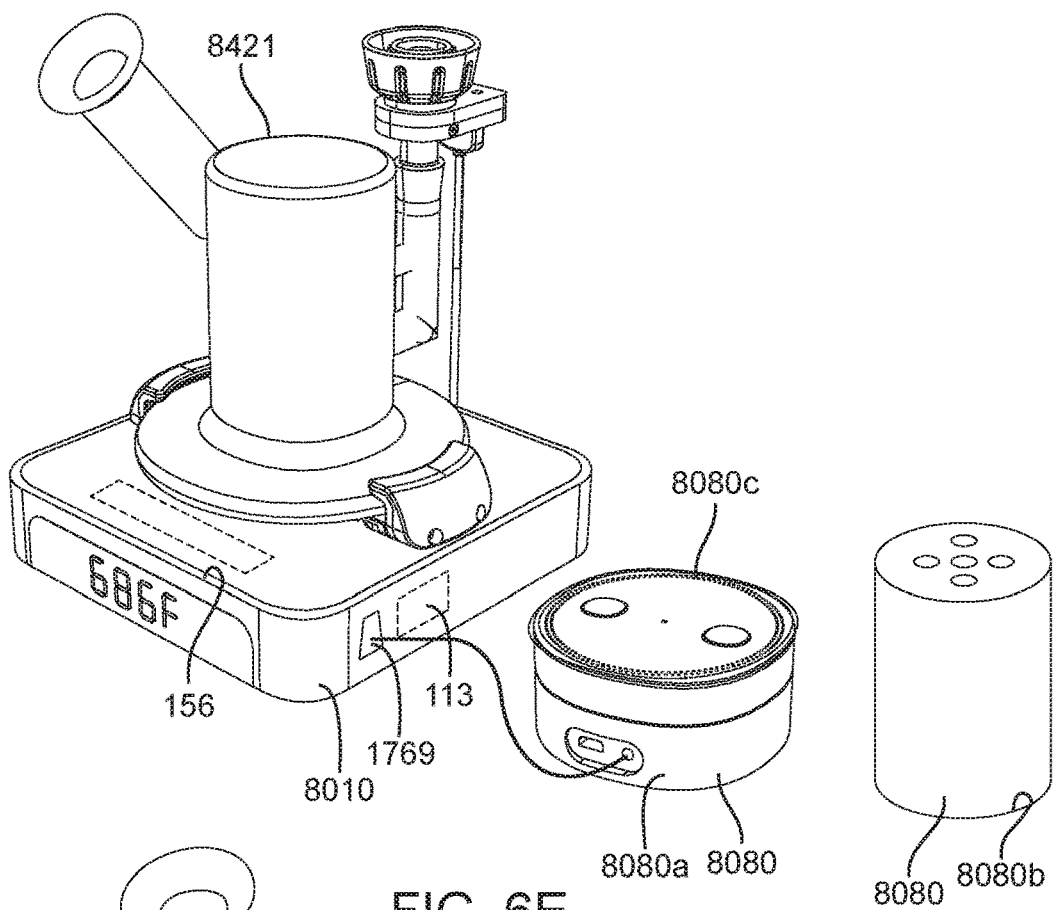
FIG. 6E shows a perspective side view of the example vaporization device shown in FIG. 6A and an example external control unit in accordance with an embodiment.
Figure 6F:
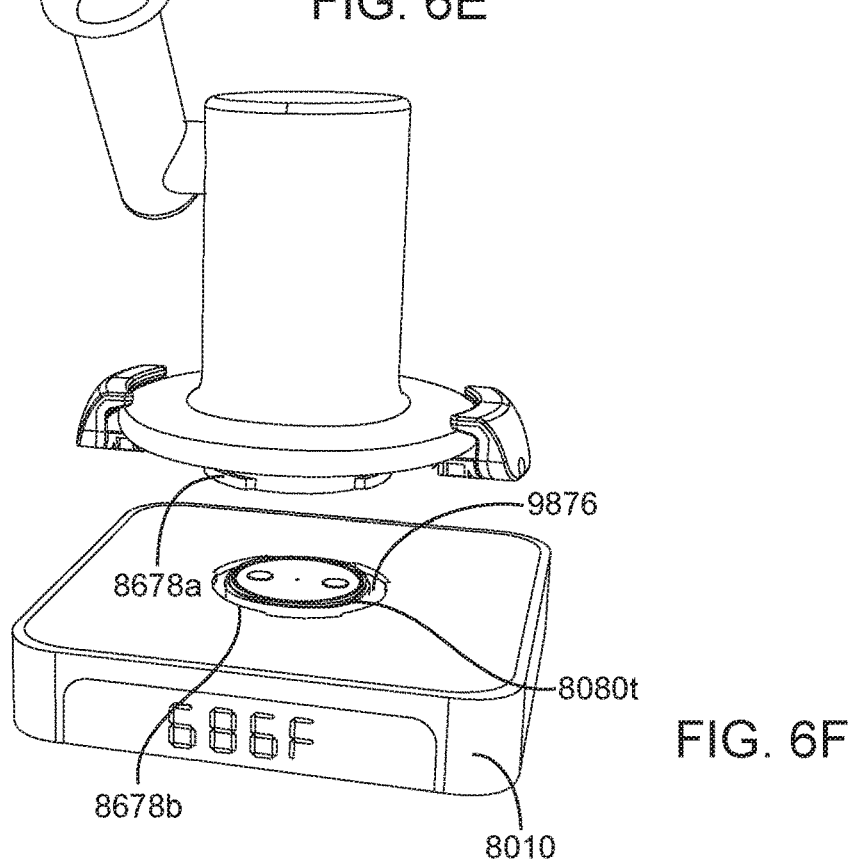
FIG. 6F shows a perspective view of an example support unit that may be used with the example vaporization device shown in FIG. 6A with an example vapor processing device removed in accordance with an embodiment.

In some examples, as shown in FIG. 6F, the support unit 8010 may include a cavity 9876. The cavity 9876 can be shaped to receive the voice recognition processor 8080 therein. The cavity 9876 can be arranged to expose, or at least partially expose, the microphone(s) of the voice recognition processor 8080 when the voice recognition processor is positioned in the cavity 9876. The cavity 9876 may also be arranged such that the microphone of the voice recognition processor 8080 remains accessible even when a water pipe 8421 is mounted to the support unit 8010.

Alternatively, as shown in FIG. 6E, the voice recognition processor 8080 may be separate from the support unit 8010. The voice recognition processor 8080 may not even be physically attached to the support unit 8010. For example, the voice recognition processor 8080 may be wirelessly coupled with the first control circuit 113.

In some cases, the vaporization device 1000 may also include additional output components. For example, the voice recognition processor 8080 may include at least one LED 8080z. The at least one LED 8080z may be used to illuminate at least a portion of a water pipe 8421 used with the vaporization device.

In some cases, the vaporization device 1000 may also include one or more audible output components. For instance a speaker 1867 may be disposed within the support unit 8001. The speaker 1867 may be electrically coupled with the first control circuit 113. The speaker 1867 may be used to provide audible outputs from the control circuit 113 indicating status information related to the vaporization device 1000.

In some cases, the speaker 1867 may also enable media playback. For instance, the speaker 1867 may be coupled to a wireless transceiver. The speaker 1867 may then be used to stream media, e.g. music, from a local wireless network or from a nearby device such as a smartphone 3333.

Figure 4A:
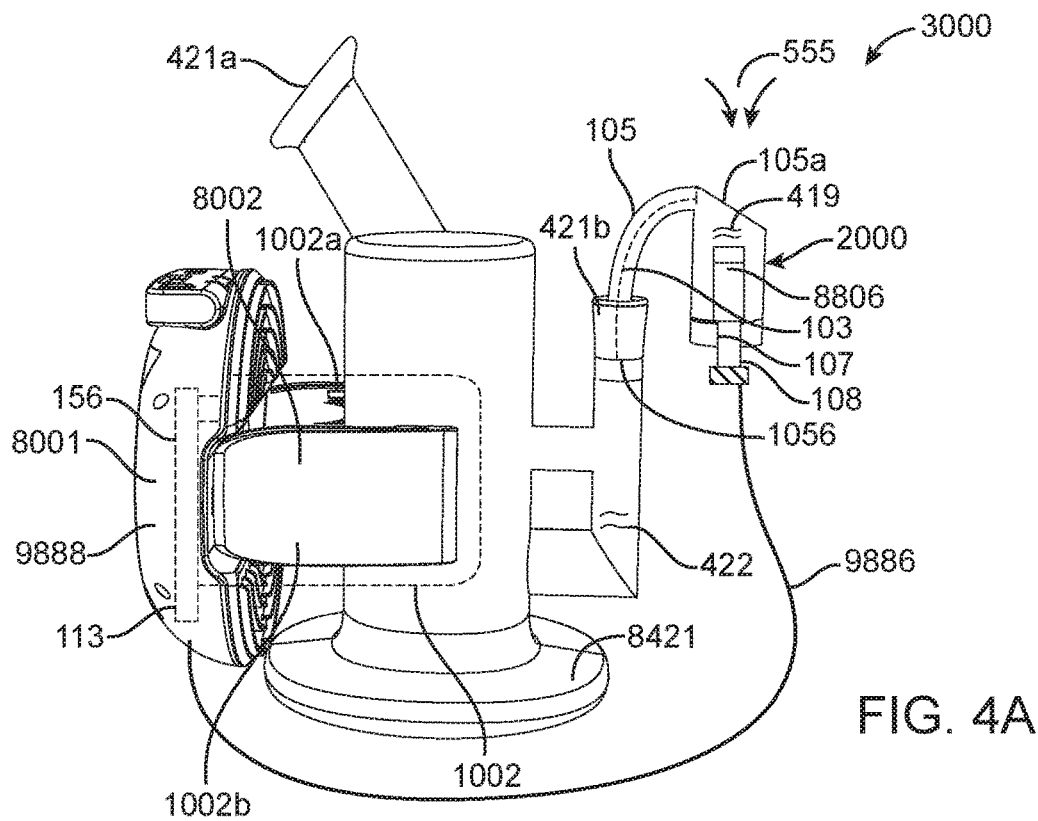
FIG. 4A shows a perspective side view of another example vaporization device in accordance with an embodiment.
Figure 4B:
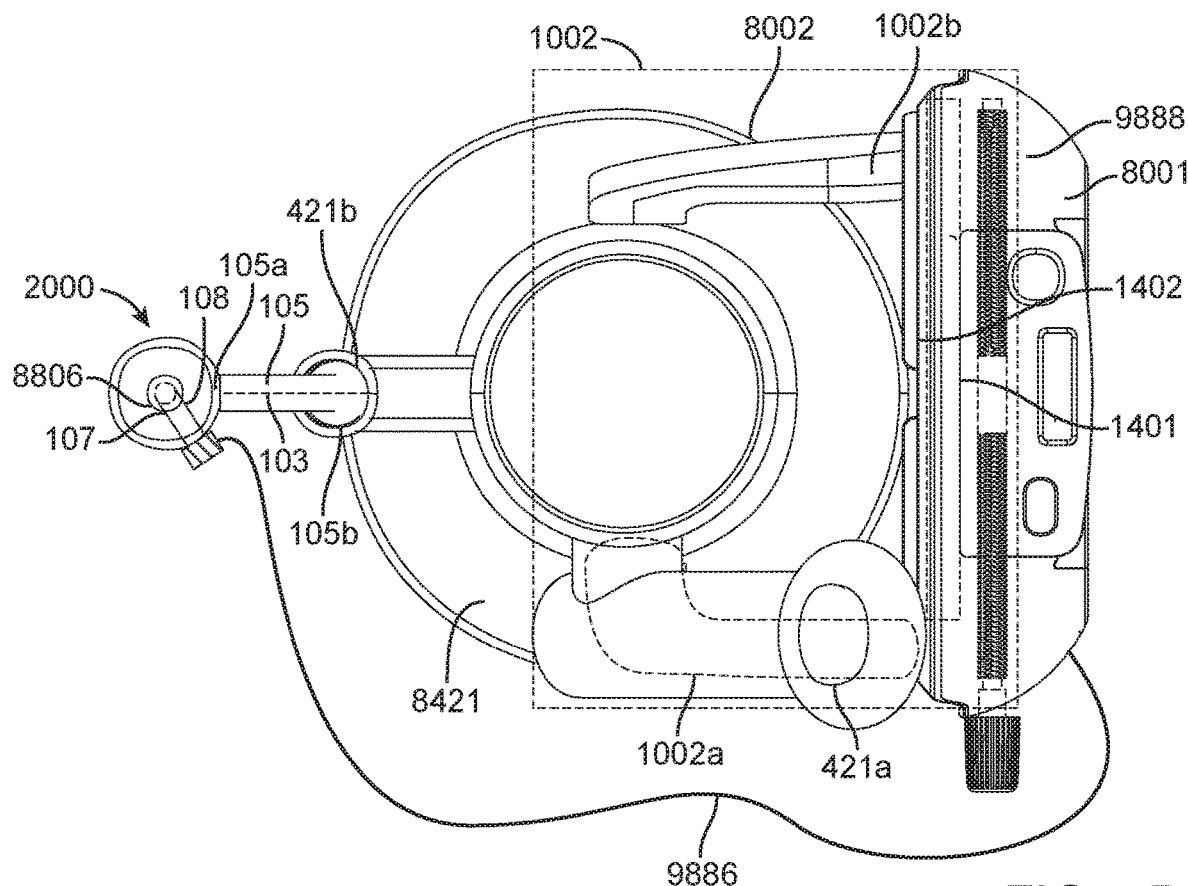
FIG. 4B shows a top view of the example vaporization device shown in FIG. 4A.

FIGS. 4A and 4B illustrate another example embodiment of a vaporization device 3000. Vaporization device 3000 includes a vaporization element 2000, a vapor processing device (water pipe 8421), and a support unit 8001.

The vaporization element 2000 can define a fluid pathway portion 103 that extends from a first end 105a to a vaporization element outlet 105b. The vaporization element outlet 105b can be fluidly coupled to the water pipe input port 421b. Accordingly, a continuous fluid pathway can be defined extending from the vapor inlet 105a through the vaporization element 2000 and water pipe 8421 to inhalation aperture 421a.

As with vaporization device 1000, the support unit 8001 can include an onboard electrical power source 156 and a control circuit 113. The vaporization element 2000 can be electrically coupled to control circuit 113 and power source 156 by connector cable 9886. The connector cable 9886 may be coupled to power electrical contacts 107/108 of the vaporization element 2000. The control circuit 113 may then control the power provided to the vaporization element 2000 from power source 156 to heat the phyto material contact element to the predefined vaporization temperature.

The support unit 8001 can also include a securement mechanism similar to that of support unit 1001. As shown in FIG. 4A, the securement mechanism can be in the form of a frictional engagement mechanism 8002.

In some embodiments of the vaporization devices described herein, a second control circuit 114 may be included in addition to the control circuit 113. The second control circuit 114 may be remote from the first control circuit. For instance, FIG. 6A illustrates a second control circuit 114 that is provided as part of the vaporization element 7000.

The second control circuit 114 can be electrically coupled to the resistive heater 155, e.g. via electrical contacts 107/108. The second control circuit 114 and control circuit 113 may cooperate to control and regulate the heating of vaporization element 7000. The second control circuit 114 can be electrically coupled to the electrical power source 156 using connector cable 9887.

The support unit 8010 may have a power coupling output port 3567. The connector cable 9887 may be detachably attachable to the support unit 8010 using power coupling output port 3567.

Alternatively, the connector cable 9887 may be integrated with the support unit 8010. In such cases, the power coupling output port 3567 may be omitted as the connector cable 9887 can provide that coupling.

The vaporization element 7000 can include a power coupling input port 3687. The connector cable 9887 may be detachably attachable to the vaporization element 7000 using the power coupling input port 3687.

Alternatively, the connector cable 9887 may be integrated with the vaporization element 7000. In some cases, the support unit, connector cable and vaporization element may be provided as a combined vaporization unit. This may facilitate assembly for use by a user, as there are fewer separate parts that need to be connected.

In other cases, providing the support unit, vaporization element and connector cable as separate components may be preferable. This may simplify replacing individual parts in case of failure. This may also allow various components to be substituted, such as using different vaporization elements with the same support unit. This may also allow different versions of the various components to be changed or substituted, such as replacing a support unit that does not support voice control with one that supports voice control for instance.

In some cases, the connector cable 9887 may be a simple two-conductor cable. In such cases, the connector cable 9887 may have a ground line and a positive voltage line to carry positive voltage from the electrical power source 156 to the vaporization element.

In some other cases, the connector cable 9886 may include at least three conductor lines. For instance, the connector cable 9886 may include a ground conductor line, a positive voltage conductor line, and a temperature signal line. The temperature signal line may communicate a temperature sensor signal from the vaporization element 2000 to the first control circuit 113. In some cases, the connector cable may include additional conductor lines, for instance to provide additional control or feedback signals between the first control circuit 113 and vaporization element.

In some cases, the second control circuit 114 may also be coupled to the first control circuit 113 by connector cable 9887. In some such cases, the connector cable may communicatively couple the second control circuit 114 to first control circuit 113. Accordingly, the power coupling output port 3567 and power coupling input port 3687 may then be modified to support additional signal transmission.

Alternatively, the second control circuit 114 and first control circuit 113 may communicate wirelessly. In such embodiments, the second control circuit 114 may still be electrically coupled to the power source 156 by connector cable 9887.

As shown in FIG. 6A, the support unit 8010 may include a wireless transceiver 5680. The first control circuit 113 can be communicatively coupled to the wireless transceiver 5680.

In some cases, the vaporization element 7000 can also include a second wireless transceiver 5679. The second wireless transceiver 5679 can be coupled to the second control circuit 114. The second control circuit 114 and first control circuit 113 may then communicate using a wireless link 5677 provided between the first wireless transceiver 5680 and the second wireless transceiver 5679.

In some cases, the first wireless transceiver 5680 may include a first optical transceiver 5680a. The second wireless transceiver 5679 may also include a second optical transceiver 5679a. The first wireless transceiver 5680 and second wireless transceiver 5679 may transmit optical signals therebetween. For instance, the first optical transceiver 5680a and the second optical transceiver 5679a may be implemented using infrared LED transmitters and infrared receivers.

In many cases, the processing devices 8421 used with the vaporization devices described herein may be transparent, or substantially transparent. Accordingly, optical signals may be transmitted through the processing devices. Optical communication (e.g. using infrared signals) may be preferred over other types of wireless communication, such as Bluetooth®. Optical communication may not require pairing between transceivers. Additionally, optical communication may require less power and optical communication component may be less expensive.

In other embodiments, various other wireless communication technologies may also be used to implement the wireless transceivers 5679/5680, such as radio frequency, Wi-Fi, and Bluetooth® for example. In some cases this may provide a more consistent wireless link 5677, for instance where the vapor processing device is not fully transparent and could interfere with optical signals.

The second control circuit 114 and first control circuit 113 may exchange control data and status data using the wireless communication link 5677 (or connector cable 9887 in wired communication embodiments). The first control circuit 113 may transmit heat control signals to the second control circuit 114 defining the current to be applied to the resistive heater 155. The control signals may be defined to adjust the temperature of the phyto material contact element 7419 in various ways, e.g. to heat the phyto material contact element 7419 to the predefined vaporization temperature, to maintain the phyto material contact element 7419 at the predefined vaporization temperature, to disable heating of the phyto material contact element 7419, to adjust the predefined vaporization temperature etc.

The second control 114 can transmit feedback signals to the first control circuit 113 to enable the first control circuit 113 to determine the temperature of the phyto material contact surface and/or whether adjustments are required to the current being provided to resistive heater 155. For instance, the second control circuit 114 may transmit temperature sensor signals to the first control circuit 114. The temperature sensor signals may include heating element temperature signals and/or ambient air temperature signals.

In some embodiments, the vaporization device may include one or more temperature sensors. For example, vaporization element 7000 shown in FIG. 6B includes a temperature sensor 170 in thermal communication with phyto material contact element 7419. The temperature sensor 170 can be positioned to sense the temperature of the phyto material contact element 7419. The temperature sensor 170 can generate a temperature signal indicative of the measured temperature.

The temperatures sensor 170 can be coupled to the first control circuit 113 (e.g. directly via connector cable 9886, or indirectly via second control circuit 114). The temperature sensor 170 can include a temperature signal output port 170*a* that can be communicatively coupled to the first control circuit 113. The temperature sensor 170 can transmit a temperature signal using temperature signal output port 170*a*.

The phyto material contact element 7419 can have a first side arranged to receive phyto material and/or phyto material extract. The first side of the phyto material contact element can define a phyto material contact surface 7420. The phyto material contact element 7419 can also include a second side 7420*b* opposite the first side. In some embodiments, the temperature sensor 170 can be positioned proximate (e.g. contacting) the second side 7420*b*.

The first control circuit 113 can receive the temperature signal from the temperature sensor 170. The first control circuit 113 may then determine the present temperature of the phyto material contact surface 7420 based on the received temperature signal. The first control circuit 113 may then define control signals for controlling the current provided to resistive heater 155 based on the received temperature signal. For instance, the control circuit 113 may pulse width modulate electrical power provided to the resistive heater 155 from the electrical power source 156 to attain the predefined vaporization temperature at the phyto material contact surface 7420.

The phyto material contact element can be positioned between the resistive heater 155 and phyto material extract 419 to be vaporized. Various configurations of the phyto material contact element 7419 are described in further detail herein below.

In general, the resistive heater 155 can be positioned proximate or adjacent to the second side 7420*b* of the phyto material contact element 7419. Heat from the resistive heater 155 can propagate through the phyto material contact element 7419 to the phyto material contact surface 7420. This heat can then be transferred to extract 419 positioned on the phyto material contact surface 7420 to vaporize the extract 419. The vapor 422 generated by vaporizing the extract 419 can then enter vapor inlet 105*a* and travel through the fluid pathway portions 103 and 8989 to the inhalation aperture 421*a* where it can be inhaled.

As mentioned, the temperature sensor 170 can be positioned proximate the second side 7420*b* of the phyto material contact element 7419. Accordingly, the temperature sensor 170 may sense the temperature of the second side 7420*b*. The control circuit 113 may determine the temperature of the phyto material contact surface 7420 using the temperature signal from the temperature sensor 170. The vaporization device may store calibration data, e.g. a lookup table 113*a*, that the control circuit 113 can access to determine the present temperature of the phyto material contact surface 7420 based on the temperature signal from the temperature sensor 170.

Calibration data, such as the lookup table 113*a*, may facilitate the calculation of the actual temperature of the heating element 7419 from the temperature signal from temperature sensor 170. The temperature sensor 170 can be positioned to measure a temperature proximate to the heating element 7419. However, it is the temperature of the phyto material contact surface 7420 that most closely corresponds to the temperature at which the phyto material extract is being heated.

In some cases, the temperature sensor 170 may sense a temperature that is slightly different from the actual temperature of the phyto material contact surface 7420*b*. The control circuit 113 may generate calibration data 113*aa* by measuring an actual temperature of the phyto material contact surface 7420*b* and the temperature signal data 113*ab* from the temperature sensor 170. The calibration data 113*aa* may be used by control circuit 113 to correlate the sensed temperature and the actual temperature of the phyto material contact surface 7420. In some cases, the calibration may be performed during manufacturing of the vaporization element and then stored in the vaporization device.

In some embodiments, the temperature sensor calibration may be performed by an end user. A thermometer probe may be provided with the vaporization device to measure the actual temperature of the phyto material contact surface 7420. This may be used to generate the calibration data for the lookup table 113*a*.

In some embodiments, the vaporization device may also include an orientation or tilt sensor 7423. For example, orientation sensor 7423 may be housed in the support unit 8010. The orientation sensor 7423 can be coupled to the control circuit 113.

The orientation sensor 7423 may sense the orientation of the support unit 8010. The orientation sensor 7423 can transmit an orientation signal to the control circuit 113 indicating the orientation and/or a change in orientation of the support unit 8010.

The control circuit 113 may determine whether the support unit 8010 has tipped over in response to the orientation signal. If the control circuit 113 determines that the support unit 8010 has tipped over, the control circuit 113 may disable the provision of power to the heater unit 8806. This may reduce the risk of a fire being started by the heater unit 8806 if the vaporization device tips over.

In some embodiments, the vaporization device may also include an extract insertion apparatus. The extract insertion apparatus may be used to insert or deposit a predefined volume of phyto material extract onto the phyto material contact surface. Depositing a predefined volume of phyto material extract onto the phyto material contact surface may provide increased control over the dose that is consumed by a user.

Figure 6J:
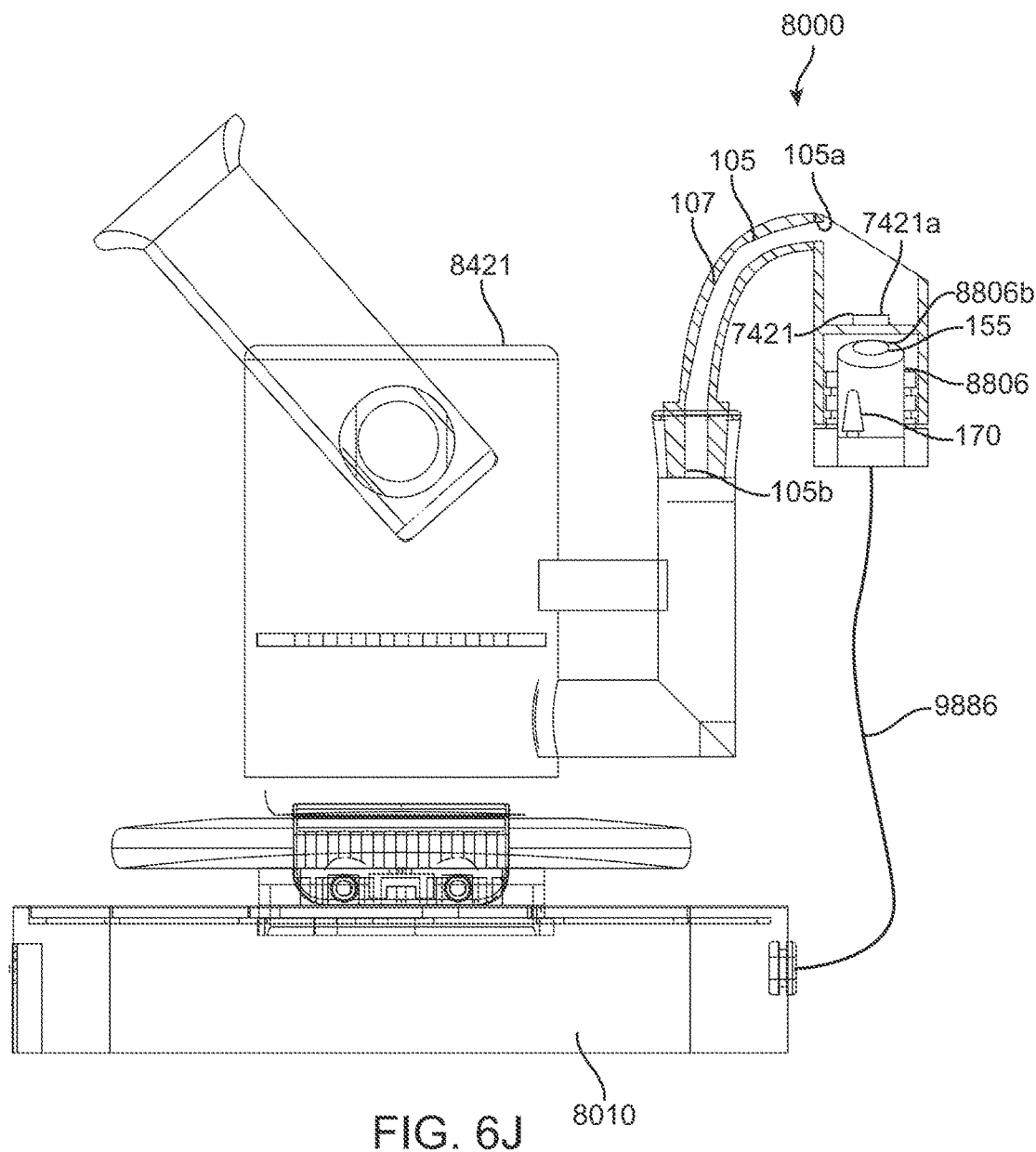
FIG. 6J shows a perspective side view of the example vaporization device shown in FIG. 6A with another example vaporization element in accordance with an embodiment.
Figure 6K:
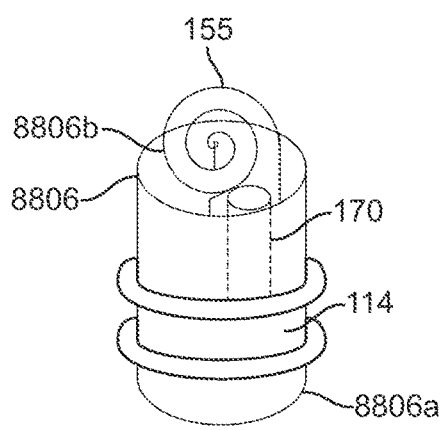
FIG. 6K shows an inside detail of the example vaporization element shown in FIG. 6J in accordance with an embodiment.
Figure 6L:
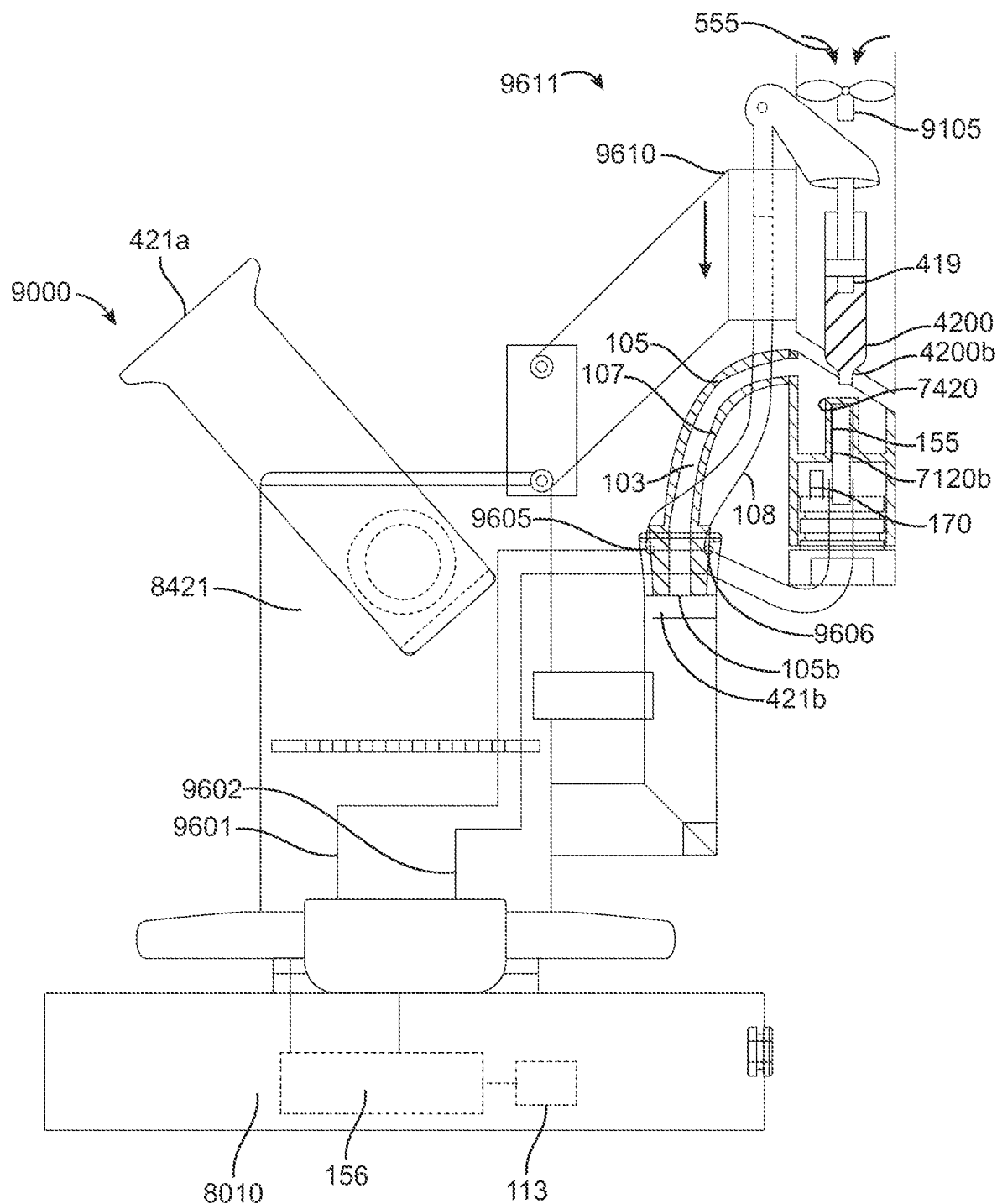
FIG. 6L shows a perspective side view of another example vaporization device in accordance with an embodiment.

FIG. 6L illustrates an example of a vaporization device 9000 that includes an extract insertion apparatus 9611 in accordance with an embodiment. In this embodiments, extract insertion apparatus 9611 can be mounted to water pipe 8421.

In the example shown in FIG. 6L, a pair of electrical power couplings or rails 9601/9602 may be used to couple the extract insertion apparatus 9611 to the control circuit 113, e.g. via power couplings 9603 and 9604. The extract insertion apparatus 9611 can also be coupled to the power source 156.

In some embodiments, the electrical power rails 9601 and 9602 can be disposed about the water pipe 8421. In other cases, the rails 9601/9602 may be embedded into the water pipe 8421. Embedding the electrical power rails 9601 and 9602 within the water pipe 8421 may provide a cleaner looking interface to the vaporization element as there may be fewer exposed wires (or a reduced extent of exposed wire). For instance in some cases portions of the water pipe 8421 can be manufactured of electrically conductive but thermally insulative materials such as vanadium oxide.

The first electrical power rail 9601 and second electrical power rail 9602 can be releasably electrically coupled along with the first power coupling 9603 and second power coupling 9604 to the first control circuit 113 and to the electrical power source 156. The first and second power couplings may allow for electrical power from the electrical power source 156 to be coupled to the water pipe 8421. The first and second electrical power rails 9601 and 9602 may terminate proximate the water pipe input port 421b at first rail power port 9605 and a second rail power port 9606. The ports 9605/9606 may be coupled to the first electrical contact 107 and the second electrical contact 108 respectively. The coupling between rails 9605/9606 and contacts 107/108 may be provided as a releasable magnetic coupling.

The extract insertion apparatus 9611 can include an extract ejector 4200 having a phyto material extract output port 4200a. The extract ejector may have an extract reservoir fillable with phyto material extract. An actuator 9610 may be electrically coupled to the first control circuit 113 and mechanically coupled to the extract ejector. The actuator may be operable to actuate the extract ejector to deposit a predefined volume of phyto material extract from the extract reservoir onto the phyto material contact surface via the phyto material extract output port.

In the example shown, a syringe actuator 9610 can be electrically coupled with the first rail power port 9605 and the second rail power port 9606. The syringe actuator 9610 can be operated to actuate a syringe 4200 having a reservoir filled with phyto material extract 419. The syringe 4200 can be actuated to deposit a predetermined volume of the phyto material extract 419 onto the phyto material contact surface 7420 via phyto material extract output port 4200a. For example, the control circuit 113 may actuate the syringe actuator 9610 by transmitting control signals to the syringe actuator either wirelessly (using a fourth wireless transceiver 5677) or through a wired connection.

In some cases, the vaporization device may also include an airflow meter 9105. The airflow meter 9105 may be operable to determine an air flow rate through the vaporization device fluid pathway.

Ambient air 555 may enter the first end 105a of the elongated member 105 through an ambient air input aperture 555a. The ambient air input aperture 555a can be disposed upstream and in fluid communication with an airflow meter 9105. The airflow meter 9105 can measure the flow of ambient air therethrough. For instance, the airflow meter 9105 may be a mass airflow meter. The mass airflow meter may measure the mass of air substance which passes therethrough per unit of time.

The airflow meter 9105 can be electrically coupled with the first control circuit 113, e.g. through the first rail power port 9605 and the second rail power port 9606. The mass airflow meter 9105 may be operable to generate initial air flow data based on an initial flow of ambient air passing therethrough. The airflow meter 9105 can transmit the initial air flow data to the control circuit 113 either wirelessly (using a third wireless transceiver 5678) or through a wired connection.

In some cases, the control circuit 113 may adjust the volume of extract 419 deposited on the phyto material contact surface based on the air flow data. For instance, a change in airflow may be used to activate or deactivate the deposit of extract (e.g. to initiate extract being vaporized when air is being inhaled).

By controlling the volume of phyto material extract deposited to the phyto material contact surface 7420 and vaporized, the control circuit 113 may control and/or monitor the quantity of extract being vaporized. The control circuit 113 may further determine based on the air flow measurements an estimate of the vaporized extract that was consumed by a user. The control circuit 113 may then store the consumption data and/or transmit the consumption data to a remote device. This may be used to configure the vaporization device as a measured dose system. In some cases, calibration of the vaporization device may be required to determine a percentage of phyto material vapor present in the mass of air flowing through the mass airflow meter 9105 when inhaled from the inhalation aperture 421a.

Another example embodiment of an extract insertion apparatus is shown in FIG. 8A. As shown in the example of FIG. 8A, the extract insertion apparatus can provided as a robotic measured dose apparatus 1300. The extract insertion apparatus 1300 can include a robotic arm 8568. The arm 8568 may have a plurality of controllable axes, such as at least two axes. For example, the arm 8568 may be implemented using a SCARA robotic arm.

The arm 8568 can include an end effector 8568a. A syringe 4200 may have a reservoir filled with the phyto material extract 419. The syringe 4200 can also include a phyto material extract output port 4200a.

An ejection actuator 9610 can be electrically coupled with the first control circuit 113 and mechanically coupled with the syringe 4200. The actuate 9610 may be operable to actuate the syringe 4200 to deposit a predetermined volume of the phyto material extract 419 onto the phyto material contact surface 7420 from the phyto material extract output port 4200a.

The arm 8568 and end effector 8568a can be coupled with the syringe actuator 9610. The robotic arm 8568 may be movable to controllably positioning the phyto material extract output port 4200a proximate the phyto material contact surface 7420. This may facilitate depositing a predetermined volume of the phyto material extract 419 onto the phyto material contact surface 7420 for vaporization.

In some embodiments, the robotic measured dose apparatus 1300 may be provided in combination with a vaporization device including a voice recognition processor 8080 (see e.g. FIG. 6E). In such embodiments, the vaporization device may enable completely hands free operation by the end user. The robotic measured dose apparatus 8568 may enable the vaporization device to be used by individuals who may be physically or mentally injured or disabled and thus do not have sufficient control or movement of their limbs to be able to consume phyto material extracts 419, for instance if prescribed as medication.

The syringe 4200 may be pre-loaded with phyto material extracts 419. The end effector 8568a can position the phyto material extract output port 4200a to momentarily dispense the phyto material extract 419 onto the phyto material contact surface the vaporization. The end effector 8568a may subsequently withdraw and move away to enable a potential carb cap operation (not shown). Such carb cap operations may also be performed automatically, e.g. using the robotic arm 8568.

In some embodiments, a plurality of extract ejectors 4200 may be coupled to the end effector. The plurality of extract ejectors may be filled with one or more types of phyto material extract. For example, each extract ejector may be filled with a different type of phyto material extract. This may allow a user to easily select the type of extract to be vaporized.

In some examples, a user may specify which of the plurality of phyto material extracts 419 they wish to utilize. For example, the user may verbally select the type of phyto material extract by issuing verbal commands to a voice recognition processor. Additionally or alternatively, the end user may use a mobile device such as a tablet or smartphone in order to select at least one of the phyto material extracts 419 to be dispensed. In some cases, a user may provide identifying user data, such as an email address or cell phone number, to enable the phyto material extract 419 (or the selected type) to be deposited.

Vaporization Element

The following is a general description of a vaporization element that may be used by itself or in combination with one or more aspects of the disclosure herein, including a vaporization device, a support unit for a vaporization device, and/or a method for vaporizing phyto material and/or phyto material extract. The following description contains various features of a vaporization element that may be used individually or in any combination or sub-combination.

In general, vaporization elements in accordance with embodiments described herein can include a heating element defining a phyto material contact surface, an electrical heater, and a vaporization element fluid pathway. The vaporization element fluid pathway generally extends from a vapor inlet proximate to the phyto material contact surface to a vapor outlet. In some cases, the vapor outlet can be fluidly coupled to other components of a vaporization device, such as a processing device for example. In some cases, the vapor outlet may correspond to an inhalation aperture.

In embodiments of the vaporization elements described herein, the vaporization element may be configured with two adjacent, but separate, sections. The vaporization element may include a vaporization section in which extract can be received and vaporization. The vaporization element may also include a heater section in which an electrical heater can be positioned. The heater section and vaporization section can be thermally coupled so that heat from the electrical heater is transferred from the heater section to the vaporization section.

In some embodiments, the heater section and vaporization section can be separated from one another by an intervening surface that may prevent fluids from travelling directly between the heater section and vaporization section. This may prevent extract and extract residue from contacting components in the heater section which could clog or damage the heater components.

The heater section and vaporization section may be separated by a heating element. A first side of the heating element may define a phyto material contact surface on which extract can be received. A second, opposite, side of the heating element can be positioned at an end of the heater section and facing towards the heater section.

In some cases, the heating element may be formed integrally as part of the vaporization section. In other cases, the heating element may be a separate component from the vaporization section and the heater section, e.g. a heating element insert.

The heater section can be arranged to receive the electrical heater at a position adjacent to the second side of the heater element. When the electrical heater is active, heat can be transferred from the electrical heater to the second side of the heating element, through the heating element to the phyto material contact surface where it can vaporize phyto material extract.

Referring to FIGS. 1A-1D, shown therein is an example vaporization element 2001. Vaporization element 2001 is an example of a vaporization element 2000 that may be used with various embodiments of the vaporization devices described herein above.

In vaporization element 2001, the vaporization element fluid pathway 103 is defined by an elongated hollow member 105. The hollow member 105 has a hollow central portion that defines the fluid pathway 103. The fluid pathway 103 extends from a first end 105a of the elongated member 105 to the second end 105b of the elongated member 105. In vaporization element 2001, the hollow member 105 can define a substantially straight fluid pathway 103 extending from the first end 105a to the second end 105b.

The second end 105b of the elongated member 105 can be shaped to fluidly couple the vaporization element 2001 with processing device such as a water pipe 421/8421. The second end 105b of the elongated member 105 may be fluidly coupled with an input port 421b of a water pipe, as shown for example in FIGS. 2A and 3A.

The vaporization element 2001 can also include a heating element 106. As shown, vaporization element 2001 has an annular heating element 106. The heating element 106 may be used to receive phyto material and/or phyto material extract and to vaporize the received phyto material and/extract.

The heating element 106 can define a phyto material contact surface 106a. The phyto material contact surface 106a refers to the surface of the heating element 106 on which phyto material extract can be positioned for vaporization. The phyto material contact surface 106a can be heated to a predefined vaporization temperature in order to vaporize extract 419 positioned on the surface 106a.

The first end 105a of the hollow member 105 may be referred to as a vapor inlet 105a. The vapor inlet 105a can be positioned proximate to the phyto material contact surface 106a so that vapor emitted from extract being vaporized can enter the fluid pathway 103. In the example shown, the vapor inlet 105a is positioned above the phyto material contact surface 106a. This may facilitate capturing the rising vapor that is emitted from extract 419 being vaporized.

As in the example shown, the heating element 106 can surround hollow member 105. That is, the heating element 106 can have an annular shape about a central axis. The hollow member 105 can be cylindrically shaped and may be substantially coaxial about the same central axis as the heating element 106. Vapor emitted from extract 419 positioned throughout the heating element 106 may thus pass close by the vapor inlet 105a. The vapor can then be easily pulled into the vapor inlet 105a when a user inhales from the far end of the fluid pathway.

The phyto material contract surface 106a can be defined by a first side of the heating element 106. On the second side 106b of the heating element 106, opposite the first side, an electrical heater 155 can be disposed proximate to the second side 106b of the heating element 106 (e.g. adjacent to, contacting, or even formed in the second side 106b). In the example shown in FIG. 1D, the electrical heater 155 can be provided as a resistive heater formed by metallic planar heater 168.

The metallic planar heater 168 can be positioned on the second side 106b of the heating element 106 proximate to (and in some cases in direct contact with) the second side 106b. The resistive heater 168 can generate heat when current flows therethrough from a power source such as electrical power source 156.

In some embodiments, the electrical heater 155 may be a laser diode heater. The laser diode heater may be positioned to emit light that is focused proximate the phyto material contact surface 106a. The laser light may transfer to impart energy to the phyto material contact surface 106a to heat the phyto material contact surface 106a in order to enable vaporization of the phyto material or phyto material extract.

The electrical heater 155 can extend between a first electrical lead or contact 107 and a second electrical lead or contact 108. The electrical contacts 107 and 108 can be used to electrically connect the electrical heater 155 to an electrical power source such as power source 156. As explained herein above, the power source 156 can provide power to resistive heater 168 to generate thermal energy which can be transferred to heating element 106.

Figure 1D:
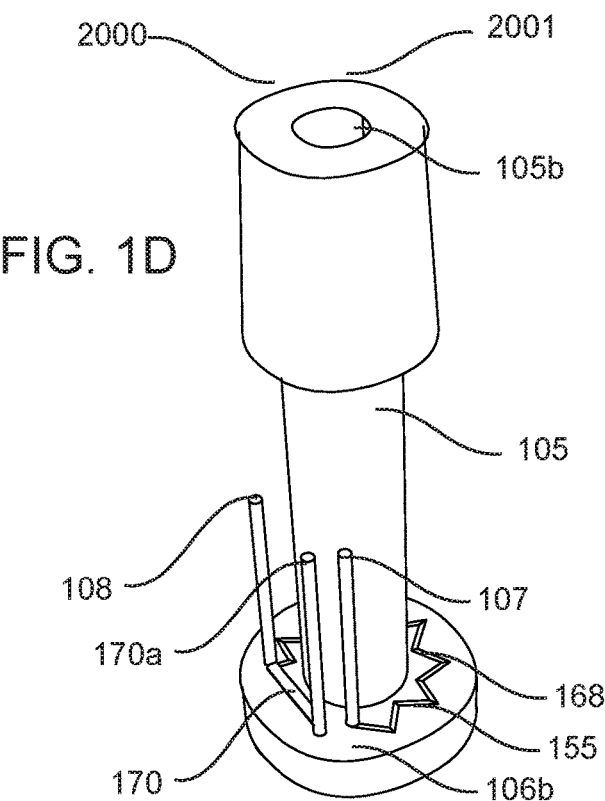
FIG. 1D is a perspective bottom view of the example vaporization element shown in FIG. 1A.

In the example shown in FIG. 1D, the vaporization element 2000 can also include a temperature sensor 170. The temperature sensor 170 can be thermally coupled with at least one of the elongated hollow member 105 and the annular heating element 106. The temperature sensor 170 can be positioned proximate the second side 106b of the heating element 106.

In some cases, as shown in FIG. 1D, the temperature sensor 170 may be positioned proximate a portion of the second side 106b of heating element 106 in which the resistive heater 168 is not present. This may enable the temperature sensor 170 to provide a temperature signal that is more representative of the temperature of the heating element 106 (i.e. it may reduce error that may be introduced by the sensor 170's proximity to the heater 168.

The temperature sensor 170 can generate a temperature signal representative of the temperature of the heating element 106. As shown, the temperature sensor 170 can include a temperature signal output port 170a that can be coupled to a control circuit, such as control circuits 113 or 114 described herein above.

In some cases, the resistance of temperature sensor 170 may vary with respect to the temperature sensed by the temperature sensor 170. The sensor 170 may then generate a temperature signal based on the resistance of the temperature sensor 170. As a skilled reader will appreciate, various types of temperature sensors may be used, such as thermocouples for example.

In operation, when the electrical heater 155 is heated, thermal energy can be transferred through the heating element 106 to the phyto material contact surface 106a. A portion of the thermal energy may also be transferred to portions of the hollow member 105 proximate the resistive heater 155. For example, thermal energy can be transferred to the hollow member 106 proximate the first end 105a of the fluid pathway 103.

As a result of the thermal energy from the resistive heater 155, the phyto material contact surface 106a can be heated to a predetermined vaporization temperature. Phyto material extract 419 deposited onto the phyto material contact surface 106a can then be vaporized. This vapor may then enter the vapor inlet 105a of the fluid pathway 103 and travel through the fluid pathway 103 to the vapor outlet 105b where it can be fluidly coupled to an inhalation aperture, e.g. via a processing device such as a water pipe.

In general, the vaporization element 2000 may preferably be manufactured from materials that are chemically inert and medically safe for vaporization. Non-porous materials may also be preferred to avoid extract being absorbed when deposited for vaporization.

The materials used to manufacture the vaporization element 2000 may also have a high temperature stability to allow the vaporization element 2000 to be heated to temperatures up to 700 degrees Fahrenheit, and preferably upwards of 1000 degrees Fahrenheit or greater.

In some cases, materials having a smooth finish or surface may be preferred for the vaporization element 2000 (and in particular the vaporization section). This may facilitate cleaning thereof.

In some embodiments, vaporization element 2000 may be manufactured of various materials having low thermal conductivity, such as glass, quartz or ceramic materials for instance. In some cases, glass or ceramic materials used may minimally impact the flavor of extract being vaporized.

As a skilled reader will appreciate, some ceramic materials may have fine particles that not safe for inhalation. Accordingly, such materials may be avoided when manufacturing the vaporization element 2000. In some cases, porous (or more porous) ceramic materials may also be avoided to reduce or prevent extract absorption.

In some embodiments, manufacturing of the vaporization element 2000 may also include silicon carbide. For example, silicon carbide may be used to manufacture the phyto material contact element. Silicon carbide may provide greater heat faster than quartz while being inert and safe for use with vaporization.

In some cases, the vaporization element 2000 may include a thermal interface between the heating element 106 and the hollow member 105. For instance, a ceramic glaze may be used to couple the heating element 106 and the hollow member 105. In various embodiments, the thermal interface may be manufactured of materials including silica or aluminum oxide.

The thermal interface between the heating element 106 and the hollow member 105 may allow the hollow member 105 to expand radially (i.e. in a direction perpendicular to the axis of the fluid pathway 103) as it is heated. Without such a thermal interface, the hollow member 105 and heating element 106 may expand at different rates which could result in cracking of the annular heating element 106 due to expansion forces of the hollow member 105.

In some embodiments, the heating element 106 and hollow member 105 may be manufactured as a unit. This may ensure that a proper thermal interface is provided between the heating element 106 and hollow member.

In some embodiments, where hollow member 105 and heating element 106 are formed separately, the hollow member 105 may be manufactured using metals such as aluminum. The metal materials may be coated using ceramics such as Titanium Nitride. In some cases, only those portions of the hollow member 105 defining the fluid pathway 103 may need to be coated.

Manufacturing the hollow member 105 using a non-brittle material (i.e. not ceramic or glass) may provide greater mechanical strength and reduce breakage. In such embodiments, the hollow member 105 may be engaged, e.g. frictionally coupled or hinged, with the heating element 106 (see e.g. FIGS. 12A-12C).

Figure 1F:
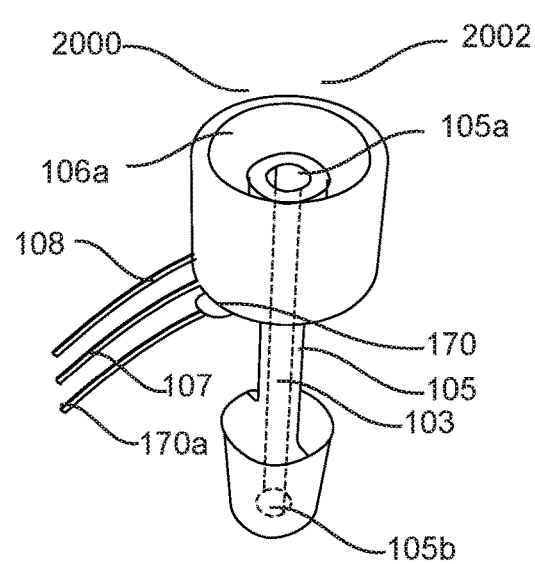
FIG. 1F is a top perspective view of the example vaporization element shown in FIG. 1E.
Figure 1E:
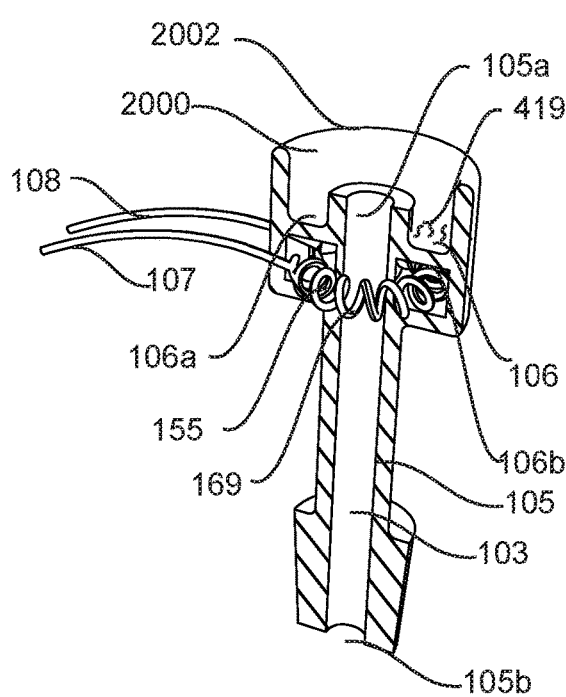
FIG. 1E is a cut-away view of another example vaporization element in accordance with an embodiment.

FIGS. 1E and 1F illustrate another example vaporization element 2002 in accordance with an embodiment. Vaporization element 2002 is an example of a vaporization element 2000 that may be used with various embodiments of the vaporization devices described herein above.

As with vaporization element 2001, the vaporization element 2002 can include an annular heating element 106 and an elongated hollow member 105. The heating element 106 and hollow member 105 can be secured to one another (or manufactured as a unit) to allow the hollow member 105 to expand as it is heated.

In vaporization element 2002, the electrical heater 155 can be housed within an enclosed heater section. In this example, the electrical heater 155 is in the form of a coiled resistance wire 169 disposed proximate the section side 106b of the heating element 106.

The resistance wire 169 is electrically connected to the first and second electrical contacts, 107 and 108, extending out from the enclosed heater section. The electrical contacts 107/108 can be used to connect the resistance wire 169 to an electrical power source.

The vaporization element 2002 can also include a temperature sensor 170. The temperature sensor 170 can be thermally coupled with at least one of the elongated hollow member 105 and the annular heating element 106.

As with vaporization element 2001, in vaporization element 2002 the temperature sensor 170 can be positioned proximate the second side 106b of the annular heating element 106. The temperature sensor 170 can output a temperature signal based on the measured temperature of the second side 106b of the annular heating element 106.

Components of the vaporization element 2002 such as the elongated hollow member 105 and heating element 106 may be manufactured of a low thermal conductivity material, such as glass or quartz. Similarly, the thermal interface between the annular heating element 106 and the elongated hollow member 105 may be manufactured of glass or quartz. A glass or quartz vaporization element 2000 may enable a user to see the resistance wire 169 as it heats up. In some embodiments, the resistance wire may glow as the predetermined vaporization temperature is reached. This may provide a simple indicator that extract 419 can be positioned on the phyto material contact surface 106a.

Figure 1G:
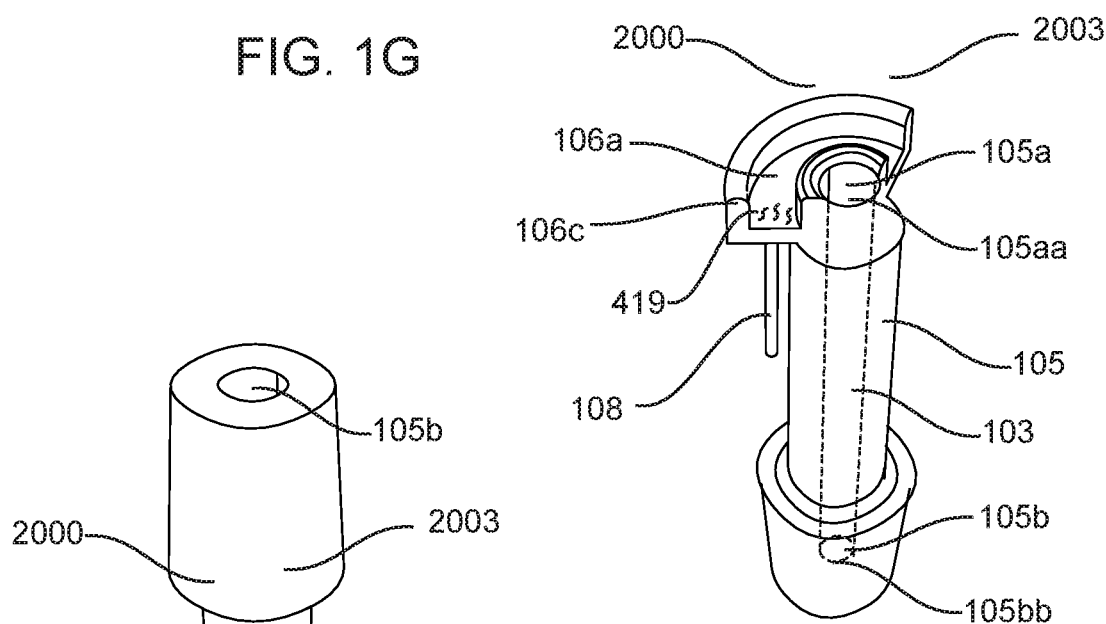
FIG. 1G is a top perspective view of another example vaporization element in accordance with an embodiment.
Figure 1H:
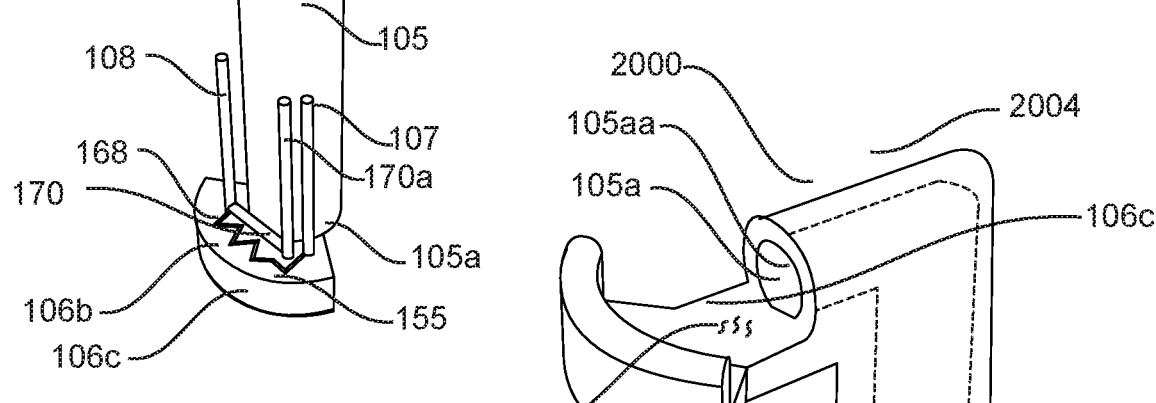
FIG. 1H is a bottom perspective view of the example vaporization element shown in FIG. 1G.

FIGS. 1G and 1H illustrate another example vaporization element 2003 in accordance with an embodiment. Vaporization element 2003 is an example of a vaporization element 2000 that may be used with various embodiments of the vaporization devices described herein above.

The vaporization element 2003 can include a hollow member 105 and a heating element 106c similar to vaporization elements 2001 and 2002. In vaporization element 2003, however, the heating element 106c is a partially annular heating element. That is, heating element 106c may only partially surround the fluid pathway 103.

The heating element 106c extends along an arc of less than 360 degrees. For example, the heating element 106c may surround the fluid pathway along an arc of about 90 degrees.

Similar to vaporization elements 2001 and 2002, the first side of the heating element 106c defines a phyto material contact surface 106a. A resistive heater 168 can be positioned proximate to the second side 106b of heating element 106c. Similarly, a temperature sensor 170 can be positioned proximate to the second side 106b of the heating element 106c. The temperature sensor 170 and resistive heater 168 may operate as described herein above. In the example shown in FIG. 1H, the temperature sensor 170 can be positioned to contact the second side 106b of the heating element 106c between the heater 168 and hollow member 105.

Figure 1I:
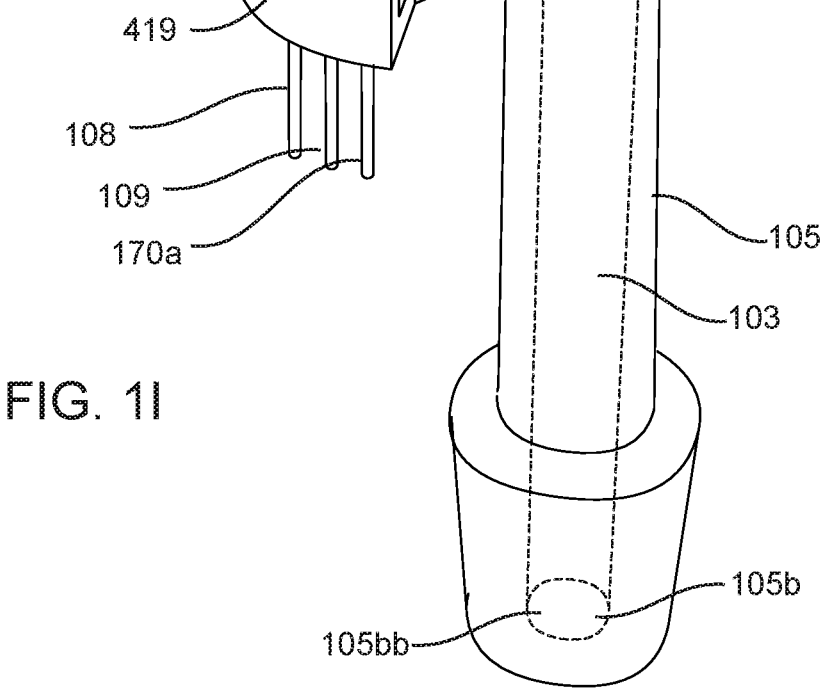
FIG. 1I is a side perspective view of another example vaporization element in accordance with an embodiment.

FIG. 1I illustrate another example vaporization element 2004 in accordance with an embodiment. Vaporization element 2004 is an example of a vaporization element 2000 that may be used with various embodiments of the vaporization devices described herein above. FIG. 1I illustrates a modified version of electronic vaporization element 2003 in which the hollow member 105 is not completely straight.

In vaporization element 2004, the hollow member 105 includes a curved or angled section. A first portion of the fluid pathway 103 extending inward from the vapor inlet 105a extends along a vapor inlet axis. A second first portion of the fluid pathway 103 extending inward from the vapor outlet 105b extends along a vapor outlet axis. The vapor inlet axis and the vapor outlet axis are not coaxial in vaporization element 2004. In some cases, the vapor inlet axis and the vapor outlet axis may be substantially perpendicular as shown in FIG. 1I.

As shown in FIG. 1I, the vapor inlet 105a of hollow member 105 can be positioned facing the heating element 106c. Accordingly, when air is drawn in through the vapor inlet 105a a negative pressure may be applied directly to the vapor emitted from extract 419 positioned on the phyto material contact surface 106a.

In vaporization element 2004, the resistive heater 155 can be radially disposed away from the hollow member 105. For instance, resistive heater 155 may be positioned at a distance of about 20 mm from the second end 105a of the hollow member 105. In contrast, in vaporization element 2003 the resistive heater 155 may be positioned at a distance of about 6 mm from the second end 105a of the hollow member 105. Accordingly, the vaporization element 2004 may reduce the transfer of thermal energy to the hollow member 105. This may provide a lower thermal inertia for heating element 106*c*. This may reduce the time required to heat the phyto material contact surface 106*a* to the predefined vaporization temperature. This may also reduce the power required to heat the phyto material contact surface 106*a* to the predefined vaporization temperature.

In some embodiments where the vaporization element 2004 is manufactured using quartz materials, a pancake ceramic heater or a resistance wire 169 may be preferred for the resistive heater 155. In some embodiments where the vaporization element 2004 is manufactured using a ceramic material, a planar metallic heater 168 can be sintered onto the ceramic to provide the resistive heater 155.

In some embodiments, the vaporization element 200 may include one or more input/output ports. The ports may be used to couple the vaporization element 200 to a power source and/or control circuit as described herein above.

As shown in FIG. 3J, the vaporization element 2000 can include a coupling port 2000*c* that provides electrical coupling to power the resistive heater 155. The coupling port 2000*c* can include couplings to electrical contacts 107/108 that provide power to the resistive heater 155.

The coupling port 2000*c* can also provide additional coupling to allow sensors signals, such as temperature sensor signals, to be transmitted to the control circuit 113 via a connector cable 2000*b*. For instance, the coupling port 2000*c* can include a temperature signal output port 170*a*.

The vaporization element 2000 can also include connector cable engagement members. These connector cable engagement members may be used to attach the connector cable to the coupling port 2000*c*. For example, FIG. 3J illustrates a pair of magnets 1974*a* positioned on a vaporization element end of the connector cable 2000*b*. The vaporization element 2000 can include a correspond pair of magnets 1974*b*. The magnets 1974*a* and 1974*b* can be used to secure the connector cable 2000*b* to the vaporization element 2000. Alternatively, various mechanical coupling may be used, such as pin connectors for example.

Figure 4C:
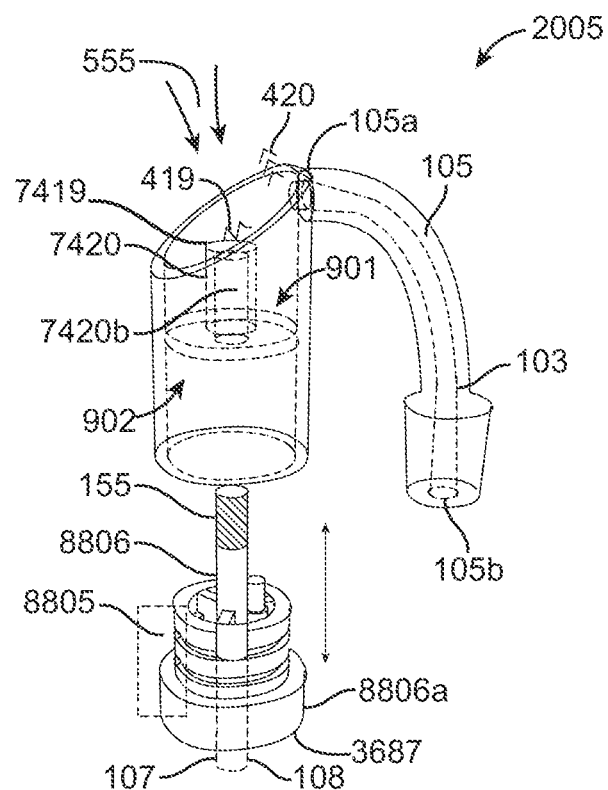
FIG. 4C shows a side view of an inside detail of an example vaporization element that may be used with the example vaporization device shown in FIG. 4A in accordance with an embodiment.

As explained above, the vaporization element 2000 may include a heater section 902 within which a heater unit can be received. FIG. 4C illustrates an example of a vaporization element 2005 and a corresponding heater unit 8805 in accordance with an embodiment. Vaporization element 2005 is an example of a vaporization element 2000 that may be used with various embodiments of the vaporization devices described herein above.

As shown in FIG. 4C, vaporization element 2005 includes a vaporization section 901 and a heater section 902. A heater unit 8806 can be received within the heater section 902. In FIG. 4C, the heater unit 8806 is shown removed from heater section 903. The vaporization element 2005 also includes a hollow member 105 fluidly coupled to the vaporization section 901.

The heater section 902 of the vaporization element 2005 can be shaped to receive the heater unit 8806. The heater unit 8806 may also include a housing 8806*a* at least partially enclosing the heater unit 8806. For example, the housing 8806*a* may substantially enclose the portions of heater unit 8806 positioned within the heater section 902 (and any that remain exposed when the heater unit 8806 is positioned within the heater section 902).

The housing 8806*a* may include heater section engagement members 8805. The heater section engagement members 8805 may frictionally engage the inner side walls of the heater section 902. The may retain the heater unit within the heater section 902.

As shown in FIG. 4C, the resistive heater 155 may extend past the housing 8806*a*. Accordingly, the resistive heater 155 may extend into the vaporization section when the heater unit is positioned within the heater section 902.

The vaporization element 2005 includes a phyto material contact element 7419. The phyto material contact element 7419 can define a phyto material contact surface 7420 positioned in the vaporization section 901. The phyto material contact surface 7420 can be provided by a first side of the phyto material contact element 7419 (i.e. the side facing into the vaporization section 901). As shown in FIG. 4C, the vapor inlet 105*a* may at least partially face the phyto material contact surface 7420.

As shown in vaporization element 2005, the phyto material contact element 7419 can extend or protrude into the vaporization section 901. The phyto material contact element 7419 can extend from a substantially closed second end 901*d* of the vaporization section 901 towards the first end 901*c*. This can raise the phyto material contact surface 7420 towards the vapor inlet 105*a* of hollow member 105. As a result, vapor generated from extract 419 positioned on the phyto material contact surface 7420 can be emitted in close proximity to the fluid pathway 103.

The second side 7420*b* of the phyto material contact element 7419 can define an inner cavity within which the resistive heater 155 can be received. The resistive heater 155 may be positioned within this cavity proximate to (and even in contact with) the second side 7420*b* of the phyto material contact element 7419. The resistive heater 155 can then operate to heat the phyto material contact element 7419, and in turn the phyto material contact surface 7420.

Figure 7A:
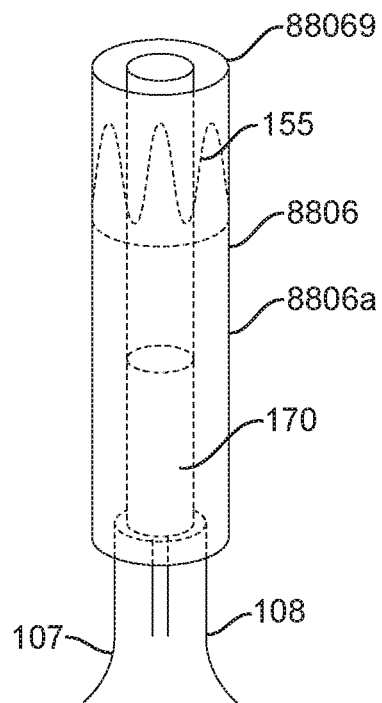
FIG. 7A shows a perspective side view of an example heater for a vaporization device in accordance with an embodiment.

In some embodiments, the resistive heater 155 may be provided as part of a heating rod 88069 heater unit (see, for example FIG. 7A). The heating rod 88069 may be a ceramic rod heater for instance. The heating rod 88069 may have a substantially cylindrical or tubular shape. In some cases, the heating rod 88069 may also include a temperature sensor 170.

Figure 7B:
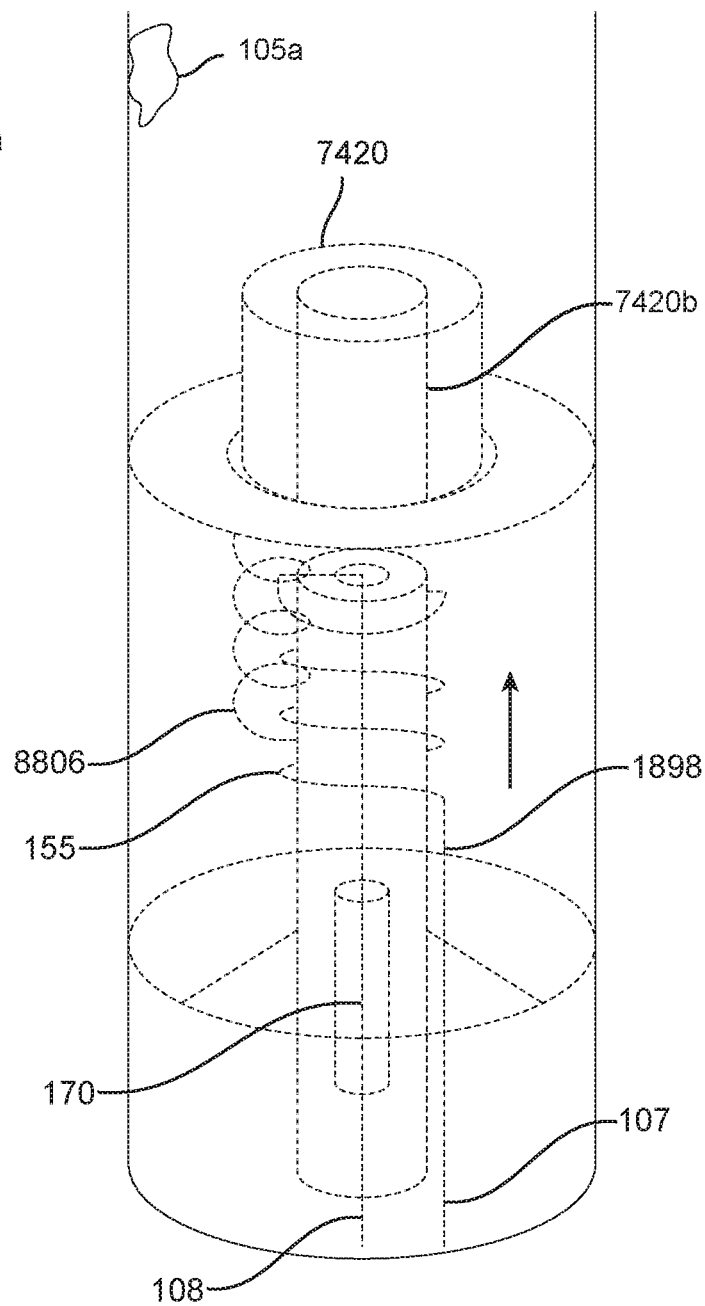
FIG. 7B shows another perspective side view of the example heater shown in FIG. 7A.

As shown in FIG. 7B, the heater unit 8806 can include a resistive heater 155 wrapped about a ceramic tube 1898 to form a tubular heater. The heater unit 8806 may be positioned in a vaporization element with the resistive heater positioned proximate to (potentially contacting) the second side 7420*b* of the phyto material contact element.

Another example vaporization element 7000 is shown in FIG. 6C. As shown by vaporization element 7000, a temperature sensor 170 can be provided in thermal communication with the heating element 8806. The temperature sensor 170 may have a temperature signal output port 170*a* that can be coupled to control circuit such as control circuit 113 and/or 114. The temperature signals from temperature sensor 170 can be used to determine a temperature of the phyto material contact surface 7420.

As shown in vaporization element 7000, the phyto material contact element 7419 can be disposed between the resistive heater 155 and the phyto material extract 419. The phyto material contact element 7419 can define a phyto material contact surface 7420 that can contact the extract 419. The phyto material contact element 7419 may receive thermal energy from the resistive heater 155 on a second side thereof 7420*b*. The phyto material contact element 7419 can transmit at least a portion of the received thermal energy into the phyto material 419 disposed on the phyto material contact surface 7420. This thermal energy can heat the phyto material contact surface 7420 to a predetermined vaporization temperature and vaporize extract positioned thereon.

In some examples, the phyto material contact element 7419 may be manufactured of glass while the resistive heater 155 can be formed by a ceramic heater 155a. In some cases, the phyto material contact element 7419 may be formed using materials with greater heat transfer, such as silicon carbide for example. The ceramic heater 155a may heat the phyto material extract 419 through the phyto material contact element 7419 without contacting the extract 419 directly.

As described above in reference to FIG. 4C, the heater unit 8806 can be removably inserted into a heater section 902 of the vaporization element 7000. For instance, the heater unit 8806 can include engaging members that can form a frictional coupling with the inside surfaces of the heater section 902.

The heater unit 8806 can include a heating element housing 8806a. At least one O-ring 8806b (e.g. silicone rubber) can be disposed about the heating element housing 8806a. The O-ring 8806b can frictionally engage a portion of the heater section 902. This may allow the heater unit 8806 to be inserted into the heater section 902 with the resistive heater 155 proximate the second side 7420b of the phyto material contact element 7419.

In some embodiments, the phyto material contact surface 7419 can be formed from ceramic and the elongated hollow member 105 may include ceramic materials. Selecting a low thermal conductivity material may be preferable for the construction of components of the vaporization element 700 as this can reduce thermal energy transfer from the phyto material contact element 7419 to other parts of the vaporization element 7000, such as hollow member 105 and the walls of the vaporization section 901 and heater section 902. Having the heating element housing 8806a releasably coupled to the vaporization element 7000 may allow the vaporization element 7000 to be more easily cleaned. For instance, isopropyl alcohol, or high heat, may be used to clean the vaporization element 7000 when the heater unit 8806 is removed.

Manufacturing the elongated member 105 from ceramic or glass or quartz may also allow for easy cleaning thereof. Ceramic and glass materials do not typically stain when used for vaporization of phyto material extracts 419. Furthermore, using a low thermal conductivity material for elongated member 105 may facilitate retaining the second end 105b at a substantially cooler temperature than the first end 105a. This may allow the elongated hollow member 105 to provide additional cooling to the vapor 421 and ambient air 555 as it propagates therethrough.

Another example of a vaporization element 8000 is shown in FIG. 6J. Vaporization element 8000 has a modified heater unit 8806 (see FIG. 6K) and a modified phyto material contact element 7421 as compared to vaporization element 7000.

The heater unit 8806 includes a temperature sensor 170. The temperature sensor 170 may be maintained within the housing 8806a of the heater unit 8806 and positioned proximate to the phyto material contact element 7421 when the heater unit 8806 is positioned in the heater section of the vaporization element 8000. As shown in FIG. 6K, in some embodiments the heater unit 8806 may also include a control circuit 114.

As shown in vaporization element 8000, the resistive heater 155 can be provided in the form of a spiral or a pancake coil heater 8806b (see e.g. FIG. 6K). The coil heater 8806b can be positioned proximate to a second side of the phyto material contact element 7421. The coil heater 8806b can heat the phyto material contact element 7421 to transfer energy to phyto material contact surface 7421a. Providing the resistive heater 155 as a spiral or pancake coil can provide a large surface area for heating the phyto material contact element 7421.

Figure 7C:
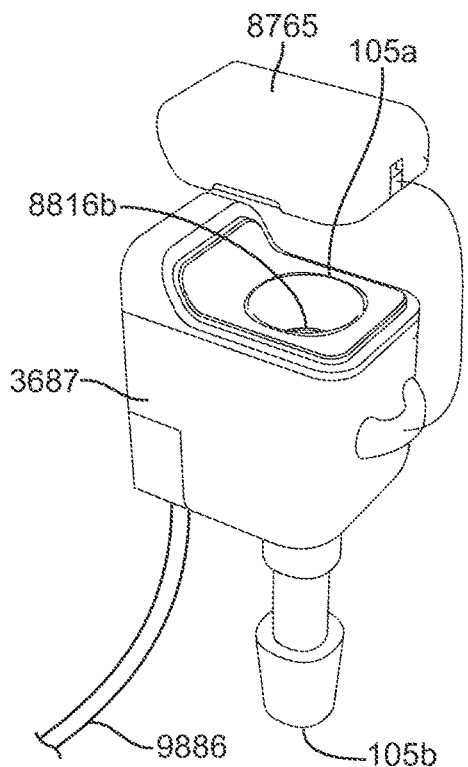
FIG. 7C shows a top perspective view of another example vaporization element in accordance with an embodiment.
Figure 7D:
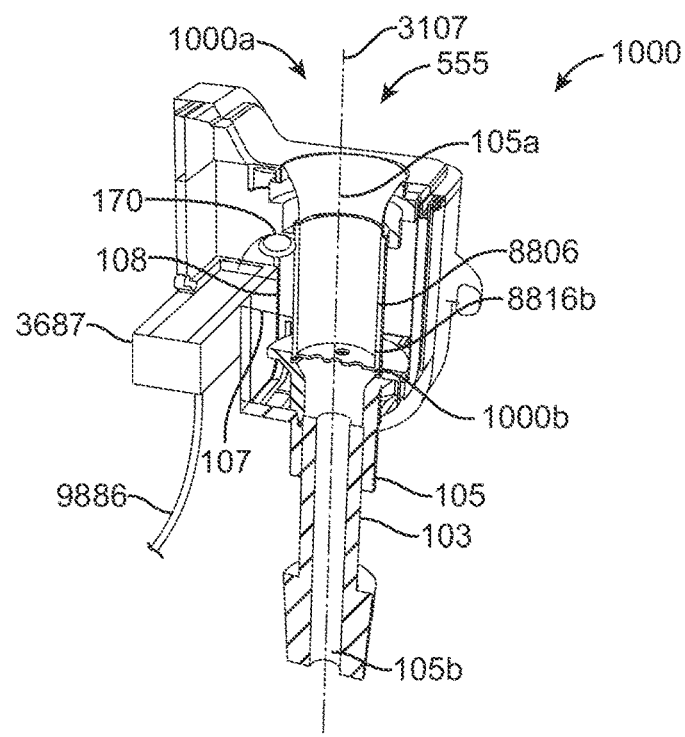
FIG. 7D shows a cut-away perspective side view of the vaporization element shown in FIG. 7C.

Another example of a vaporization element 1100 is shown in FIGS. 7C and 7D. As shown in the example of vaporization element 1100, the heater unit 8806 can include a cup heater 8816b. Cup heater 8816b may be manufactured using ceramic materials Vaporization element 1100 may also be referred to as a leaf attachment vaporization element. The vaporization element 1100 may include a substantially enclosed housing in which the ceramic cup heater 8816b is positioned.

The cup heater 8816b may have a first, open end 1100a. Phyto material and/or phyto material extract can be inserted into the cup heater 8816b via the first open end 1100a. The vaporization element 1100 may include a removable lid 8765. The lid 8765 may be removed when loading phyto material or extract into the heater unit 8806 or removing residue from the vaporization element 1100. The lid 8765 can be positioned in a closed position when the phyto material or extract is being vaporized. This may facilitate heating of the heater unit 8806 to the predetermined vaporization temperature (and maintaining the heater unit 8806 at that temperature). When the lid 8765 is in the closed position, the vaporization element 1100 may still provide an ambient air inlet to allow ambient air to flow into the heater unit 8806 and become entrained with the vapor into the fluid pathway 103.

The second end 1100b of the heater 8816b may define a partially perforated phyto material holder portion. The second end 1100b of the heater may include a screen or filter that can support phyto material and/or phyto material extract while allowing ambient air and vapor to propagate therethrough.

The vaporization element 1100 can define a fluid pathway 3103 with a fluid inlet 105a that extends from the first end 1000a through the heater 8816b to a fluid outlet 105b. The screen or filter at the second end 1000b of the heater unit 8806 may prevent the phyto material, or substantially all of the phyto material, from passing through the fluid pathway and out the fluid outlet 105b.

In vaporization element 1100, the heater 8816b can be positioned to surround the phyto material or phyto material extract positioned in the vaporization element 1100. The heating element 8816b can heat the phyto material (or extract) from the sides. Thermal energy can propagate from the heating element 8816b into the phyto material 420 (or extract) and generate vapor. Ambient air entering the vaporization element 1100 along with the vapor can pass through the perforated second end 1100b and along the fluid pathway 103 to be inhaled.

Figure 7E:
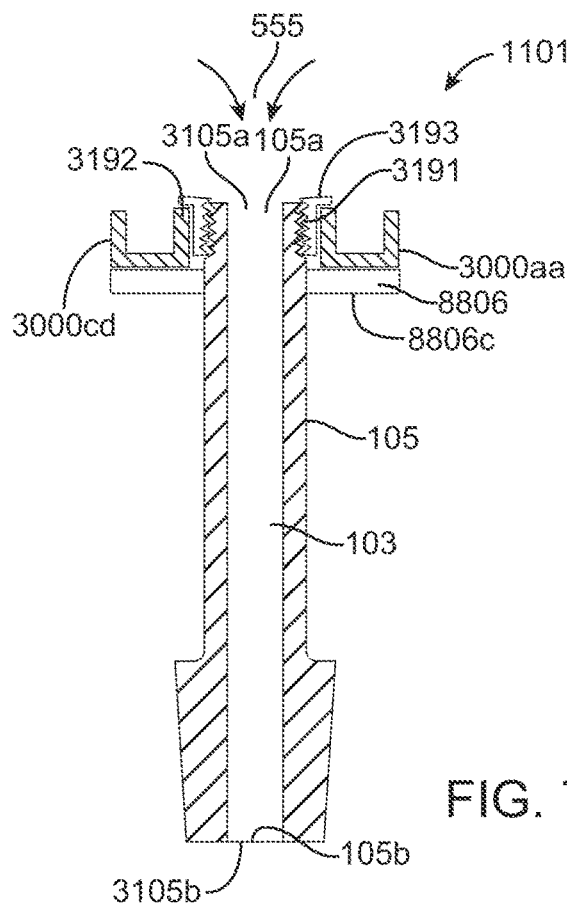
FIG. 7E shows a cut-away side view of another example vaporization element in accordance with an embodiment.

Another example embodiment of a vaporization element 1101 is shown in FIG. 7E. As shown in vaporization element 1101, the heating element 106 may be provided by a removable cup or platform or holder unit 3000ca. The removable holder unit 3000ca may be manufactured from various materials, such as ceramic or glass or gold or platinum or silver. The removable cup 3000ca can be positioned on the vaporization element 1101 in thermal communication with the heater unit 8806.

Figure 7F:
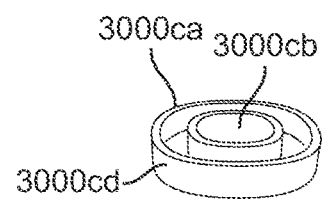
FIG. 7F shows a perspective view of an example contact element for a vaporization element in accordance with an embodiment.

The removable holder portion 3000ca can be in the form of a semi-toroid (see e.g. FIG. 7F). The holder portion 3000ca has a central through-hole 3000cb that can be shaped to correspond to a central fluid pathway 103 defined by vaporization element 1101. The fluid pathway 103 can extend from the first end 105*a* of the vaporization element 1101 to the second end 105*b* thereof through the center hole 3000*cb*.

The central through-hole of the holder portion 3000*ca* can be defined by the inner sidewalls of the holder portion. The holder portion 3000*ca* can also include outer sidewalls 3000*cd* defining an outer circumference of the holder portion 3000*ca*.

In some cases, the vaporization element 1101 may include a threaded coupling 3191 for the holder portion 3000*ca*. The threaded coupling 3191 may include a spring 3192 to allow for thermal expansion along the fluid pathway 103. The removable cup 3000*ca* may be detachably attached to the vaporization element 1100 on top of the annular heater 8806 with the spring 3192 engaging a hollow nut 3193. The spring 3192 and nut 3193 may interact to press the removable cup 3000*ca* against the annular heater 8806*c*.

Figure 7G:
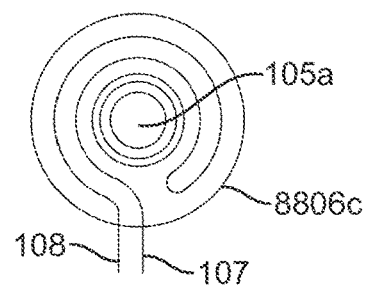
FIG. 7G shows a top view of an example heating element that may be used with the vaporization element shown in FIG. 7E in accordance with an embodiment.

FIG. 7G illustrates the annular heater 8806*c* from a top view. The annular heater 8806*c* may operate to heat phyto material or extract positioned on the removable cup 3300*ca* in a manner analogous to heater units 8806 described herein above.

Figure 7H:
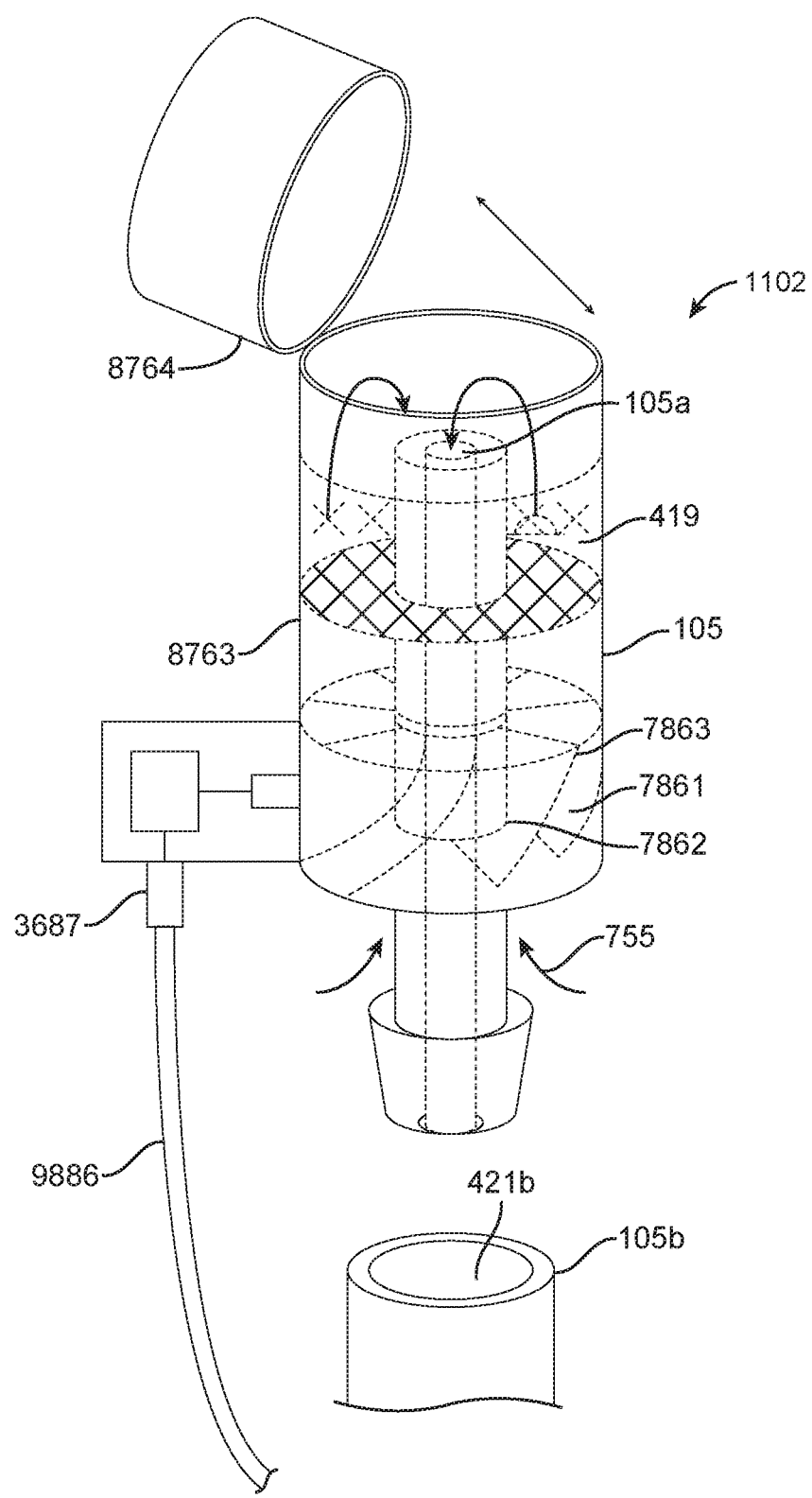
FIG. 7H shows another example vaporization element in accordance with an example embodiment.

Another example embodiment of a vaporization element 1102 is shown in FIG. 7H. As shown by vaporization element 1102, in some embodiments the heater unit 8806 may include a convection heater 7861.

The convection heater 7861 may have a heater core 7862 (e.g. of ceramic) coupled to a plurality of extensions or fins 7863. The heater core 7862 may heat the fins 7863 and ambient air 755 passing through the vaporization element 1102. The heated ambient air 755 can then pass over the phyto material or extract positioned in the vaporization element 1102 downstream of the convection heater 7861. For instance, vaporization element 1102 may include a screen or perforated contact surface to support the phyto material or extract. The heated air can transfer thermal energy to the phyto material or extract to generate vapor. The vapor may then enter the fluid pathway 103 at the vapor inlet 105*a*.

As shown, the vaporization element 1102 may include a detachable lid 8764. The lid 8764 may be movable to an open position in which access is provided to the holder portion of the vaporization element 1102. The lid 8764 may also be movable to a closed position in which the end of the vaporization element 1102 proximate the vapor inlet 105*a* is closed. This may ensure that vapor enters the fluid pathway 103.

Referring now to FIGS. 9A-9C, shown therein is another example of a vaporization element 900. As shown, vaporization element 900 can include a cylindrical vaporization portion 901. The vaporization portion 901 can be configured to receive phyto material or extract to be vaporized and to generate vapor therefrom.

The vaporization element 900 can also include a cylindrical heater portion 902. The heater portion 902 can be shaped to receive a heater unit, such as the heater units described herein above, to apply thermal energy to the vaporization portion 901.

The vaporization element 900 can include a hollow member 105. The hollow member 105 can define a fluid pathway 103 extending from a first end 105*a* to a second end 105*b*. The first end 105*a* can be arranged as a vapor inlet facing into the vaporization portion 901. The second end 105*b* of the fluid pathway can be configured to be fluidly coupled with an input port 421*b* of a vapor processing device such as a water pipe.

As shown in FIG. 9A, the cylindrical vaporization section 901 may have a first inner diameter defined by inner walls 901*a*. The cylindrical vaporization section 901 may also have a first outer diameter defined by outer walls 901*b*. As should be apparent, the first outer diameter can be larger than the first inner diameter.

The cylindrical vaporization section 901 may extend from a vaporization section first end 901*c* to a vaporization section second end 901*d*. The vaporization section first end 901*c* may be open or partially open to allow phyto material or extract to be positioned in the phyto material section 901.

The vaporization section second end 901*d* may include a phyto material contact surface 7420. The phyto material or extract may be positioned on the phyto material contact surface 7420 to be vaporized.

The vaporization section 901 may define a vaporization section volume. The vaporization section volume may be defined as the volume bounded by the vaporization section first end 901*c*, vaporization section second end 901*d* and the first inner diameter (i.e. inner walls 901*a*). The vapor inlet 105*a* can be fluidly coupled to the vaporization section volume.

As shown, the vapor inlet 105*a* may be positioned proximate the first end 901*c* of the vaporization section 901. This may allow the vapor generated from heating the phyto material or extract to rise towards the vapor inlet 105*a*.

The cylindrical heater section 902 can include a second inner diameter defined by inner sidewalls 902*a*. The cylindrical heater section can also include a second outer diameter defined by outer sidewalls 902*b*. As should be apparent, the second outer diameter can be larger than the second inner diameter.

The cylindrical heater section 902 can extend from a heater section first end 902*c* to a heater section second end 902*d*. The cylindrical heater section 902 can define a heater section volume bounded by the first end 902*c*, second end 902*d* and inner sidewalls 902*a*. The heater section volume can be arranged to receive an electrical heater unit.

The vaporization element 900 can also include a phyto material contact element. The phyto material contact element may have a first side positioned at the vaporization section second end 901*d*. A second side of the phyto material contact element can be positioned at the heater section first end 902*c*. The first side of the phyto material contact element may define a phyto material contact surface 9420. The phyto material contact element may provide thermal communication between the vaporization section second end 901*d* and the heater section first end 902*c*.

As shown in FIG. 9C, a heater unit 8806 can be disposed within the heater section 902. An electrical heater can be positioned proximate the heater section first end 902*c*, e.g. adjacent to or in contact with the phyto material contact element. The heater unit 8806 may be implemented in various ways as described herein above.

As shown in FIG. 9B, the cylindrical heater section 902 and the cylindrical vaporization section 901 may be coaxial. In some embodiments, the diameters of the cylindrical heater section 902 and the cylindrical vaporization section 901 may be similar, or substantially equal (e.g. as shown in FIG. 9B). For instance, a cross section of the cylindrical heater section 902 and the cylindrical vaporization section 901 along a coaxial axis 9021 may resemble a letter H.

In other embodiments, the heater section 902 may have an inner diameter that is greater than the inner diameter of the vaporization section 901. In some cases, the inner diameter of the heater section 902 may be similar, or approximately equal to, the outer diameter of the vaporization section 901.

Having a wider heater section 902 may allow the heater unit 8806 to heat the phyto material contact element directly as well as apply heat to sidewalls 8661 of the vaporization section 901. Accordingly, phyto material or extract may be heated by the sidewalls of the vaporization section 901 in addition to the phyto material contact surface 7420.

Heat from the heating unit 8806 may be directed into the walls of the vaporization section 901. This may allow extract to be applied to the inner sidewalls of the vaporization section 901 as well as the phyto material contact surface 7420 to provide a wide surface area for vaporization. Extract may be applied to the vaporization section 901 in a circular manner so that it may equally dissipate onto the inside walls to facilitate vaporization thereof.

The cylindrical heater section may form an insulative skirt. The insulative skirt may substantially surround the phyto material contact element and assist in holding the heating unit 8806 around the phyto material contact element.

In some cases, the thickness of the sidewalls of the heater section 902 may be greater than the thickness of the sidewalls of the vaporization section 901. This may allow the heater section 902 to provide greater insulative capabilities around the heater unit 8806 while heat can be more easily transferred into the vaporization section 901.

In use, the vaporization element 900 may be configured so that the axis along which the vaporization section 901 and heater section 902 extend is substantially perpendicular to a direction of gravity. Accordingly, heat from the heater unit 8806 may be inclined to travel upwards from the heater section 902 to the vaporization section 901. This may also encourage the vapor to travel upwards to vapor inlet 105a.

In some embodiments, the components of vaporization element 900 may be manufactured using various materials such as quartz glass or other glass or ceramic material for example. In some embodiments the phyto material contact element and/or the vaporization section 901 may be manufactured using silicon carbide. As silicon carbide provides higher heat conductivity than quartz glass, this may encourage the transfer of heat into the vaporization section 901. Other examples of ceramic materials that may be used include Aluminum Nitride, Sapphire, Alumina, and Silicon Nitride.

As explained herein above, the heater unit 8806 may include engagement members 8123 that may engage the inner sidewalls of the heater section. In some cases, the heater unit 8806 may include a pivotable or rotatable portion. The pivotable or rotatable portion may allow the heater 155 to adjust for variations in the orientation of the second side of the phyto material contact element (see e.g. FIG. 10F-G). This may assist in maintaining the heating unit 8806 proximate the phyto material contact element.

In some embodiments, a heat shield 157 (e.g. ceramic or metal) may be disposed between the heating unit 8806 and the second inner diameter of the heater section 902. The heat shield 157 may reflect a portion of heat radiated from the heater 155 to reduce or prevent heat dissipation out the sidewalls of the heater section 902.

FIGS. 10A-10I illustrate another example embodiment of a vaporization element 2006. In vaporization element 2006, the vaporization section 901 extends partially into the heater section 902. That is, the inner sidewalls 902w of the heater section 902 surround a portion of the vaporization section proximate the second end 901d.

The first end 902c of the heater section 902 can define an insulative skirt 902s surrounding the second end 901d of the vaporization section 901. This may provide facilitate the transfer of heat into the second end 901d of the vaporization section 901, and into the phyto material contact element as well. Additionally, this may facilitate maintaining the phyto material contact surface 7420 (and inner side walls of the vaporization section 901 proximate the second end 901d) at the predetermined vaporization temperature.

The second end 901d of the vaporization section 901 may define a phyto material vaporization region 901v. The phyto material vaporization region may be insulated by the inner sidewalls 90ww of the heater section. The inner sidewalls 902w of the heater section 902 may be manufactured using materials with low thermal conductivity such as glass. Accordingly, heat from the heater unit 8806 can rise into this insulative skirt region 902s and maintain the vaporization region at a more constant temperature. This may provide a combined conduction and convection heater unit 8806, as the phyto material contact element 7419 can be heated by conduction and the inner sidewalls of the vaporization section 901 can be heated using a combination of convection and conduction (from the phyto material contact element 7419).

In some examples, the phyto material contact element 7419 may be formed integrally with the vaporization section 901 as shown here. This may facilitate construction of the vaporization element 2006.

In other embodiments, the phyto material contact element 7419 may be a separate component that may be inserted at the second end 901d of the vaporization element (see e.g. FIG. 11A). This may allow the phyto material contact element 7419 to be constructed using materials that provide greater heat transfer from the heater section 902 to the vaporization section 901.

As shown, a heater unit 8806 can be positioned in the heater section 902 proximate the phyto material contact element 7419. Heat from the heater unit 8806 can heat the phyto material contact element directly. Heat from the heater unit 8806 can also heat the air surrounding the second end 901d of the vaporization section 901 (as well as the walls of the vaporization section 901 and heater section 902).

Figure 10A:
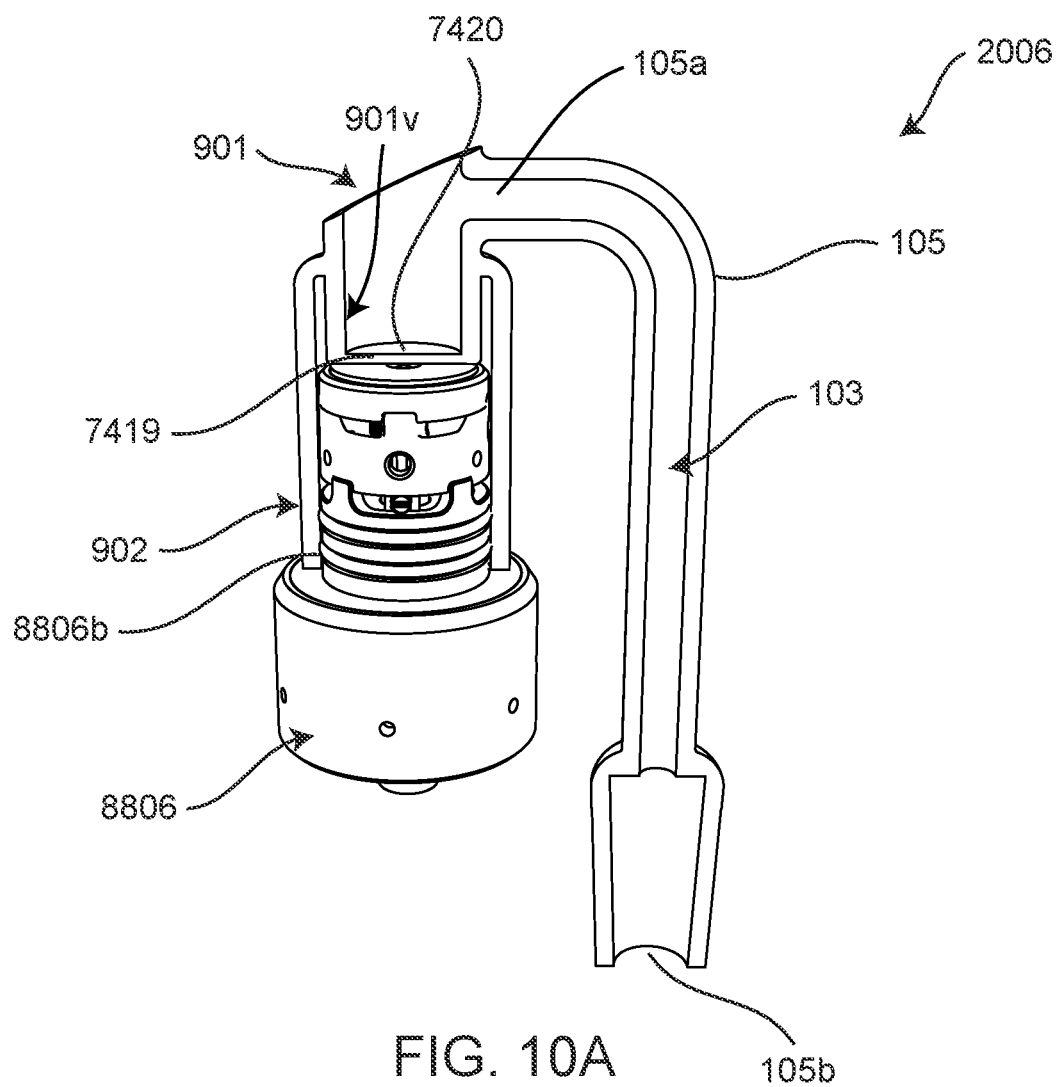
FIG. 10A shows a cut-away side view of an example vaporization element in accordance with an embodiment.
Figure 10B:
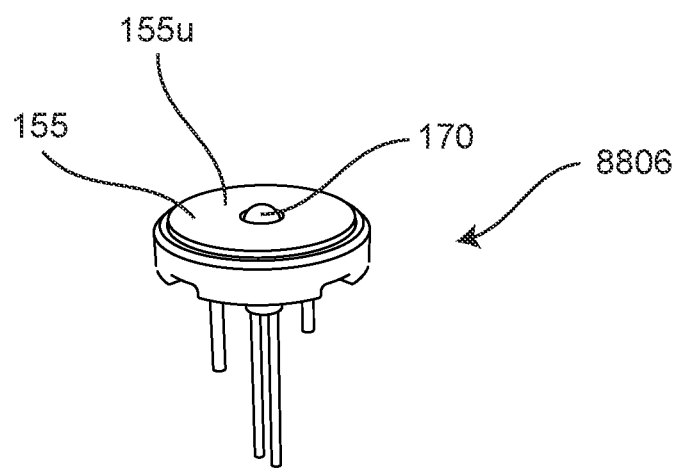
FIG. 10B shows a perspective view of an example heater and temperature sensor component that may be used with the vaporization element shown in FIG. 10A in accordance with an embodiment.
Figure 10C:
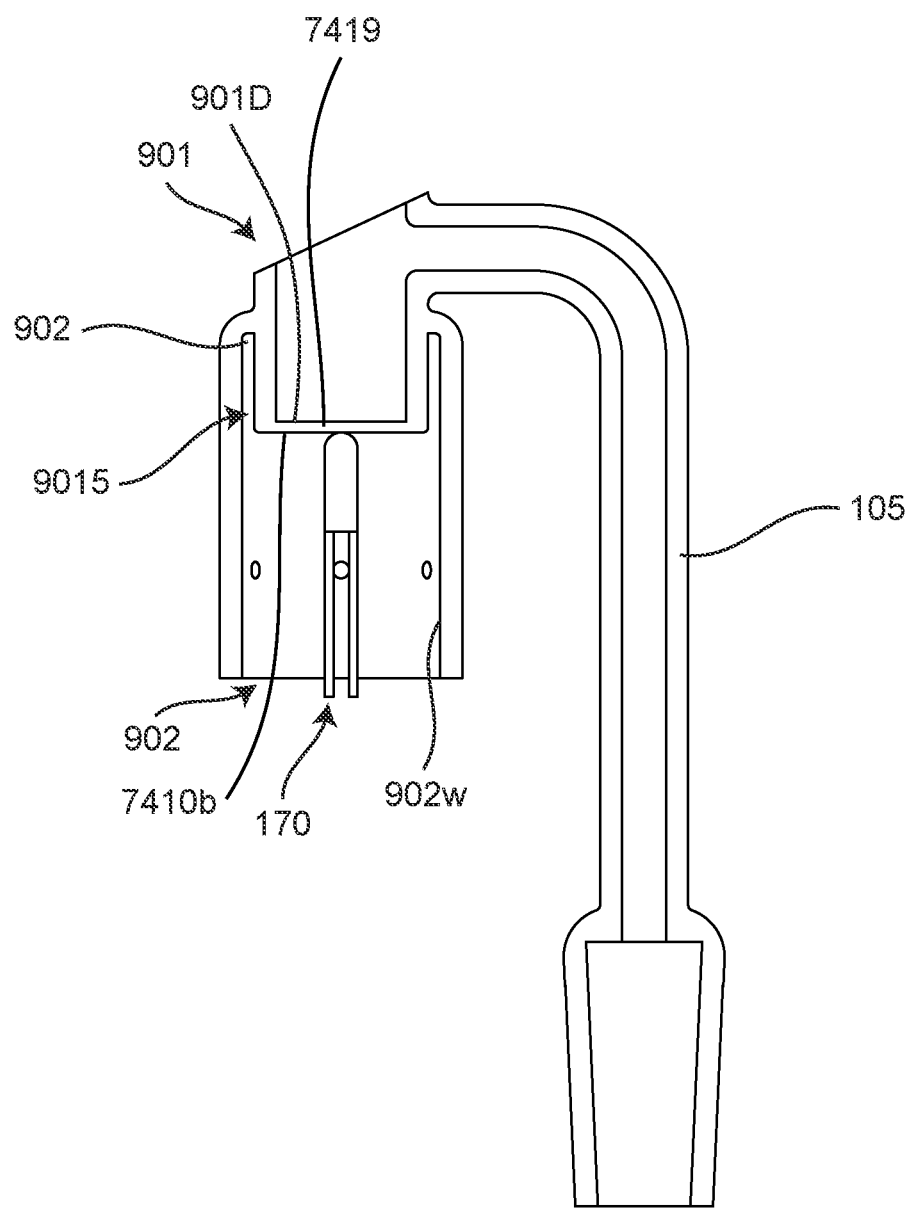
FIG. 10C shows a partial cut-away side view of the example vaporization element shown in FIG. 10A showing the temperature sensor of FIG. 10B.
Figure 10D:
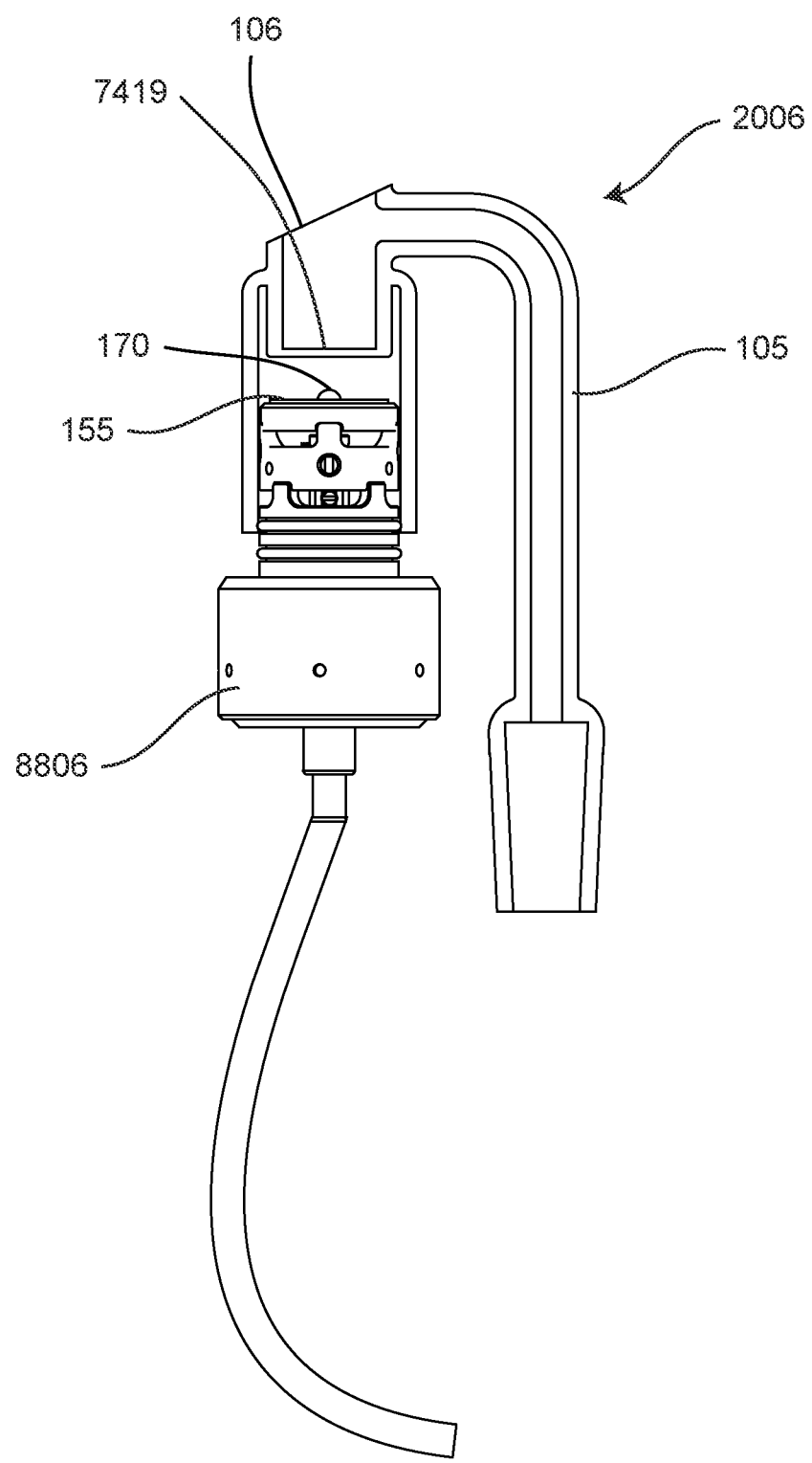
FIG. 10D shows a partial cut-away side view of the example vaporization element shown in FIG. 10A with the heater unit and temperature sensor component in a first position.
Figure 10E:
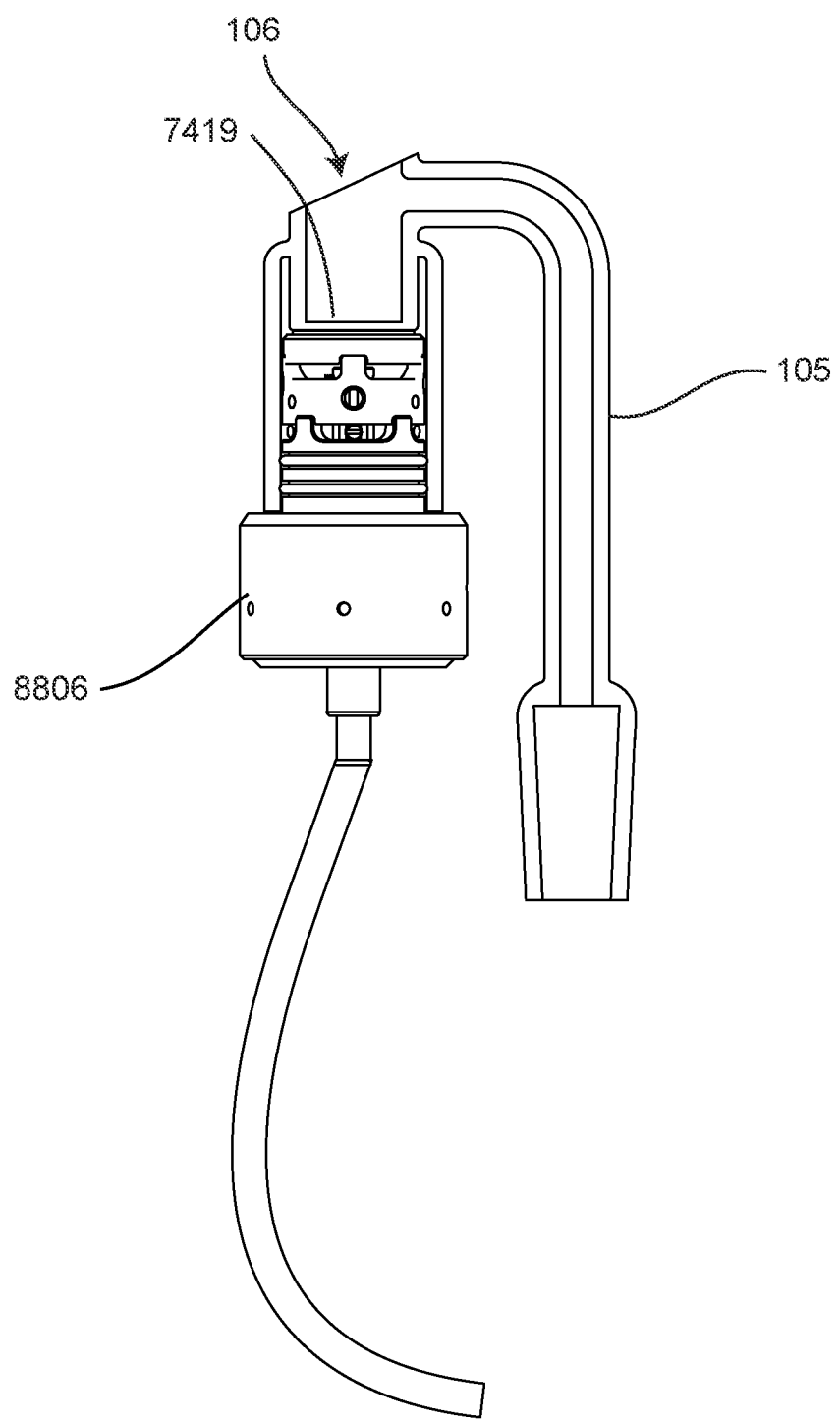
FIG. 10E shows a partial cut-away side view of the example vaporization element shown in FIG. 10A with the heater and temperature sensor component in a second position.
Figure 10F:
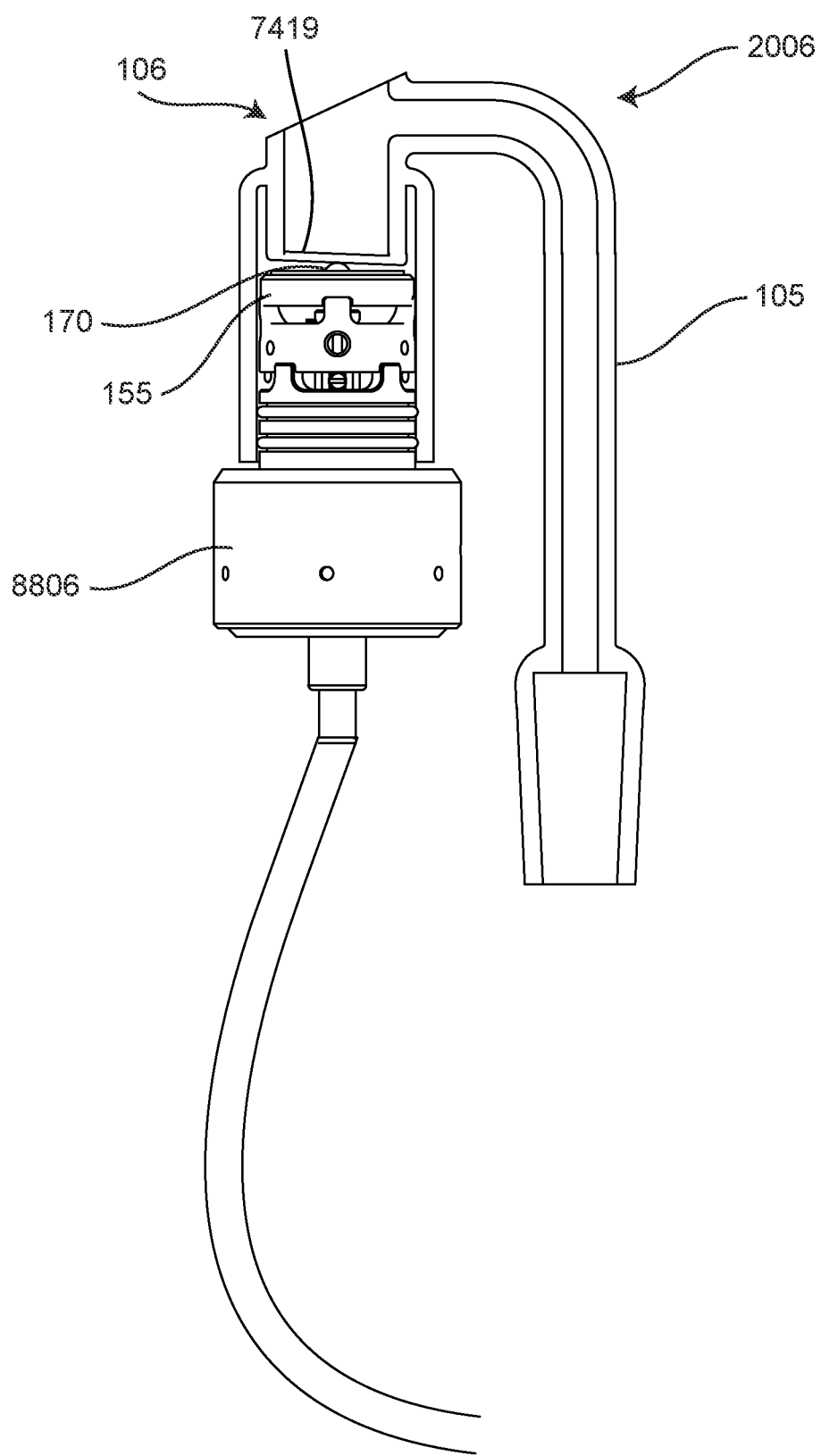
FIG. 10F shows a partial cut-away side view of another example vaporization element with an example heater component in the first position.
Figure 10G:
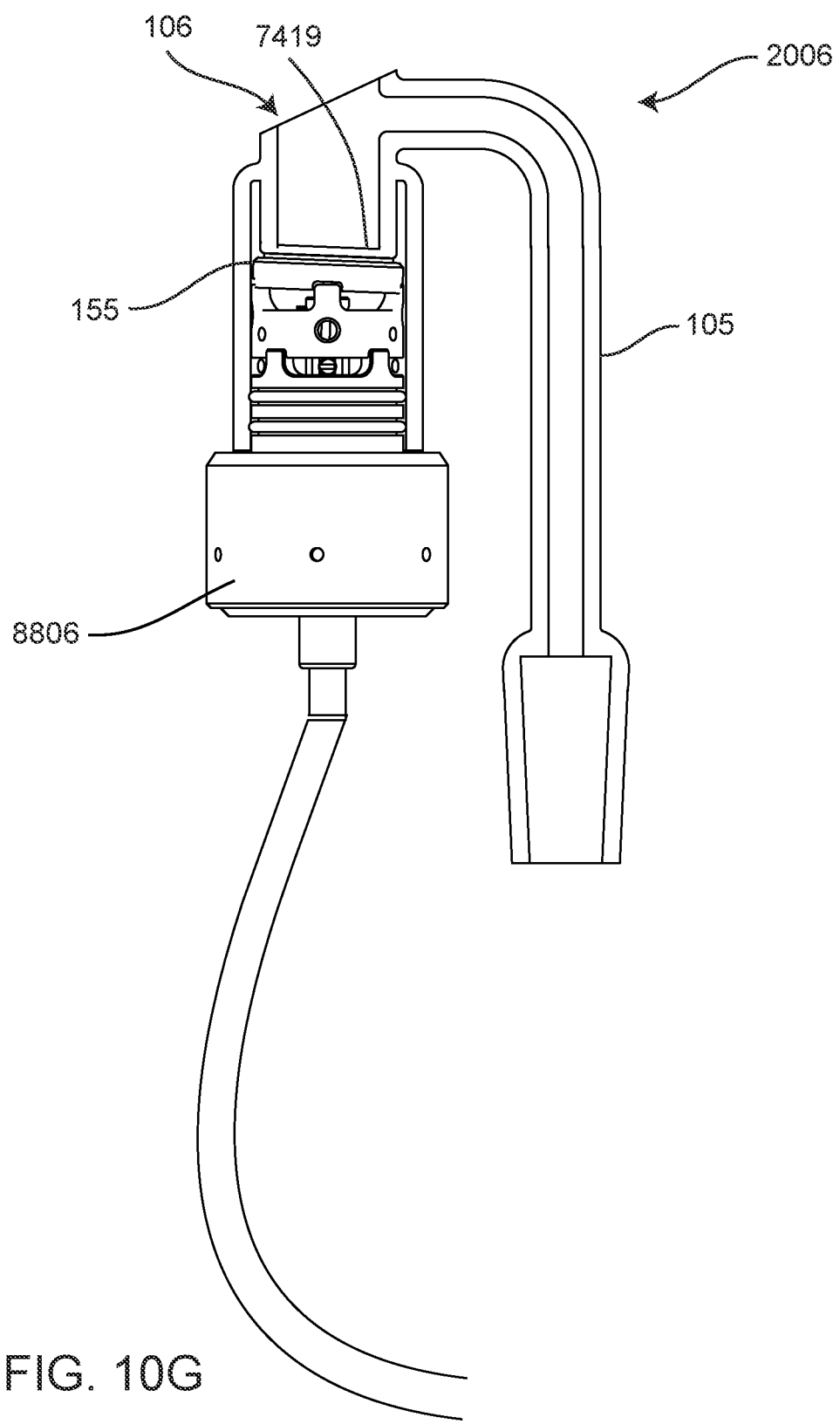
FIG. 10G shows a partial cut-away side view of the example vaporization element shown in FIG. 10F with the heater component of FIG. 10F in the second position.

As shown in FIGS. 10B and 10D, the heater unit 8806 can include a temperature sensor 170. The temperature sensor 170 may protrude through an upper surface 155u of the heater 155 towards the phyto material contact element 7419. The temperature sensor 170 may contact the phyto material contact element 7419 when the heater unit 8806 is positioned in the heater section 902. The temperature sensor 170 may be retractable (e.g. spring-loaded) so that it does not interfere with the placement of the heater unit 8806 proximate the phyto material contact element while still maintaining a thermal coupling with the phyto material contact element 7419.

In some embodiments, the heater unit 8806 may include a heat activated pigmentation. The pigmentation may be selected so that at room temperature the heater unit is a first color (green) and when heated to a vaporization temperature (e.g. 350 F to 750 F) the pigmentation can change to a variety of different color as the temperature increases (ex: brown). The user can observe the color of the heater unit 8806 which can provide a visual indication that the heater unit 8806 (and surrounding vaporization section 901/heater section 902) is hot. This may provide a visual indication even in the absence of power to the heater unit 8806. Optionally, a color changing pigment may be applied proximate the heater section 902 to provide a further warning visual indication to the end user that elements are hot.

In some embodiments, the heater unit 8806 may use a coil or stamped resistive heater 155. The resistive heater 155 may glow when heated to a vaporization temperature. A vaporization element that is partially or fully transparent may facilitate observation of the heat indicators.

In some embodiments, the heater unit may include a pivotal coupling for the heater 155 and temperature sensor 170. This may ensure that the heater remains proximate to the phyto material contact element 7419 even if there are discrepancies in manufacturing. For instance, the heater may have a pivot range of about +/−5 degrees. This may allow the heater to align itself with the phyto material contact element when the heater unit 8806 is positioned in the heater section 902 (see e.g. FIGS. 10F-10G).

Figure 10H:
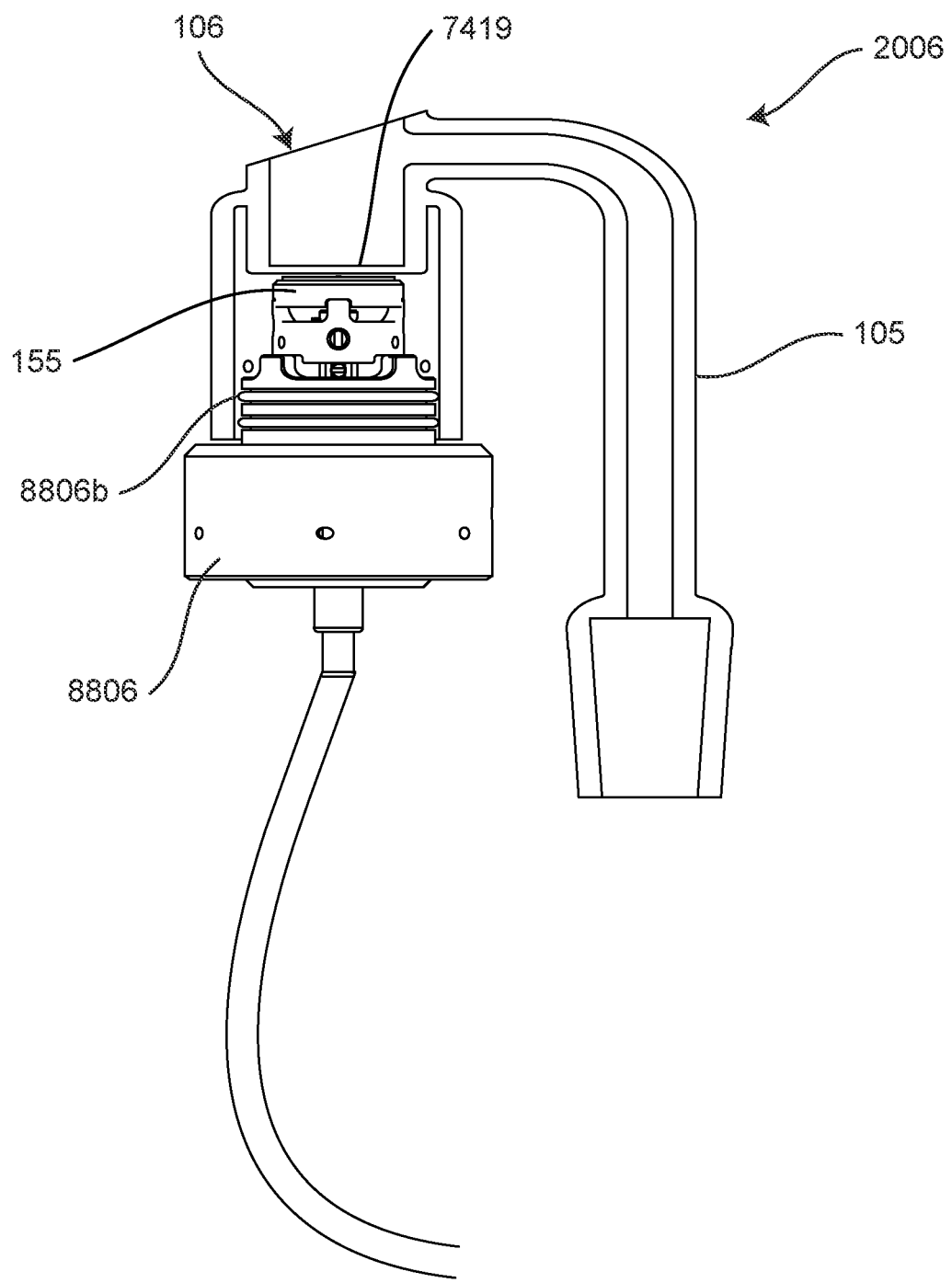
FIG. 10H shows a partial cut-away side view of the example vaporization element shown in FIG. 10A with another example heater component in the second position.

In some embodiments, as shown in FIG. 10H, the heater 155 may contact only a portion of the vaporization section 901 (e.g. only the phyto material contact element 7419).

Figure 10I:
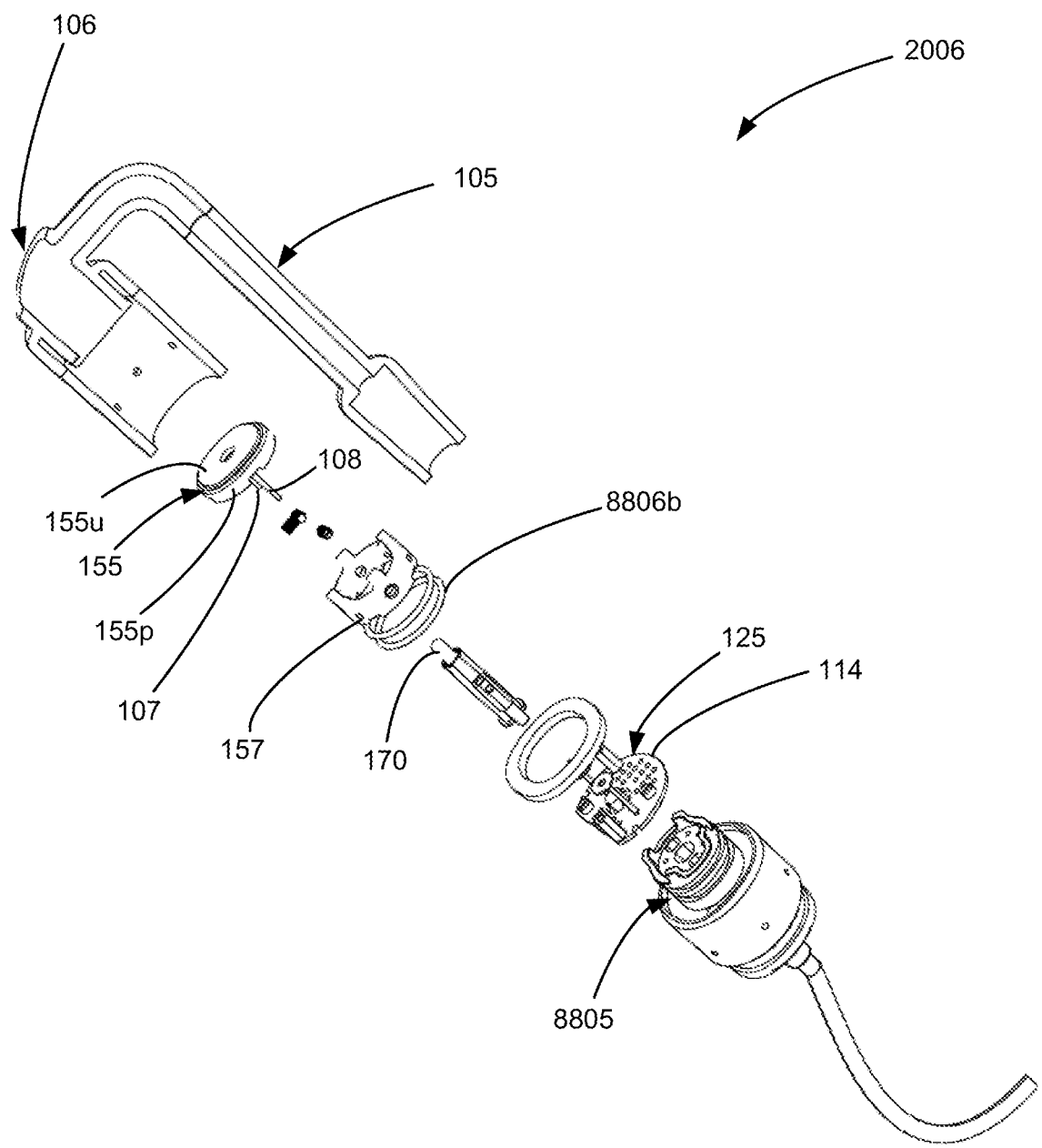
FIG. 10I shows an exploded view of the example vaporization element shown in FIG. 10A.

As shown in FIG. 10I, the heater unit 8806 may include a substantially flat horseshoe heater 155. The heater 155 may also be provided as a wire heater, such as a flat pancake heater. The heater 155 may be retained by a ceramic plate 155*p*. The heater 155 can be coupled to a power source using contacts 107/108.

The temperature sensor 170 can be positioned in the heater unit 8806 to protrude through the heater 155. In some cases, an adjustable temperature sensor calibration unit can be included to calibrate the temperature sensor 170 during use. A printed circuit board 124 that is configured to withstand high temperatures can also be included to provide the second control circuit 114. A heat shield 157 may be provided to surround the heater 155 and reflect heat inwards towards the inner volume of the heater section. The frictional engagement members 8805 may include high temperature O-rings 8806*b*, e.g. made of silicone.

FIGS. 11A and 11B illustrate another example embodiment of a vaporization element 2007. In vaporization element 2007, the phyto material contact element 7419 can be provided as a separate component. The separate phyto material contact element 7419 can be constructed of materials providing greater thermal conductivity, e.g. silicon carbide. This may facilitate the transfer of heat from the heater unit positioned in heater section 902 to the phyto material or extract position in vaporization section 901. The insert 7419 may be usable as a consumable or replaceable component in various embodiments.

As shown in FIG. 11A, the second end 901*d* of the vaporization section 901 can also be open. The phyto material contact element 7419 can be inserted into the heater section 902 and positioned contacting the second end 901*d* of the vaporization section 901. The phyto material contact element 7419 thus inserted can define the phyto material contact surface 7420 on which extract or phyto material can be vaporized.

As mentioned, the insert 7419 may be manufactured from materials having a greater thermal conductivity from the materials used for vaporization section 901 and heater section 902. For instance, the insert 7419 may be manufactured of silicon carbide while the vaporization section 901 and heater section 902 are manufactured of glass or quartz glass. As SiC is inert and conducts heat much better than glass, the insert can get hotter more quickly relative to the adjacent glass. Various other materials may be used to manufacture insert 7419, such as titanium, other ceramics, other metals having greater thermal conductivity than the vaporization section 901 and heater section 902.

The insert 7419 can be secured in place by the heater unit 8806. The heater unit 8806 and insert 7419 may include corresponding engagement members. Accordingly, the heater unit 8806 may frictionally engage the insert 7419 when inserted into the heater section 902.

The insert 7419 may be easily manufactured, particularly as it can be made with a central axis of symmetry. This may facilitate manufacturing using machining and injection molding. Accordingly, the insert 7419 may be easily and inexpensively replace. This may reduce or obviate the need to clean the vaporization device as regularly, because the insert 7419 that provides the phyto material contact surface can simply be replaced when it becomes dirty or stained.

Figure 12A:
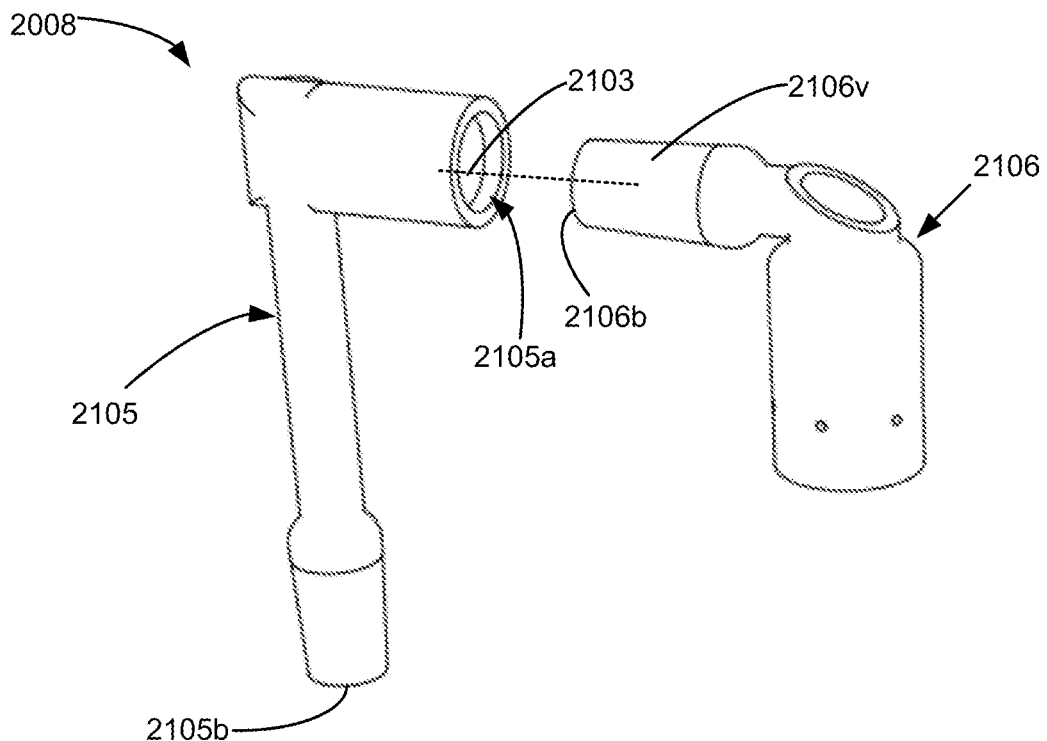
FIG. 12A shows a perspective view of an example vaporization element with an example heating element detached from an example hollow member in accordance with an embodiment.
Figures 12B, 12C:
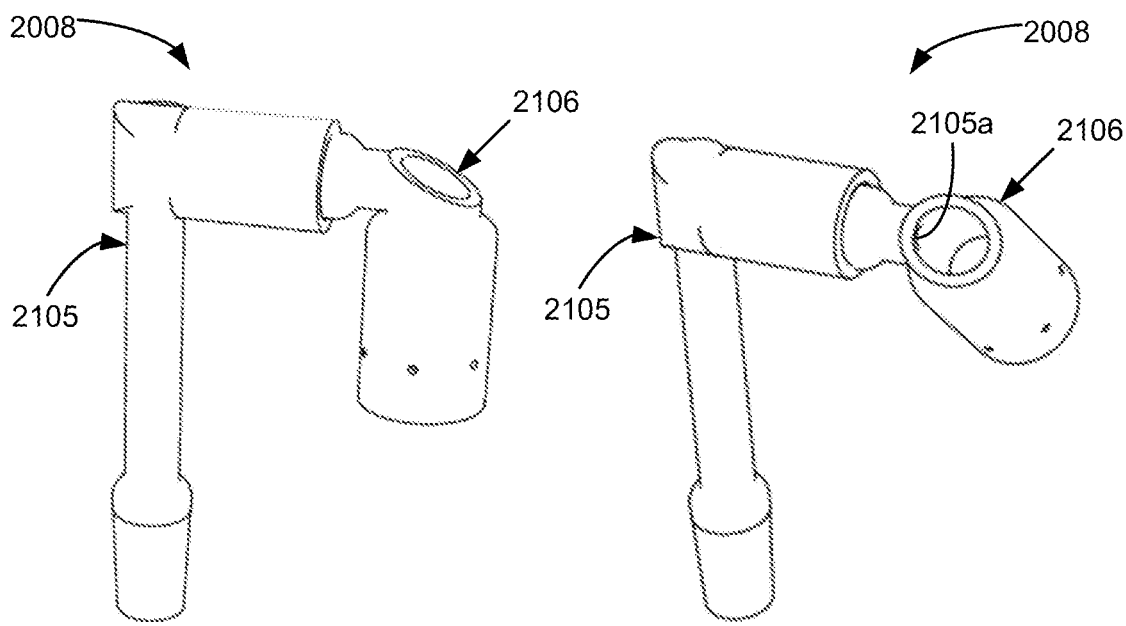
FIG. 12B shows a perspective view of the example vaporization element shown in FIG. 12A with the heating element attached to the hollow member with the heating element in a first position.
FIG. 12C shows a perspective view of the example vaporization element shown in FIG. 12A with the heating element attached to the hollow member with the heating element in a second position.

FIGS. 12A-12C illustrate another example of a vaporization element 2008 in accordance with an embodiment. Vaporization element 2008 is an example of a vaporization element in which the hollow member 2105 is manufactured separately from the heating element 2106. In some embodiments, this may enable the heating element 2106 to be manufactured using different materials from the hollow member 2105.

For example, in some cases the heating member 2106 may be manufactured using materials such as quartz or glass or ceramic. The hollow member 2105 may be manufactured of less brittle materials, such as aluminum for instance.

The heating element 2106 can include a vaporization section and a heating section as described above. The heating element 2106 can also include a heating element channel section 2106*v* defining a vapor pathway. The heating element 2106 can also include a vapor inlet 2106*a* at the entrance to heating element channel section 2106*v*. The heating element vapor channel section 2106*v* can extend from the inlet 2106*a* to the heating element outlet 2106*b*. Vapor generated from extract vaporized in the vaporization section of heating element 2106 can enter the heating element channel section 2106*v* via vapor inlet 2016*a*.

The hollow member 2105 can include a hollow central portion. The hollow central portion may define a hollow member fluid pathway 2103. The fluid pathway 2103 may extend from a first end or vapor inlet 2105*a* of the hollow member 2105 to a second end, or vapor outlet 2105*b*, of the hollow member 2105.

The heating element 2106 can be connected to the hollow member 2105 to provide the vaporization element 2008. The heating element 2106 and hollow member 2105 can be connected with the heating element vapor pathway fluidly coupled to the fluid pathway 2103 defining a continuous fluid pathway from vapor inlet 2106*a* to vapor outlet 2105*b*.

The heating element 2106 may be frictionally engaged with the hollow member 2105. As shown in FIG. 12B, the heating element channel section 2106*v* can be inserted into the fluid pathway 2103. The channel section 2106*v* may frictionally engage the inner side walls of the fluid pathway 2103 to secure the heating element 2106 and hollow member 2105. In some cases, the heating element 2106 may be rotated, as shown in FIG. 12C, to secure the heating element 2106 and hollow member 2105.

The channel section 2106*v* may vary in width along its length to provide a plug when the heating element 2106 is inserted into the hollow member 2105. For instance, the channel section 2106*v* may be narrower at the outlet 2106*b* and increase in width towards the inlet 2106*a*. Additionally or alternatively, the hollow member 2105 may vary in width (e.g. decreasing in width from the inlet 2105*a* inwards) to facilitate frictional engagement of the hollow member 2105 and heating element 2106.

Various other couplings may be used to connect the hollow member 2105 and heating element 2106. For example, the channel section 2106*v* and a portion of fluid pathway 103 may be thread to allow the heating element 2106 to be screwed into the hollow member 2105.

Support Unit for a Vaporization Device

The following is a general description of a support unit for a vaporization device that may be used by itself or in combination with one or more aspects of the disclosure herein, including a vaporization device, a vaporization element for a vaporization device, and/or a method for vaporizing phyto material and/or phyto material extract. The following description contains various features of a support unit for a vaporization device that may be used individually or in any combination or sub-combination.

As explained herein above, FIGS. 3A-3J illustrate an example of a device 1000 for vaporization of phyto material extracts in accordance with an embodiment. A support unit 1001 can be provided that may include one or more components usable with the vaporization device 1000.

For instance, the support unit 1001 may include a control circuit 113. The control circuit 113 may be operable to control power provided to a heater unit of a vaporization element 2000. The control circuit 113 may also receive and process feedback signals from a vaporization element 2000, such as temperature signals from a temperature sensor 170. The control circuit 113 may also generate and output display signals for a user interface usable by a user of the vaporization device.

The support unit 1001 may also include one or more securement mechanisms for a vapor processing device. The securement mechanisms may be used to secure a vapor processing device to the support unit 1001. In some cases, the securement mechanisms can be used to maintain a vapor processing device in a substantially upright position when in-use.

FIG. 3B shows an example of an adjustable clamp 1002 that may be used as a securement mechanism for support unit 1001. The adjustable clamp 1002 can include processing device engaging jaws. The jaws may include a first jaw 1002a and a second jaw 1002b disposed opposite the first jaw 1002a. The jaws 1002a and 1002b may be used to frictionally engage and secure a vapor processing device.

The first jaw 1002a and second jaw 1002b may be movable towards and away from each other to adjust a separation distance therebetween. This may allow the jaws 1002a and 1002b to be used to receive the vapor processing device. For example, a spacing between the first jaw 1002a and the second jaw 1002b may be adjustable between 6 cm and 15 cm. This may allow various dimensions of vapor processing devices to be coupled to the support unit 1001.

For example, the first and second jaws 1002a and 100b can be mechanically coupled to a rotatable lead screw 1003. Rotation of the lead screw 1003 in a first direction (e.g. a clockwise direction) may cause the jaws 1002a and 1002b to move towards one another, decreasing a separation distance therebetween. If a processing device such as water pipe is positioned between the jaw 1002a and 1002b, this may engage the jaws 1002a and 1002b with the water pipe or may increase a frictional engagement between the jaws 1002a and 1002b and water pipe 421. This may be used to secure the water pipe 421 to support unit 1001.

Rotation of the lead screw 1003 in a second direction (e.g. counter clockwise) may cause the jaws 1002a and 1002b to move away from one another, increasing the separation distance therebetween. If a processing device such as water pipe is positioned between the jaw 1002a and 1002b, this can decrease the frictional engagement between the jaws 1002a and 1002b and water pipe 421. This may allow the water pipe to be removed from support unit 1001.

The first jaw 1002a and second jaw 1002b may be moveable substantially simultaneously to increase or decrease the separation distance therebetween. That is, the lead screw 1003 may cause both first jaw 1002a and second jaw 1002b to move synchronously.

In some embodiments (see e.g. FIG. 4F), the pitch of the thread of lead screw 8003 may prevent the first and second jaws 1002a and 1002b from accidentally disengaging from the water pipe 8421 once they are frictionally engaged.

The support unit 1001 can include a track or tracks for the clamp 1002. For example, the support unit 1001 can include a first track 1401 along which the first jaw 1002a is moveable. The support unit 1001 can also include a second track 1402 along which the second jaw 1002b is moveable. The tracks 1401 and 1402 can be parallel.

In some cases, the support unit 1001 can also include a clamp actuator. The clamp actuator may be usable to adjust the position of the jaws 1002a and 1002b. For example, a thumb screw 1013 may be coupled to lead screw 1003. The thumb screw 1013 may be manually operated by a user to adjust the position of the jaws 1002a and 1002b. The thumb screw 1013 may protrude out from support unit 1001 so it can be easily grasped by a user. This user may adjust the clamp 1002 to accommodate various shapes and sizes of water pipes 421.

Figure 3F:
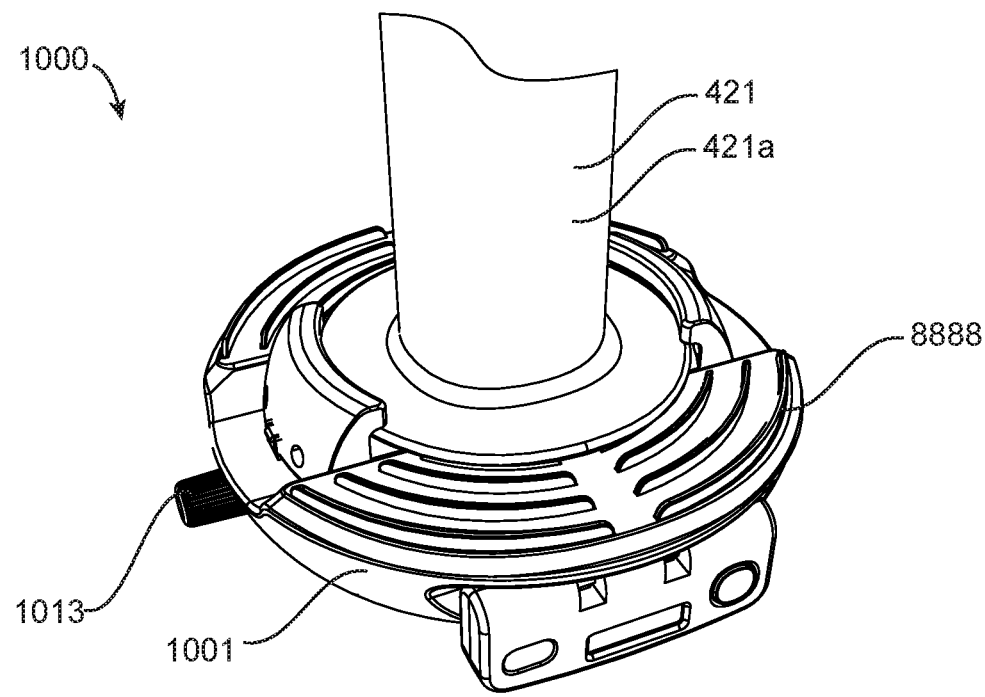
FIG. 3F shows a partial perspective top view of the example support unit shown in FIG. 3B with a first example of a vapor processing device mounted thereto.
Figure 3G:
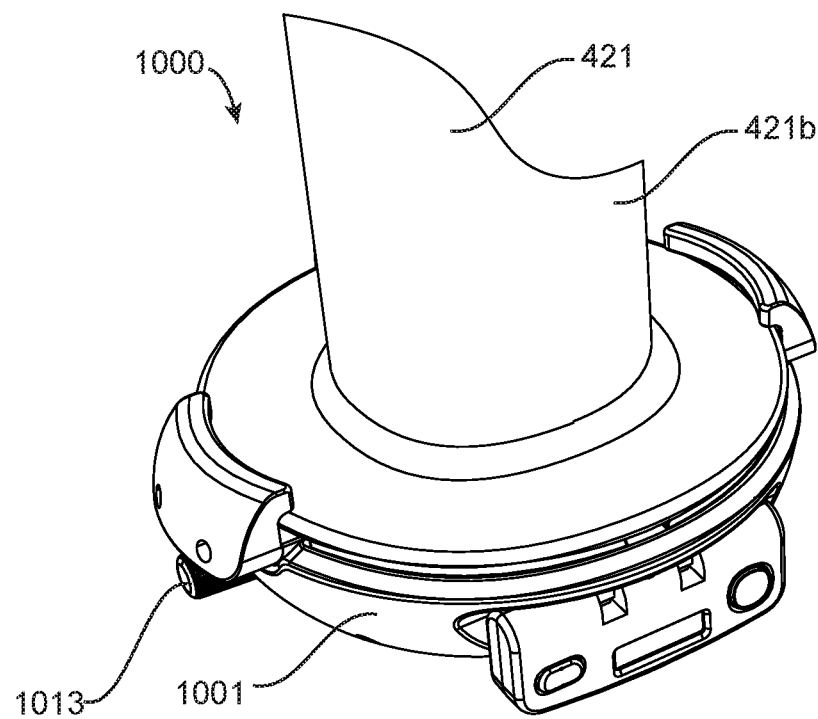
FIG. 3G shows another partial perspective top view of the example support unit shown in FIG. 3B with a second example of a vapor processing device mounted thereto.

FIG. 3F illustrates a first example of a clamp 1002 frictionally engaging a water pipe 421a. FIG. 3G illustrates a second example of the clamp 1002 frictionally engaging a second water pipe 421b. As shown by FIGS. 3F-3G, the jaws 1002a and 1002b are movable to engage water pipes 421 having different diameters.

In some embodiments, the support unit 1001 may also include a plurality of protrusions or ribs 8888. The ribs 8888 may extend out from a base of the support unit 1001. The ribs 8888 may be deformable. The plurality of deformable ribs 8888 may assist in frictionally contacting the water pipe 421 when the jaws 1002a and 1002b engage water pipe 421.

As shown in FIG. 3C, the support unit 1001 can enclose an electrical power source 156. The electrical power source 156 may be usable to power an electrical heater 155 that is provided as part of a vaporization element as described herein above. The electrical power source may also power various other components of a vaporization device, such as control circuits 113/114, communication modules, user interface components etc.

As described herein above, the support unit 1001 may include a control panel 1200. The control panel 1200 may have a rotationally coupled with housing of support unit 1001. The control panel may be movable between a first position (FIG. 3D) and a second position (FIG. 3E). In the first position, the control surface 1200a may be approximately perpendicular to the first track 1401 and the second track 1402. In the second position the control surface 1200a may be approximately parallel to the first track 1401 and the second track 1402.

Figure 3H:
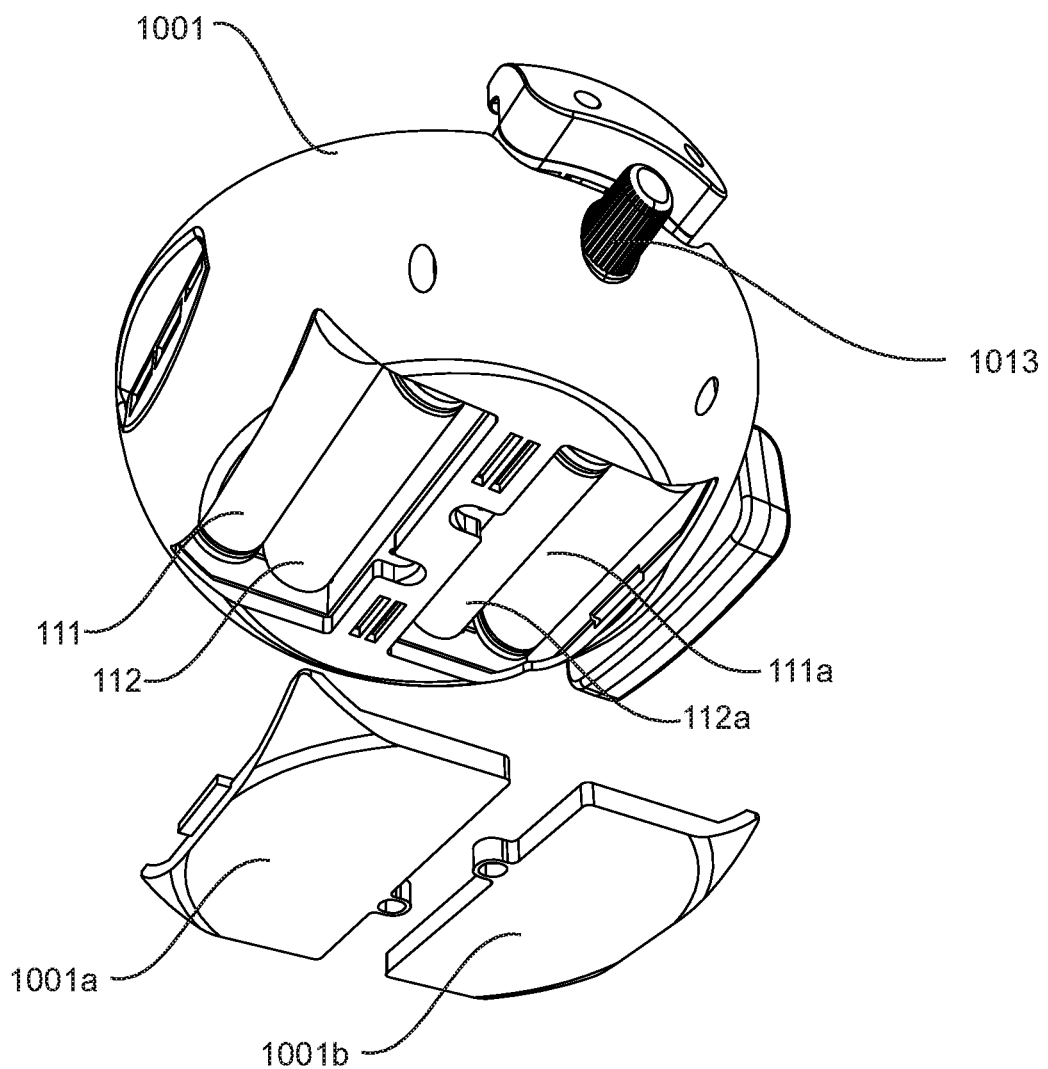
FIG. 3H shows a perspective bottom view of the example support unit shown in FIG. 3B.

FIG. 3H illustrates an example of the bottom side of support unit 1001 in accordance with an embodiment. As shown, the electrical power source 156 may be provided by a plurality of batteries 111, 112, 111a, 112a. For example, the batteries may be provided as lithium ion batteries. The plurality of batteries 111, 112, 111a, 112a may be electrically coupled in series and electrically coupled with the first control circuit 113.

In some cases, the batteries 111, 112, 111a, 112a may be replaceable. For example, the support unit 1001 may include a first battery door 1001a and a second battery door 1001b. The batteries 111 and 112 may be removable through the first battery door 1001a and the batteries 111a and 112a may be removable through the second battery door 1001b.

In some cases, the batteries 111, 112, 111a, 112a may be rechargeable. In some such cases, access to the batteries 111, 112, 111a, 112a may be less important. Accordingly, the battery doors 1001a and 1001b may be omitted, or fixedly secured to support unit 1001 e.g. using screws.

Figure 3I:
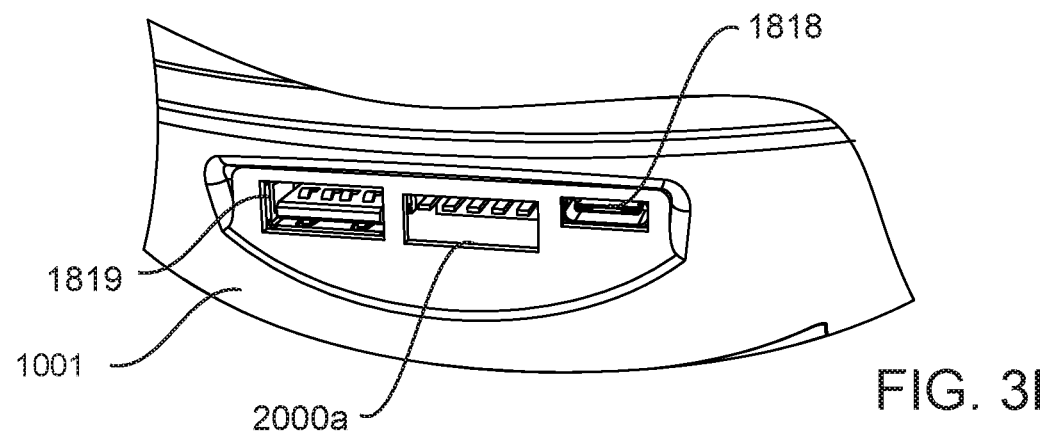
FIG. 3I shows a partial side view of the example support unit shown in FIG. 3B.
Figure 3J:
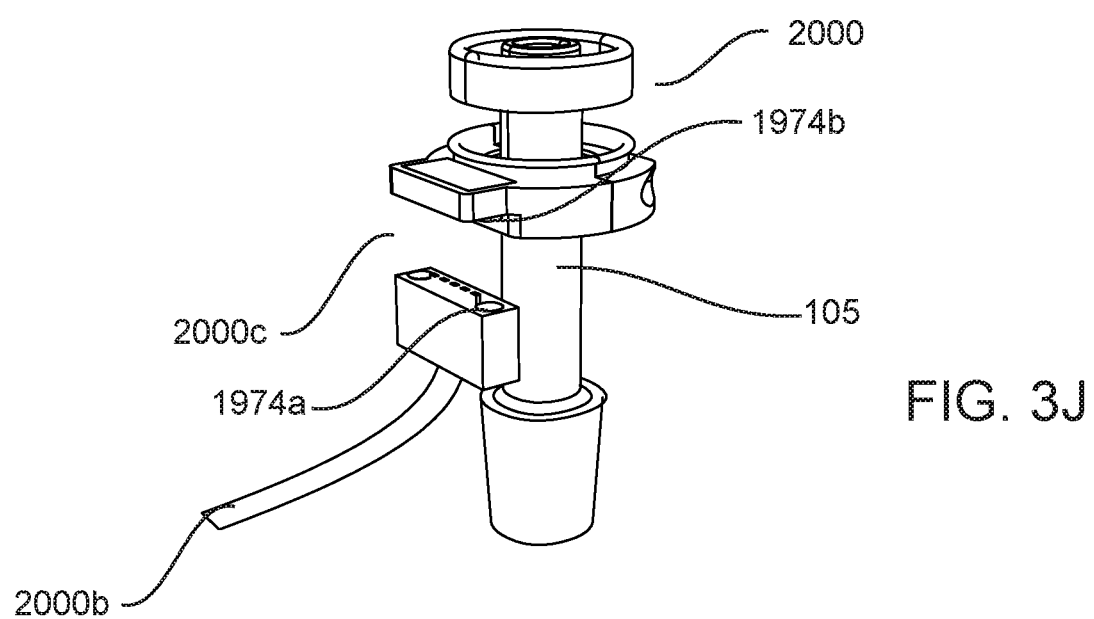
FIG. 3J shows a partial perspective view of the example vaporization element shown in FIG. 3B.

FIG. 3I illustrates an example of the support unit 1001 having a plurality of input and output ports. The input/output ports may include USB ports 1818/1819. The support unit 101 may also include an electronic vaporization element first coupling port 2000a. The ports 1818/1819/2000a may each be electrically coupled to the first control circuit 113.

For example, USB port 1818 may be a USB-C port usable to receive electrical energy from a battery charger. USB port 1819 may be usable to provide power from the electrical power source 156 to connected external devices for being recharged, such as a cellular phone. The support unit 1001 may thus also act as a portable battery bank for recharging other electrical devices in addition to for storing electrical energy for portable heating of the electronic vaporization element 2000.

FIG. 4A illustrates another example embodiment of a support unit 8001. As with support unit 1001, the support unit 8001 may include an onboard electrical power source 156 and control circuit 113.

The support unit 8001 can also include a securement mechanism 8002. The securement mechanism 8002 may be usable to frictionally engage a water pipe 421. As shown in FIGS. 4A and 4B, the support unit 8001 may engage a water trap portion of the water pipe 8421 rather than a base.

Figure 4D:
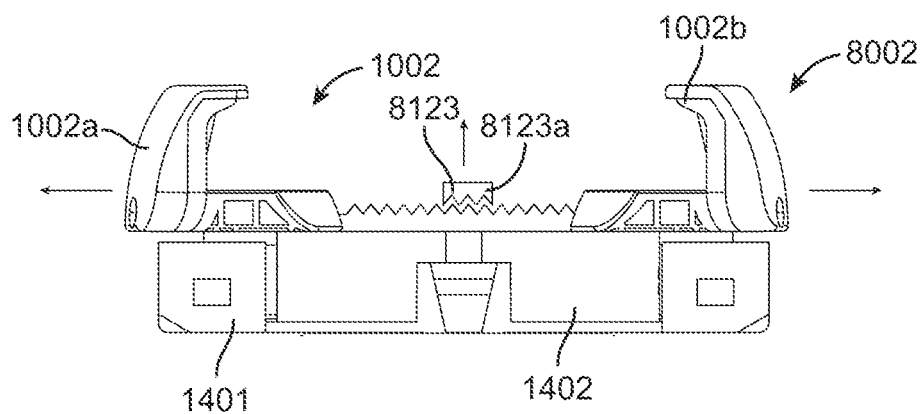
FIG. 4D shows a side view of an example support unit that may be used with the example vaporization device shown in FIG. 4A in accordance with an embodiment.
Figure 4E:
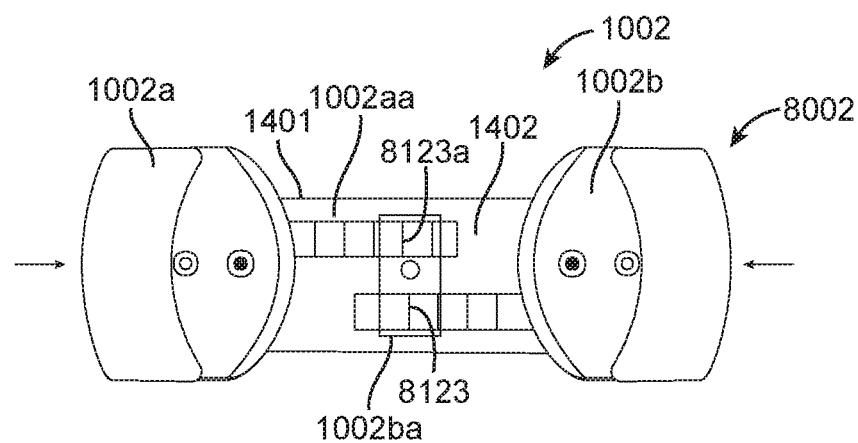
FIG. 4E shows a top view of the example support unit shown in FIG. 4D.

The securement mechanism 8002 may be provided as an adjustable clamp 1002. As shown in the example of FIG. 4D, the clamp 1002 may include a releasable lock 8123. The lock 8123 can be coupled with the first jaw 1002a and the second jaw 1002b.

The lock may be movable between a locked position, in which the jaws 1002a and 1002b are fixed in place along the tracks 1401 and 1402 respectively, and an unlocked position in which the jaws 1002a and 1002b are moveable along tracks 1401 and 1402 respectively.

The releasable lock 8123 may operate in a manner similar to a releasable zip tie. The lock 8123 may include a plurality of mating ratchet teeth 8123a. The teeth 8123a may be coupled to jaws 1002a and 1002b. As the jaws 1002a and 1002b are moved towards one another, the teeth 8123a can be ratcheted past a release member 8123b.

In the locked position, the release member 8123b may be lowered to prevent the teeth 8123a from moving in the opposite direction, thereby preventing jaws 1002a and 1002b from being separated. In the unlocked position, release member 8123b can be raised to disengage the ratchet teeth 8123a and allow the jaws 1002a and 1002b to separate. The release member 8123b can be biased to the locked position to prevent the jaws 1002a and 1002b from being separated unintentionally.

Figure 4F:
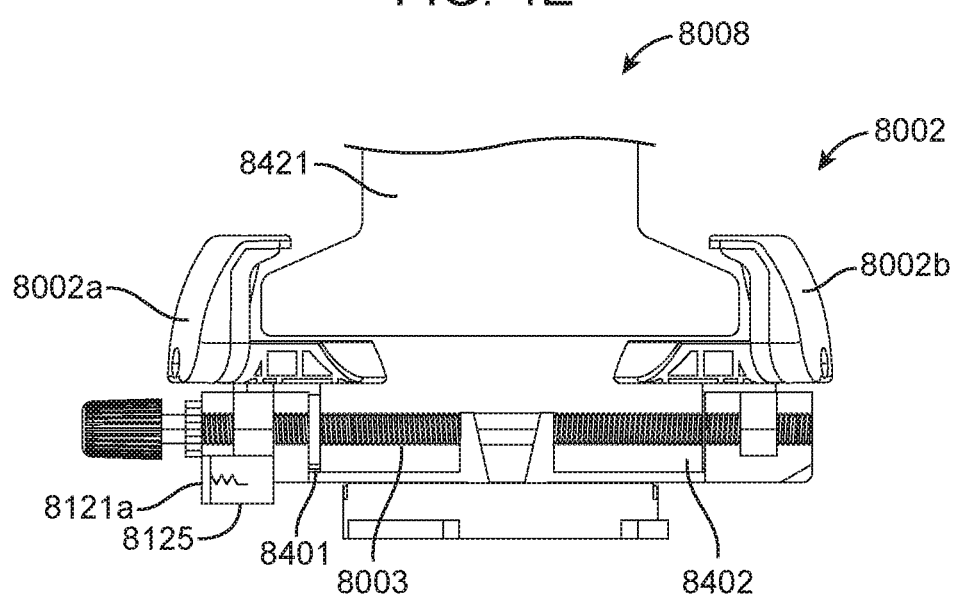
FIG. 4F shows a side view of the example support unit shown in FIG. 4D in a locked position.
Figure 4G:
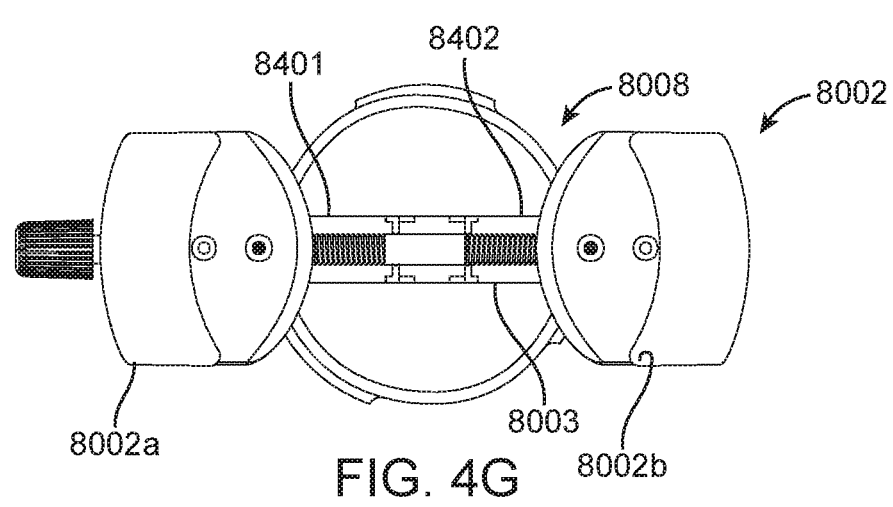
FIG. 4G shows a top view of the example support unit shown in FIG. 4D in an unlocked position.

In some embodiments, as shown in FIG. 4F, the support 1001 may include a motor 8125. The motor 8125 may be mechanically coupled to the lead screw 8003. The motor 8125 may be operable to actuate the rotation of lead screw 8003.

The motor 8125 may also be electrically coupled to the first control circuit 113. The control circuit 113 may controllably actuate the motor 8125 to rotate the lead screw 8003, and thereby adjust the separation between the jaws 1002a and 1002b. The motor 8125 may facilitate frictional engaging the water pipe 8421 without having to manually turn the lead screw 8003. In some embodiments, a clutch 8125a may couple the motor 8125 to the lead screw 8003.

This may allow the lead screw 8003 to be moved manually without requiring use of the motor 8125.

In some embodiments, as shown in FIGS. 5A-5D, the support unit 8010 may include a twist lock coupling 8678. The twist lock coupling 8678 may be used to secure a water pipe 8421 to support unit 8010.

The twist coupling 8678 may include a rotatable portion 8678a and a static portion 8678b. The rotatable portion 8678a may be coupled to an adjustable clamp 8008. The adjustable clamp 8008 can be used to secure a water pipe to the rotating portion 8678a (e.g. as described above).

The static portion 8678b can be fixed to the support unit 8010. For instance, the static portion 8678b may be formed as part of the housing of support unit 8010.

The twist coupling 8678 may be adjustable between a locked position and an unlocked position. FIGS. 5A and 5B illustrate an example of the twist lock coupling 8678 in an unlocked position. In the unlocked position the rotating portion 8678a and static portion 8678b can be separated. Accordingly, the water pipe can be uncoupled from the support unit 8010.

FIGS. 5A and 5B illustrate an example of the twist lock coupling 8678 in a locked position. In the locked position, the rotating portion 8678a can be frictionally engaged with the static portion 8678b. If a water pipe is secured to clamp 8008, the water pipe may thus be secured to the support unit 8010 by the twist lock coupling 8678.

In order to transition from the unlocked position to the locked position, the rotating portion 8678a can be pushed against the support unit 8010 and oriented such that twist lock coupling 8678 is aligned at a predetermined starting orientation, as shown in FIG. 5A. The rotating portion 8678a can then be twisted into place as is shown in FIG. 5B.

The static portion 8678b may define a mating receptacle shaped to receive the rotating portion 8678a. For instance, the rotating portion 8678a may include one or more protrusions extending from a side thereof. The static portion 8678a may include one or more corresponding notches. The rotating portion 8678a may then be inserted into the static portion when the protrusions and notches are aligned. The rotating portion 8678a may then be rotated while inserted into the static portion 8678b. The protrusions may then securely engage the rotating portion 8678a and static portion 8678b.

The twist lock coupling 8678 may allow the water pipe 8421 to be secured to clamp 8008 while removed from the support unit 8010. This may allow the water pipe 8421 to be cleaned or filled with water while secured to the adjustable clamp 8008. Accordingly, the risk of spillage when securing the water pipe 8421 to the clamp 8008 may be mitigated.

This may also facilitate the design and construction of the base of support unit 8010. As the clamp 8008 may be separated from the housing of the support unit 8010, fewer movable parts may be required to manufacture the housing of support unit 8010. This may allow different shapes and types of clamps 8008 to be used with support unit 8010, to support different types of water pipes. Additionally, this may facilitate replacement in case of failure of the clamp 8008.

In some embodiments, the support unit 1001 may include alternative water pipe securement mechanisms. In some such embodiments, the clamp 1002 may be omitted.

For example, FIG. 6D illustrates an example of a securement mechanism 8002 in the form of a suction cup 8102. In some embodiments, the suction cup 8102 may be an active suction cup in which the support unit 8001 includes an actuator that pulls the water pipe 8421 onto the cup 8102 in response to an activation switch. The water pipe 8421 may be placed in proximity to the suction cup 8102, a button can be pressed and the water pipe 8421 can be sucked onto the suction cup 8102 generating a vacuum therebetween securing the water pipe 8421 to the suction cup 8102. Alternatively, a user may manually secure the water pipe 8421 to the suction cup 8102.

FIG. 6I illustrates another alternative example in which an adhesive 8022 is used as a securement mechanism. In the example shown in FIG. 6I, the adhesive 8022 may be an adhesive tape that can adhere the water pipe 8421 to the rotating portion 8678*a*. Optionally the water pipe 8421 may be adhered directly to the first housing 8010.

Various alternative securement mechanisms may also be used in embodiments of the support units 1001 described herein. For instance, hook and loop fasteners may be used to secure the water pipe 8421 (or a clamp 8008) to support unit 8010. In some embodiments, hook and loop fasteners may be used to secure the water pipe 8421 to the rotating portion 8678*a* rather than directly to support unit 8010. Zip ties or other fastening system may also be used to frictionally engage the water pipe 8421 to the rotating portion 8678*a* or directly to support unit 8010.

In some cases, magnets may be used to couple the water pipe 8421 to the rotating portion 8678*a* or directly to support unit 8010. For example, one or more magnets may be adhered to the water pipe 8421 and corresponding magnets may be provided as part of the support unit 8010.

As used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

While the above description describes features of example embodiments, it will be appreciated that some features and/or functions of the described embodiments are susceptible to modification without departing from the spirit and principles of operation of the described embodiments. For example, the various characteristics which are described by means of the represented embodiments or examples may be selectively combined with each other. Accordingly, what has been described above is intended to be illustrative of the claimed concept and non-limiting. It will be understood by persons skilled in the art that other variants and modifications may be made without departing from the scope of the invention as defined in the claims appended hereto. The scope of the claims should not be limited by the preferred embodiments and examples, but should be given the broadest interpretation consistent with the description as a whole.

The invention claimed is:

1. A vaporization device for vaporizing phyto material, the vaporization device being fluidly engageable with a vapor processing device, the vapor processing device having an input port and an inhalation aperture with a vapor processing device fluid pathway formed between the input port and the inhalation aperture, the vaporization device comprising:
   a) a vaporization element comprising:
      i) a hollow member extending from a first end to a second end opposite the first end, the hollow member defining a vaporization element fluid pathway from a vapor inlet positioned at the first end to a vapor outlet positioned at the second end, wherein the hollow member is engageable with the vapor processing device with the vapor outlet fluidly engaged with the input port;
      ii) a vaporization section having a first curved inner wall surface and a first curved outer wall surface, the vaporization section having a vaporization section first end and a vaporization section second end opposite the vaporization section first end with the first curved outer wall surface extending from the first end to the second end, wherein the vaporization section defines a vaporization section volume bounded by the first curved inner wall surface, the first curved outer wall surface, the vaporization section first end and the vaporization section second end, and wherein the first end of the hollow member is fluidly coupled with the vaporization section volume,
      iii) a heater section within which an electrical heating unit is positioned, the electrical heating unit being proximate to the first end of the hollow member; and
      iv) a phyto material contact element having a first side positioned at the vaporization section second end and a second side positioned adjacent the heater section, the first side of the phyto material contact element defining a phyto material contact surface at the vaporization section second end, wherein the phyto material contact element separates the electrical heating unit from the phyto material contact surface, wherein the phyto material contact surface is disposed proximate to, and below, the first end of the hollow member;
   b) a support unit that is removably mountable to the vapor processing device, the support unit having a bottom surface and a top surface opposite the bottom surface, wherein the top surface comprises:
      i) a mount usable to securely attach the vapor processing device to the support unit in an upright position when the support unit is positioned in an in-use position in which the top surface faces substantially upwards;
      ii) an electrical power source; and,
      iii) a control circuit electrically coupled to the electrical power source; and
   c) an electrical connector that is engageable with the support unit and the vaporization element whereby the electrical heating unit is coupled to the control circuit;
   wherein the control circuit is configured to controllably provide electrical power from the electrical power source to the electrical heating unit and thermal energy from the electrical heating unit is transmittable through the phyto material contact element from the second side of the phyto material contact element to the phyto material contact surface to heat the phyto material contact surface to a predefined vaporization temperature whereby when phyto material is positioned on the phyto material contact surface a vapor is emitted.

2. A vaporization device according to claim 1, further comprising:
   a) a temperature sensor in thermal communication with at least one of the second side of the phyto material contact element and the electrical heating unit, the temperature sensor operable to measure a temperature of the at least one of the second side of the phyto material contact element and the electrical heating unit and to generate a temperature signal based on the measured temperature;
   wherein the control circuit is configured to receive the temperature signal from the temperature sensor and to determine a temperature of the phyto material contact surface based on the received temperature signal.

3. A vaporization device according to claim 2, wherein:
a) the support unit comprises a first wireless transceiver and a power coupling output port;
b) the vaporization element comprises a power coupling input port, a second wireless transceiver and a second control circuit that is electrically coupled to the electrical heating unit, to the power coupling input port, to the second wireless transceiver, and to the temperature sensor, and the second control circuit is configured to determine a temperature of the electrical heating unit;
c) the electrical connector is connectable to the power coupling output port and to the power coupling input port to electrically couple the electrical heating unit to the control circuit; and
d) the control circuit is configured to receive the temperature signal from the second control circuit via the first wireless transceiver and the second wireless transceiver.

4. A vaporization device according to claim 1, wherein the electrical heating unit is releasably attached to the heater section using a frictional coupling.

5. A vaporization device according to claim 1, wherein the support unit comprises an orientation sensor electrically coupled with the control circuit, wherein the orientation sensor is operable to generate a tilt signal upon determining that the support unit is not positioned in the in-use position, and the control circuit is configured to disable the electrical heating unit in response to the tilt signal.

6. The vaporization device according to claim 1, wherein the heater section and the vaporization section are coaxial.

7. The vaporization device according to claim 1, wherein the heater section comprises an insulative skirt wherein the insulative skirt may substantially surround the phyto material contact element and assist in holding the electrical heating unit proximate the phyto material contact element.

8. The vaporization device according to claim 1, wherein the heater section volume comprises an insulative skirt region with inner sidewalls extending to the phyto material vaporization region wherein the phyto material vaporization region may be insulated by the inner sidewalls of the heater section.

9. The vaporization device according to claim 8, wherein the inner sidewalls of the heater section may comprise one of glass and ceramic.

10. The vaporization device according to claim 1, wherein the phyto material contact element comprises is formed integrally with the vaporization section.

11. The vaporization device according to claim 1, the phyto material contact element is a removable contact element that is removably insertable between the first end of the hollow member and the electrical heating unit.

12. The vaporization device according to claim 11, wherein the phyto material contact element comprises a first material, the vaporization section comprises a second material, and the first material provides greater heat transfer from the heater section to the phyto material contact surface.

13. The vaporization device according to claim 1 wherein in use, the vaporization element is configured to engage with the vapor processing device such that a shared axis along which the vaporization section and heater section extend is substantially parallel to a direction of gravity, heat from the electrical heating unit is inclined to travel upwards from the heater section to the vaporization section and facilitates the vapor to travel upwards to the vapor inlet.

14. The vaporization device according to claim 1 wherein the phyto material contact element is manufactured from at least one material from a group consisting of ceramic, glass, silicone carbide, Aluminum Nitride, Sapphire, Alumina, and Silicon Nitride.

15. The vaporization device according to claim 1 wherein the electrical heating unit comprises one of a resistive coil or a stamped resistive heater.

16. The vaporization device according to claim 1, wherein a first portion of the vaporization element fluid pathway extends along a vapor inlet axis and a second portion of the vaporization element fluid pathway extends along a vapor outlet axis wherein the vapor inlet axis and the vapor outlet axis are non-coaxial.

17. The vaporization device according to claim 1, wherein the hollow member is manufactured using a non brittle material other than ceramic or glass.

18. The vaporization device according to claim 1 wherein the phyto material contact element comprises a cup heater having a first open end and phyto material is insertable into the cup heater via the first open end.

19. The vaporization device according to claim 18 wherein:
a) the vaporization element includes a removable lid, wherein the lid is adjustable between an open position and a closed position, wherein when the lid is in the open position phyto material is loadable into the vaporization element and residue is removable from the vaporization element, and when the lid is in the closed position the lid facilitates vaporization of phyto material positioned on the phyto material contact surface; and
b) the vaporization element includes an ambient air inlet positioned to allow ambient air to flow and become entrained with the vapor into the fluid pathway when the lid is in the closed position.

20. The vaporization device according to claim 1 wherein the phyto material contact element comprises one of a glass or a ceramic or a metal.

21. A method for vaporizing phyto material comprising:
a) providing a vaporization element comprising:
i) a vaporization section having a first curved inner wall surface and a first curved outer wall surface, the vaporization section having a vaporization section first end and a vaporization section second end opposite the vaporization section first end with the first curved outer wall surface extending from the first end to the second end, wherein the vaporization section defines a vaporization section volume bounded by the first curved inner wall surface, the first curved outer wall surface, the vaporization section first end and the vaporization section second end;
ii) a heater section within which an electrical heating unit is positioned; and
b) positioning a removable phyto material contact element at the vaporization section second end, the phyto material contact element having a central axis of symmetry, a first side positioned at the vaporization section second end and a second side positioned adjacent the heater section, the first side of the phyto material contact element defining a phyto material contact surface and the second side of removable phyto material contact element in thermal communication with the electrical heating unit, wherein the phyto material contact element is positioned to separate the electrical heating unit from the phyto material contact surface, wherein the phyto material contact surface is positioned proximate to, and below, the first end of the hollow member, wherein thermal energy from the electrical heating unit is transmittable through the phyto material contact element from the second side of the phyto material contact element to the phyto material contact surface and the phyto material contact element is frictionally engageable between the vaporization section and the electrical heating unit;

c) providing a hollow member coupled to the vaporization section, the hollow member having a first end defining a vapor inlet and a second end opposite the first end, the hollow member defining a vaporization element fluid pathway extending from the first end to the second end, wherein the first end of the hollow member is coupled with a vaporization section volume defined by the vaporization section with the hollow member proximate to the electrical heating unit;

d) coupling the second end of the hollow member to an input port of a vapor processing device, the vapor processing device having a vapor processing device pathway extending from the input port to an inhalation aperture;

e) mounting a support unit to the vapor processing device, the support unit having a first side and a second side opposite the first surface wherein the second side of the support unit frictionally engages the vapor processing device whereby the vapor processing device is maintainable in an upright position when the support unit is positioned in an in-use position in which the second side faces substantially upwards, the support unit comprising an electrical power source;

f) depositing phyto material extract onto the phyto material contact surface; and g) heating the electrical heating unit to a predetermined vaporization temperature using electrical power from the electrical power source whereby the deposited phyto material extract on the phyto material contact surface is vaporized thereby emitting vapor that, in response to inhalation from the inhalation aperture, is drawn into the vapor inlet to the vapor outlet and through the vapor processing device fluid pathway to the inhalation aperture.

22. A method for vaporizing phyto material according to claim 21 further comprising: cooling the vapor through contact with the inner walls of the hollow member as the vapor travels along the vaporization element fluid pathway.

23. A method for vaporizing phyto material according to claim 21 wherein mounting the support unit to the vapor processing device comprises frictionally engaging the vapor processing device with the support unit using a mounting element.

24. A vaporization device for vaporizing phyto material, the vaporization device being fluidly engageable with a vapor processing device, the vapor processing device having an input port and an inhalation aperture with a vapor processing device fluid pathway formed between the input port and the inhalation aperture, the vaporization device comprising:

a hollow member extending from a first end to a second end opposite the first end, the hollow member defining a vaporization element fluid pathway extending from a vapor inlet positioned at the first end to a vapor outlet positioned at the second end, wherein the vapor outlet is fluidly engageable with the vapor processing device input port;

a vaporization section having a first curved inner wall surface and a first curved outer wall surface, the vaporization section having a vaporization section first end and a vaporization section second end opposite the vaporization section first end with the first curved outer wall surface extending from the first end to the second end, wherein the vaporization section defines a vaporization section volume bounded by the first curved inner wall surface, the first curved outer wall surface, the vaporization section first end and the vaporization section second end, and wherein the first end of the hollow member is fluidly coupled with the vaporization section volume, a heater section within which an electrical heating unit is positioned; and a phyto material contact element having a first side positioned at the vaporization section second end and a second side positioned adjacent the heater section, the first side of the phyto material contact element defining a phyto material contact surface at the vaporization section second end, the phyto material contact surface being disposed proximate to the first end of the hollow member, wherein the phyto material contact element separates the electrical heating unit from the phyto material contact surface, wherein the vaporization section and the heater section and the phyto material contact element are coaxially disposed and the hollow member is proximate to the electrical heating unit;

a support unit, the support unit having a bottom surface and a top surface opposite the bottom surface, the support unit comprises:

an electrical power source disposed within the support unit; and, a control circuit disposed within the support unit and electrically coupled to the electrical power source;

a temperature sensor in thermal communication with at least one of the electrical heating unit or the second side of the phyto material contact element, the temperature sensor operable to measure a temperature of the at least one of the second side of the phyto material contact element or the electrical heating unit to generate a temperature signal based on the measured temperature, wherein the control circuit is configured to receive the temperature signal from the temperature sensor and to determine a temperature of the phyto material contact surface based on the received temperature signal, wherein the control circuit is configured to correlate a sensed temperature as received from the temperature signal and the temperature of the phyto material contact surface using calibration data stored in a lookup table; and, an electrical connector cable that is engageable with the support unit and the vaporization element whereby the electrical heating unit is coupled to the control circuit, wherein the control circuit is configured to controllably provide electrical power from the electrical power source to the electrical heating unit and thermal energy from the electrical heating unit is transmittable through the phyto material contact element from the second side of the phyto material contact element to the phyto material contact surface and to the wall proximate the second end to heat the phyto material contact surface to a predefined vaporization temperature, whereby when phyto material is positioned on the phyto material contact surface a vapor is emitted and the vapor is propagatable from the vapor inlet positioned at the first end to the vapor outlet through the vapor processing device fluid pathway to the inhalation aperture.

25. A vaporization device for vaporizing phyto material, the vaporization device being fluidly engageable with a vapor processing device, the vapor processing device having an input port and an inhalation aperture with a vapor processing device fluid pathway formed between the input port and the inhalation aperture, the vaporization device comprising:
  a hollow member extending from a first end to a second end opposite the first end, the hollow member defining a vaporization element fluid pathway from a vapor inlet positioned at the first end to a vapor outlet positioned at the second end, wherein the vapor outlet is fluidly engageable with the vapor processing device input port;
  a vaporization element comprising:
    a vaporization section having a first curved inner wall surface and a first curved outer wall surface, the vaporization section having a vaporization section first end and a vaporization section second end opposite the vaporization section first end with the first curved outer wall surface extending from the first end to the second end, wherein the vaporization section defines a vaporization section volume bounded by the first curved inner wall surface, the first curved outer wall surface, the vaporization section first end and the vaporization section second end, and wherein the first end of the hollow member is fluidly coupled with the vaporization section volume,
    a heater section comprising a heating unit, and
    a phyto material contact element having a first open end for receiving phyto material through the first open end, at least one side wall and a contact element base, the contact element base defining a phyto material contact surface, the at least one side wall for surrounding the phyto material and usable to heat the phyto material, wherein the contact element base separates the phyto material contact surface from the heating unit, wherein the phyto material contact surface is provided on a first side of the contact element base and the heating unit is positioned on a second side of the contact element base, and wherein the phyto material contact surface is disposed proximate to, and below, the first end of the hollow member;
  a support unit that is removably mountable to the vapor processing device, the support unit having a bottom surface and a top surface opposite the bottom surface, wherein the top surface comprises:
  a mount usable to secure the vapor processing device to the support unit in an upright position when the support unit is positioned in an in-use position in which the top surface faces substantially upwards;
  an electrical power source; and,
  a control circuit electrically coupled to the electrical power source; and
  an electrical connector that is engageable with the support unit and the vaporization element whereby the heating unit is coupled to the control circuit,
  wherein the control circuit is configured to controllably provide electrical power from the electrical power source to the heating unit and thermal energy from the heating unit is transmittable through the phyto material contact element from the second side of the contact element base to the phyto material contact surface to heat the phyto material contact surface to a predefined vaporization temperature whereby when phyto material is received by the phyto material contact element a vapor is emitted and the vapor is propagatable from the vapor inlet positioned at the first end to the vapor outlet through the vapor processing device fluid pathway to the inhalation aperture.

26. The vaporization device of claim 25, wherein the heating element comprises an annular heating element.

27. The vaporization device of claim 26, wherein the annular heating element comprises an annular cup.

28. The vaporization device of claim 25, wherein the heating element comprises a circular cup heating element.

29. A vaporization device for vaporizing phyto material according to claim 28, wherein the circular cup heating element comprises a partially perforated phyto material holder portion for supporting the phyto material and for allowing ambient air and vapor to propagate through the holder portion into the vapor processing device input port.

30. A vaporization device for vaporizing phyto material comprising:
  a vapor processing device having an input port and an inhalation aperture with a vapor processing device fluid pathway formed between the input port and the inhalation aperture, the vapor processing device comprising a water trap section positioned in the processing device fluid pathway;
  a vaporization element comprising a hollow member extending from a first end to a second end opposite the first end, the hollow member defining a vaporization element fluid pathway extending from a vapor inlet positioned at the first end to a vapor outlet positioned at the second end, wherein the vapor outlet is fluidly engaged with the vapor processing device input port;
  a vaporization section having a first curved inner wall surface and a first curved outer wall surface, the vaporization section having a vaporization section first end and a vaporization section second end opposite the vaporization section first end with the first curved outer wall surface extending from the first end to the second end, wherein the vaporization section defines a vaporization section volume bounded by the first curved inner wall surface, the first curved outer wall surface, the vaporization section first end and the vaporization section second end, and wherein the first end of the hollow member is fluidly coupled with the vaporization section volume,
  a phyto material contact element having a first side positioned at the vaporization section second end and a second side positioned in thermal communication with an electrical heating unit, the first side of the phyto material contact element defining a phyto material contact surface at the vaporization section second end, the phyto material contact surface disposed proximate to, and below, the first end of the hollow member, wherein the phyto material contact element separates the electrical heating unit from the phyto material contact surface, wherein the vaporization section and the electrical heating unit and the phyto material contact element are coaxially disposed and the hollow member is proximate to the electrical heating unit;
  a support unit, the support unit having a bottom surface and a top surface opposite the bottom surface, the support unit comprises:
    an electrical power source disposed within the support unit; and,
    a control circuit disposed within the support unit and electrically coupled to the electrical power source;
    a connector cable integral with the support unit to electrically couple the vaporization element to the control circuit and electrical power source, the vaporization element and support unit each including connector ports that correspond to the connector cable;

a temperature sensor in thermal communication with at least one of the electrical heating unit or the second side of the phyto material contact element, the temperature sensor operable to measure a temperature of the at least one of the electrical heating unit or the second side of the phyto material contact element to generate a temperature signal based on the measured temperature; and, wherein the control circuit is configured to receive the temperature signal from the temperature sensor and is configured to controllably provide electrical power from the electrical power source to the electrical heating unit through the connector cable and thermal energy from the electrical heating unit is transmittable through the phyto material contact element from the second side of the phyto material contact element to the phyto material contact surface to heat the phyto material contact surface to a predefined vaporization temperature;

whereby when phyto material is positioned on the phyto material contact surface a vapor is emitted and the vapor is propagatable from the vapor inlet positioned at the first end to the vapor outlet through the vapor processing device fluid pathway to the inhalation aperture.

31. A vaporization device according to claim 30 wherein the connector cable comprises at least three conductor lines comprising a ground conductor line and a positive voltage conductor line and a temperature signal line.

32. A vaporization device according to claim 30 wherein
a) the vaporization element includes a removable lid, wherein the lid is adjustable between an open position and a closed position, wherein when the lid is in the open position phyto material is loadable into the vaporization element and residue is removable from the vaporization element, and when the lid is in the closed position the lid facilitates vaporization of phyto material positioned on the phyto material contact surface; and
b) the vaporization element includes an ambient air inlet positioned to allow ambient air to flow and become entrained with the vapor into the fluid pathway when the lid is in the closed position.

33. A vaporization device for vaporizing phyto material comprising:
a vapor processing device having an input port and an inhalation aperture with a vapor processing device fluid pathway formed between the input port and the inhalation aperture, the vapor processing device comprising a water trap section positioned in the processing device fluid pathway;
a vaporization element comprising a hollow member extending from a first end to a second end opposite the first end, the hollow member defining a vaporization element fluid pathway extending from a vapor inlet positioned at the first end to a vapor outlet positioned at the second end, wherein the vapor outlet is fluidly engaged with the vapor processing device input port;
a vaporization section having a first curved inner wall surface and a first curved outer wall surface, the vaporization section having a vaporization section first end and a vaporization section second end opposite the vaporization section first end with the first curved outer wall surface extending from the first end to the second end, wherein the vaporization section defines a vaporization section volume bounded by the first curved inner wall surface, the first curved outer wall surface, the vaporization section first end and the vaporization section second end, and wherein the first end of the hollow member is fluidly coupled with the vaporization section volume,
a phyto material contact element having a first side positioned at the vaporization section second end and a second side, an electrical heating unit at least partially embedded into the phyto material contact element, wherein the electrical heating unit is one of embedded or sintered into the phyto material contact element, the first side of the phyto material contact element defining a phyto material contact surface disposed proximate to the first end of the hollow member, wherein the phyto material contact element separates the electrical heating unit from the phyto material contact surface, wherein the vaporization section and the phyto material contact element are coaxially disposed and the hollow member is proximate to the electrical heating unit;
a support unit, the support unit having a bottom surface and a top surface opposite the bottom surface, the support unit comprises:
an electrical power source disposed within the support unit; and,
a control circuit disposed within the support unit and electrically coupled to the electrical power source;
a connector cable integral with the support unit to electrically couple the vaporization element to the control circuit and electrical power source, the vaporization element and support unit each including connector ports that correspond to the connector cable;
wherein the control circuit is configured to controllably provide electrical power from the electrical power source to the electrical heating unit through the connector cable and thermal energy from the electrical heating unit is transmittable into the phyto material contact element to the phyto material contact surface to heat the phyto material contact surface to a predefined vaporization temperature;
whereby when phyto material is positioned on the phyto material contact surface and the phyto material contact surface is heated to a predefined vaporization temperature a vapor is emitted and when air is drawn in through the vapor inlet the vapor propagates from the vapor inlet positioned at the first end to the vapor outlet through the vapor processing device fluid pathway to the inhalation aperture.

34. A vaporization device for vaporizing phyto material according to claim 33 wherein the phyto material comprises phyto material extract and the predefined vaporization temperature is between 550 Fahrenheit to 700 Fahrenheit.

* * * * *